(12) United States Patent
Palmroos et al.

(10) Patent No.: US 7,896,842 B2
(45) Date of Patent: Mar. 1, 2011

(54) SYSTEM FOR GUIDING A USER DURING PROGRAMMING OF A MEDICAL DEVICE

(75) Inventors: John Erik Michael Palmroos, San Diego, CA (US); James Bradley DuBois, Desert Hills, AZ (US); David Cassidy, Chandler, AZ (US); Glenn Davis, Grayslake, IL (US); Raymond P. Silkaitis, Lake Forest, IL (US)

(73) Assignee: Hospira, Inc., Lake Forest, IL (US)

( * ) Notice: Subject to any disclaimer, the term of this patent is extended or adjusted under 35 U.S.C. 154(b) by 45 days.

(21) Appl. No.: 11/959,330

(22) Filed: Dec. 18, 2007

(65) Prior Publication Data

US 2008/0200870 A1 Aug. 21, 2008

Related U.S. Application Data

(63) Continuation-in-part of application No. 11/103,235, filed on Apr. 11, 2005.

(51) Int. Cl.
*A61M 1/00* (2006.01)
(52) U.S. Cl. .................. 604/151; 604/67; 604/65; 604/500; 604/48
(58) Field of Classification Search ............. 604/65–67, 604/890.1–892.1, 500–512
See application file for complete search history.

(56) References Cited

U.S. PATENT DOCUMENTS

| | | | |
|---|---|---|---|
| 4,898,578 A | 2/1990 | Rubalcaba, Jr. | |
| 5,562,615 A | 10/1996 | Nassif | |
| 5,609,575 A * | 3/1997 | Larson et al. | 604/65 |
| 5,713,856 A * | 2/1998 | Eggers et al. | 604/65 |
| 5,744,027 A | 4/1998 | Connell et al. | |
| 5,990,838 A | 11/1999 | Burns et al. | |
| 6,456,245 B1 | 9/2002 | Crawford | |
| 6,741,212 B2 | 5/2004 | Kralovec et al. | |
| 6,790,198 B1 | 9/2004 | White et al. | |
| 7,253,779 B2 | 8/2007 | Greer et al. | |
| 2002/0013551 A1 | 1/2002 | Zaitsu et al. | |
| 2002/0038392 A1 | 3/2002 | De La Huerga | |
| 2003/0140928 A1 | 7/2003 | Bui et al. | |
| 2004/0176984 A1 | 9/2004 | White et al. | |
| 2005/0182366 A1 | 8/2005 | Vogt et al. | |
| 2006/0042633 A1 | 3/2006 | Bishop et al. | |
| 2006/0229557 A1 | 10/2006 | Fathallah et al. | |
| 2006/0258985 A1* | 11/2006 | Russell | 604/151 |
| 2007/0213598 A1 | 9/2007 | Howard et al. | |

OTHER PUBLICATIONS

Bektas, et al, "Bluetooth Communication Employing Antenna Diversity", Computers and Communication, Jun. 30, 2003, pp. 652-657.

* cited by examiner

*Primary Examiner*—Nicholas D Lucchesi
*Assistant Examiner*—Leah Stohr
(74) *Attorney, Agent, or Firm*—Michael R. Crabb

(57) ABSTRACT

A medical pump that provides advance guidance to a user regarding existence and limits of a valid input range for a pump programming parameter includes an input device for entering a value of a pump programming parameter, a memory for storing constraints related to the pump programming parameter, and a processor in communication with the memory and the input device. The processor dynamically utilizes the constraints to determine and generate a signal indicating whether a valid input range exists for a to-be-entered value of the pump programming parameter and notifies the user.

21 Claims, 56 Drawing Sheets

FIG. 2

- A 0mL/HR
- 0mL
- UNC

BOLUS | PROGRAM | ADVANCED | PIGGYBACK

INFUSION: OTHER DRUG [700 nanog/100mL]

DOSE: 0 GRAMS/MIN

WEIGHT: 0 kg
HEIGHT: 0 cm
BSA: 0 m² CALCULATE

CANCEL    ENTER

PRESS FIELDS TO EDIT. CANCEL TO EXIT WITHOUT SAVING CHANGES. ENTER TO SAVE CHANGES AND CONTINUE.

MODE | SETTINGS | LOGS | LOCK | ALARM

SYSTEM FOR GUIDING A USER DURING PROGRAMMING OF A MEDICAL DEVICE

CROSS-REFERENCE TO RELATED APPLICATIONS

This application is a continuation-in-part of U.S. Ser. No. 11/103,235, filed Apr. 11, 2005, the entire disclosure of which is hereby expressly incorporated by reference herein.

BACKGROUND OF THE INVENTION

This invention relates to systems that are used to dispense medication. More specifically, this invention relates to a system for guiding a user during the programming of a medical device, such as a pump or a processor in communication with a pump, wherein the system notifies the user in advance of whether a valid input range exists for a particular selected parameter that is about to be entered by the user and advises the user of the permissible values or valid range of values for the parameter selected.

Many medical devices such as infusion pumps that supply medication to a patient need to have a physician, pharmacist, nurse, the patient or the like manually or electronically enter information regarding the patient, the prescription or medication order, or pump operating parameters into a device. It is important for the safety of the patient that the information is entered accurately and that programming errors are avoided. At the same time, it is important that the information be entered as quickly as possible so that delivery of the medication can begin, especially in emergency situations. Caregivers are often a scarce resource in the healthcare field. Thus, there is a compelling need to save the time of the user or caregiver when programming programmable medical devices such as medical pumps.

Conventional medical pumps have been provided with factory established limits in memory for certain pump operating parameters, for example the maximum and minimum volumetric delivery rates permissible.

More recently, as electronically erasable programmable read only memories (EEPROM) and flash memories have become more common, it has also become possible for a hospital or similar institution to establish or predefine on a remote computer a customized "drug library" comprising limits for various pump operating parameters and settings or patient characteristics based upon device type, drug and concentration or clinical care area, and then download the customized drug library to a medical pump. The drug library limits are useful in preventing parameter entry errors. However, the user enters a parameter and is subsequently advised via an error message or alarm if the entered value is outside the permissible range or limits.

Another problem that exists is that the parameters to be entered are often interrelated with other parameters. For example, volumetric rate multiplied by volume to be infused (VTBI) determines the duration or time the pump must run.

Alternatively the processor takes predetermined information to calculate dosage amounts, dosage rates and the like. A problem exists in that these processors having the predefined ranges will have a predefined range for both the data point entered and the final result or rate that is calculated using that data point. As a result, when an individual enters incorrect information into a device and an error message is communicated to the data entry person, that person does not know whether the data that was entered was entered incorrectly or if a calculated parameter falls outside a predefined range.

Additionally, a problem in the art occurs in that the predefined ranges do not take into account differences between patients and differences in the other medical parameters associated with the providing of the dosage of medicine. For example, an individual of greater size and weight may be able to receive and need to receive a greater dosage of medicine than a person of lesser height and weight wherein predefined limit ranges do not account for these variations.

Thus, a principal object of the present invention is to provide a system for guiding a user in the programming of a medical device.

Another object of the present invention is to provide a medication delivery system that ensures accuracy of entered data and yet allows the user to program the medical device with speed and flexibility.

Another object of the present invention is to provide a system in which the user of a medical device is advised in advance of entering a selected parameter about the existence of a valid input range for the selected parameter.

Another object of the present invention is to provide a system in which the user of a medical device is advised in advance of entering a selected parameter about the limits of a valid input range for the selected parameter, thus saving the user time and reducing user frustration involved with post-entry notification of invalid entries.

Another object of the present invention is to provide a system in which the limits of the valid input range for a parameter are rounded, truncated or ceiled.

Yet another object of the present invention is to provide a system that displays information that allows a user to pinpoint where errors within the device and computations occur.

Another object of the present invention is to provide a system that displays information that accounts for multiple variable medical parameters to provide an improved system.

These and other features, improvements and advantages will become apparent from the specification, drawings and claims.

BRIEF SUMMARY OF THE INVENTION

The present invention relates to medical pump systems and methods that provide advance guidance to a user regarding existence and limits of a valid input range for a pump programming parameter. The system includes an input device for entering a value of a pump programming parameter; a memory for storing constraints related to the pump programming parameter; and a processor in communication with the memory and the input device, the processor being operable to utilize the constraints to determine and generate a signal indicating whether a valid input range exists for a to-be-entered value of the pump programming parameter.

The medical pump system can further include an output device in communication with the processor to receive the signal indicating whether a valid input range exists for a to-be-entered value of the programmable variable and generate a notification to a user of the medical pump system. The notification can indicate that a valid range is absent, a valid range is present, and if a valid range is present can disclose its upper and lower limits to the user. In one embodiment, the output device is a display screen and the message is generated on the display screen.

The processor dynamically back calculates and generates a signal indicative of a valid range for a to-be-entered pump programming parameter based upon constraints such one or more predetermined equations relating the to-be-entered pump programming parameter to other pump programming parameters that may or may not have been entered already, medical device capabilities, and patient medical information.

BRIEF DESCRIPTION OF THE DRAWINGS

FIG. 2 is a screen shot of a medical device according to the present invention;

DETAILED DESCRIPTION OF THE PREFERRED EMBODIMENT

The present invention will be described as it applies to its preferred embodiment. It is not intended that the present invention be limited to the preferred embodiment. It is intended that the invention cover all modifications and alternatives that may be included within the scope of the appended claims.

Figure 1:
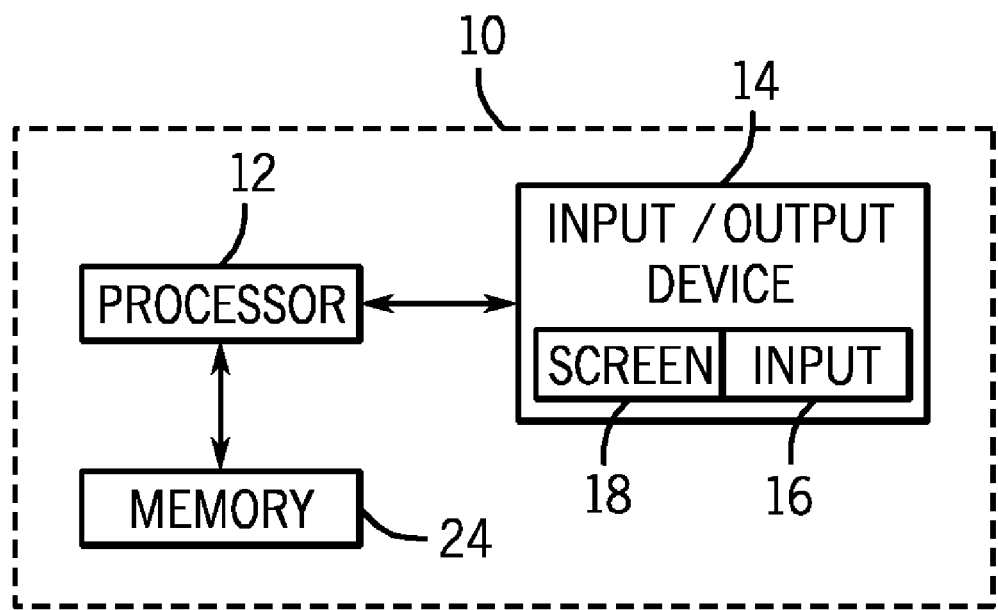
FIG. 1 is a schematic diagram of a medical device according to the present invention.

FIG. 1 is a schematic diagram of a system that has a medical device 10 therein. FIG. 1 illustrates several functional components of the medical device 10 for implementing the present invention. Those of ordinary skill in the art will appreciate that the device 10 includes many more components than those shown in FIG. 1. However, it is not necessary that all these components be shown in order to disclose an illustrative embodiment for practicing the present invention.

In the context of the present invention, the term "medical device" includes without limitation a device that acts upon a cassette, reservoir, vial, syringe, or tubing to convey medication or fluid to or from a patient (for example, an enteral pump, a parenteral infusion pump, a patient controlled analgesia (PCA) or pain management medication pump, or a suction pump), a monitor for monitoring patient vital signs or other parameters, a diagnostic device, or the like.

For the purpose of exemplary illustration only, the medical device 10 is disclosed as an infusion pump. More particularly, the medical device 10 can be a single channel infusion pump, a multi-channel infusion pump, or some combination thereof.

The following definitions are not intended to be limiting, but are included below to aid one skilled in the art in understanding this disclosure.

"Patient medical information" as used herein means information about a patient, including but not limited to weight, height, body surface area (BSA), known drug allergies or tolerances or permissible levels, name, or patient ID. It will be appreciated by one skilled in the programmable medical pump art from the description herein that patient medical information can be input and stored at the pump using the input device, received by the pump from a computer or storage device connected wirelessly or by hard wire to the pump, or received as part of a drug library by the pump from a computer or storage device connected wirelessly or by hard wire to the pump.

"Medication information" as used herein means information about the medication to be administered to a patient, including but not limited to drug name, drug alias, drug ID, drug trademark, drug generic name, concentration, drug amount, drug units, container volume, or dosing units.

"Pump operating parameters" as used herein means input parameters or information that affects the behavior of a pump and delivery of medication by it, including but not limited to dose, dosage, dose rate, dose amount, rate, time, volume infused or volume to be infused (VTBI).

"Pump programming parameters" as used herein broadly includes parameters that are programmed into a pump by the user or otherwise and may include one or more of pump operating parameters, medication information, patient medical information or calculations based thereon or combinations thereof. Pump programming parameters may have hard and/or soft limits applied to them through a factory or hospital customizable drug library that is resident in the device or electronically downloadable thereinto.

"Medical device capabilities" as used herein means capabilities or limitations on a pump or infuser as determined by the manufacturer's recommendations, hardware, software, administration set, primary/secondary line considerations, or other constraints. In one example, the infuser may have a minimum and/or maximum rate at which it can deliver. In another example, primary and secondary lines may have predetermined interrelated maximums so as to avoid creating any vacuum or inadvertent flow problems. By way of example only, the primary line maximum rate could be 1000 ml/hr while the secondary line rate could be limited to a maximum of 500 ml/hr.

With reference to FIG. 1 the medical device 10 includes a processor 12 that performs various operations described in greater detail below. An input/output device 14 allows the user to receive output from the medical device 10 and/or enter information into the medical device 10. Those of ordinary skill in the art will appreciate that input/output device 14 may be provided as single devices such as a separate input device 16 and an output device 18 that in one embodiment is a display device such as an output screen and in another embodiment is a voice command that states ranges or outputs. In another embodiment the input device 16 is a touch screen.

In an alternative embodiment the medical device is a medication management system (MMS) and the input/output device 14 is a drug library editor as described in U.S. Publication No. 2005/0144043 and that reference is incorporated in full in this application. In this embodiment input 16 communicates with a MMU (Medication Management Unit) to assist in processing drug orders for delivery through the MMU. The input device 16 can be any sort of data input means, including those adapted to read machine readable indicia such as barcode labels; for example a personal digital assistant (PDA) with a barcode scanner. Alternatively, the machine readable indicia may be in other known forms, such as radio frequency identification (RFID) tag, two-dimensional bar code, ID matrix, transmitted radio ID code, human biometric data such as fingerprints, etc. and the input device 16 adapted to "read" or recognize such indicia. The input device 16 can be a separate device from the medical device 10; alternatively, the input device 16 communicates directly with the medical device 10 or may be integrated wholly or in part with the medical device.

A memory 24 communicates with the processor 12 and stores code and data necessary for the processor 12 to perform the functions of the medical device 10. More specifically, the memory 24 stores multiple programs and processes formed in accordance with the present invention for various functions of the medical device 10.

Referring to FIGS. 2-9 various screen shots of output device 18 are shown for presentation of data to a user that is entering data into a medical device 10. In one embodiment the output device 18 is an output screen and in another embodiment output device 18 is a touch screen display and input device. The output device 18 is in the context of an infusion pump; however, this is for exemplary purposes only. Other instruments may incorporate aspects of the invention and generate audio output or present a graphic display to communicate data.

As shown, the output device 18 provides several entry points wherein patient medical information or medication information 102 and pump programming parameters 100 may be entered. Specifically, patient medical information such as a patient's weight 104, height 106 or BSA (body surface area) 108 may be entered. Additionally, pump operating parameters 102 such as dose 110, rate 112, VTBI (volume to be infused) 114, time 116 and dose amount 118 may be entered using a numerical key pad 120 that allows input of numerals 124 on the key pad 120. The key pad 120 additionally has a CANCEL button 126 if a user does not desire to enter information, a CLEAR button 128 to clear an input and an ENTER button 130 to enter an amount. Thus, a numerical value can be given using the key pad 120 to provide a numerical value for the height, weight or BSA of the patient or the dose rate, dose amount, rate, VTBI or time to be provided. Additionally, on the output device 18 is a text box 134 wherein a message 136 can be provided to the user regarding the data to be entered or the entered data provided. Specifically, the text box 134 can provide whether the entered pump programming parameters are proper. The text box 134 can also provide the user advance guidance on the valid range of values that can be entered, or whether a valid range exists.

Figure 3:
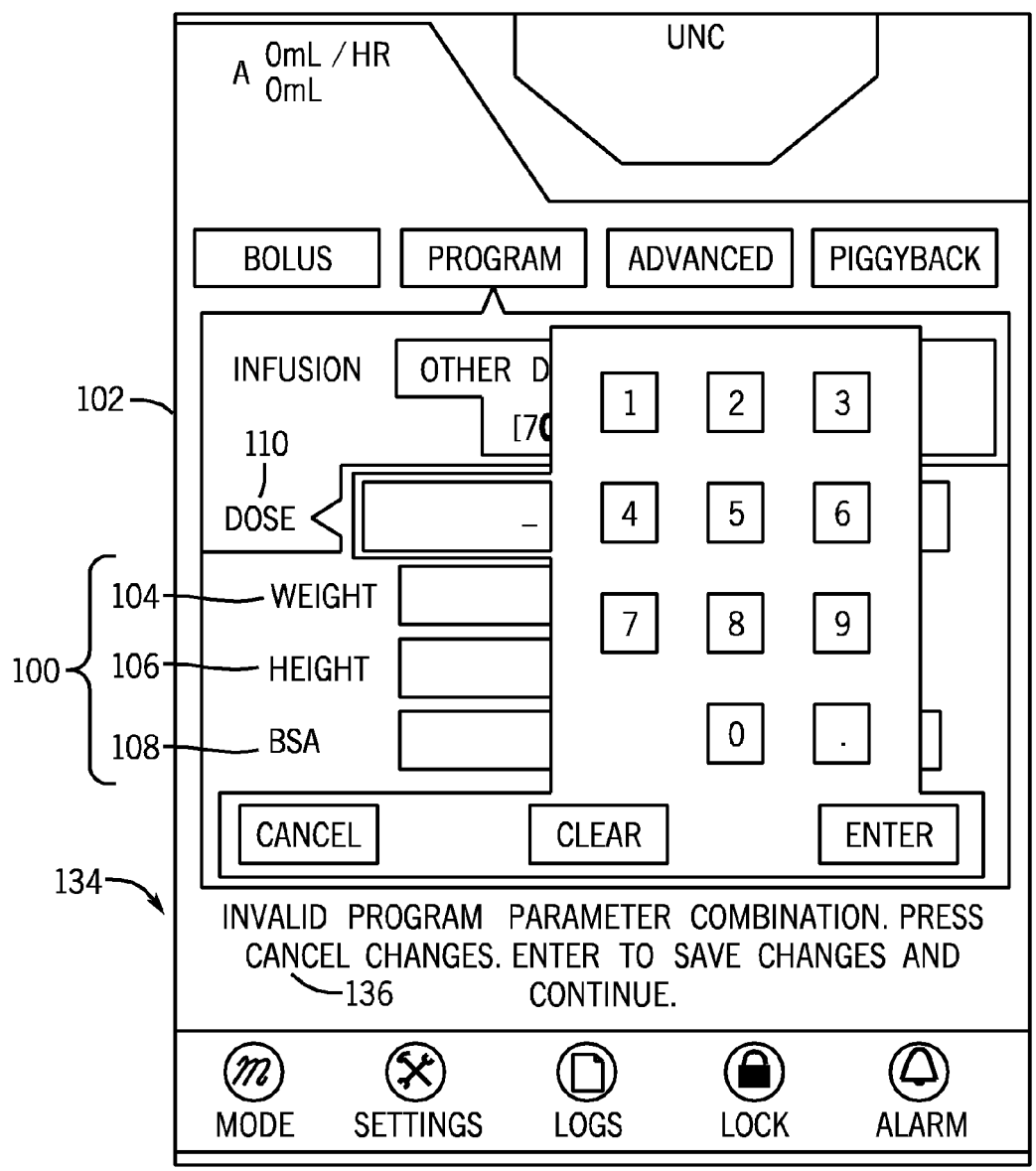
FIG. 3 is a screen shot of a medical device according to the present invention.
Figure 4:
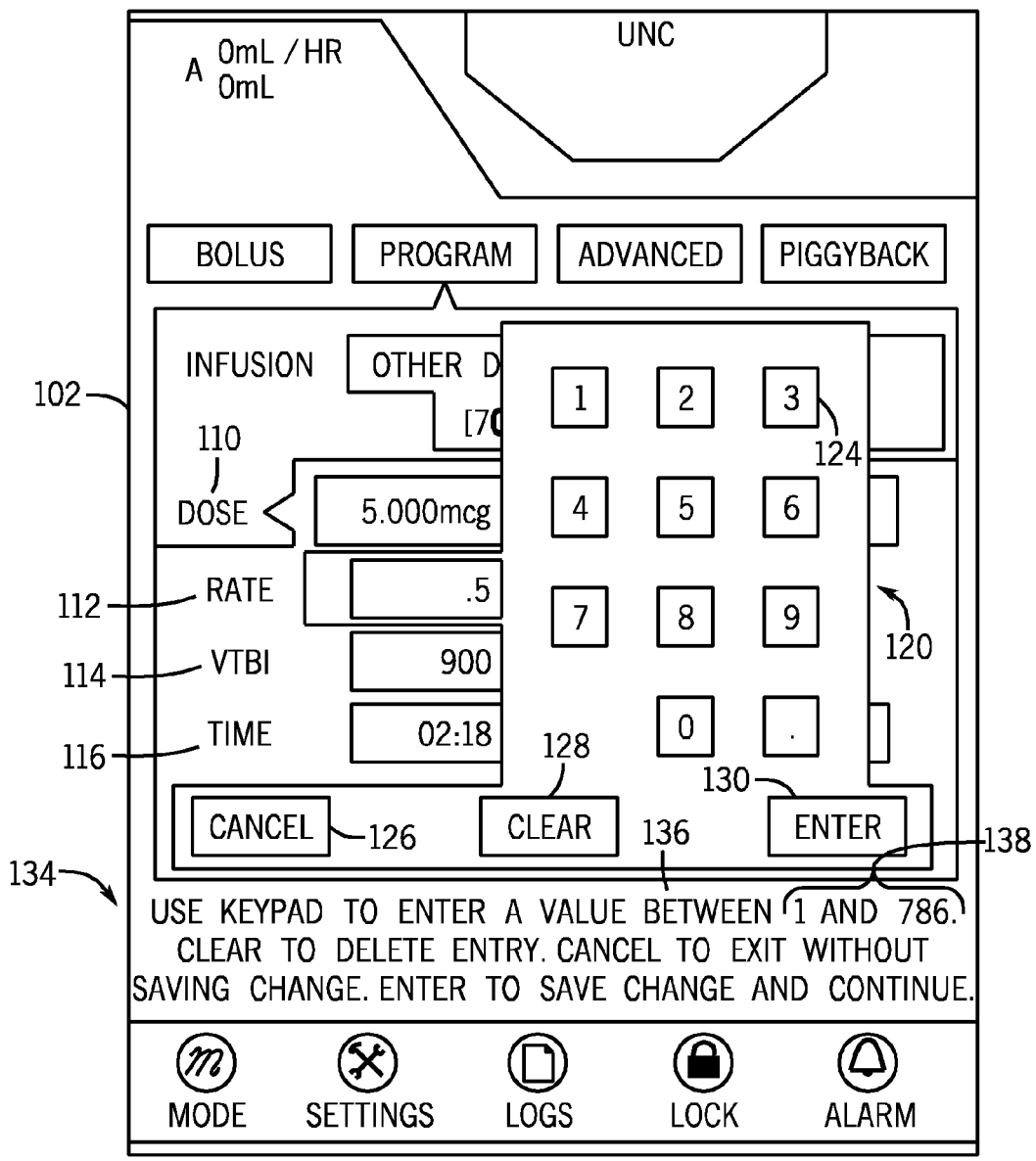
FIG. 4 is a screen shot of a medical device according to the present invention.
Figure 5:
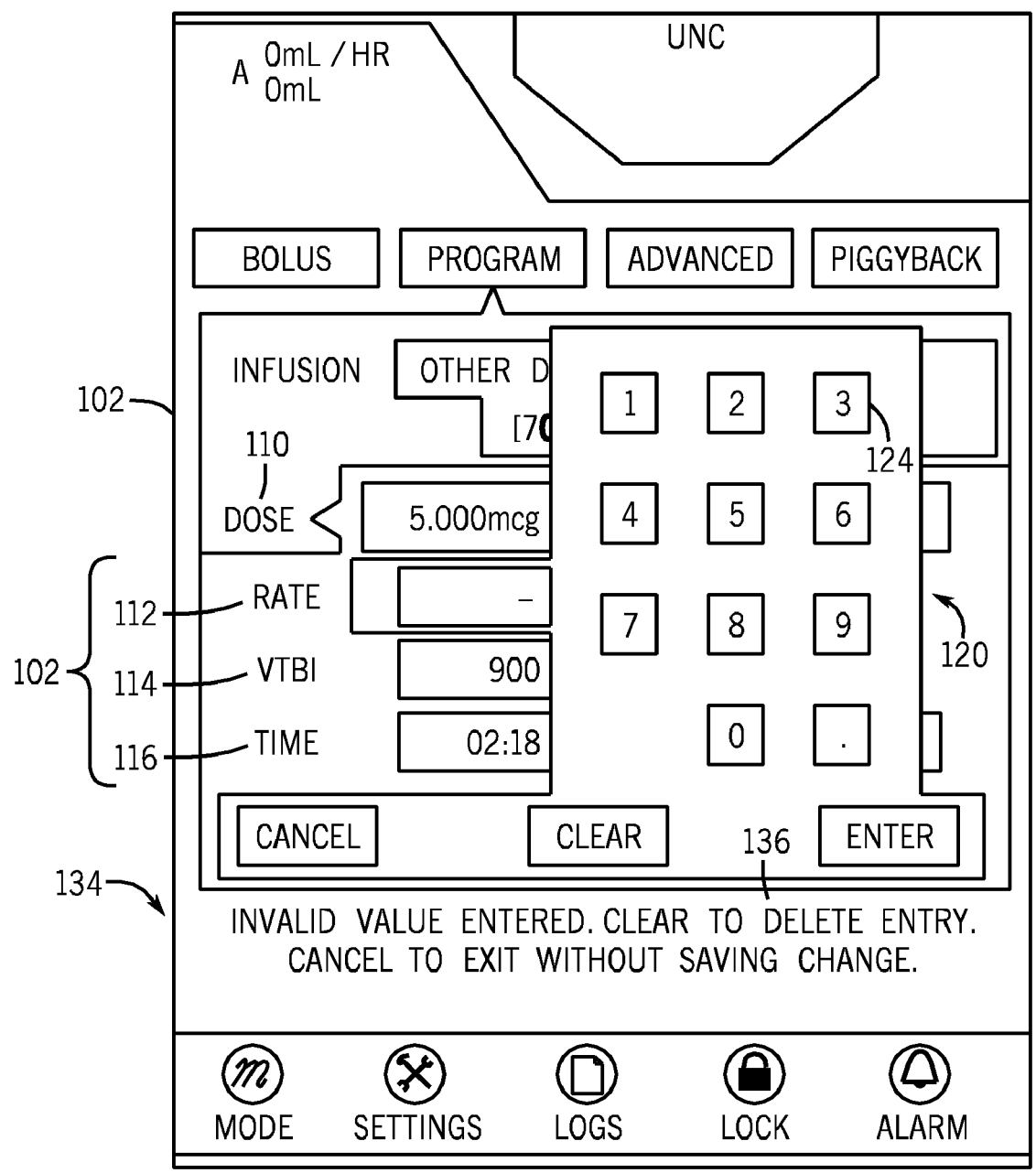
FIG. 5 is a screen shot of a medical device according to the present invention.

The message 136 provided depends upon the data entered into the medical device 10. For example, the message can indicate that an invalid program parameter combination is entered (FIG. 3). This indicates to a user that for the parameters selected there is no valid range that can be calculated. Alternatively, if a valid range 138 exists (FIG. 4) this valid range is displayed. Whereas if the data point entered is invalid the message 136 indicates an invalid value has been entered (FIG. 5).

Figure 6:
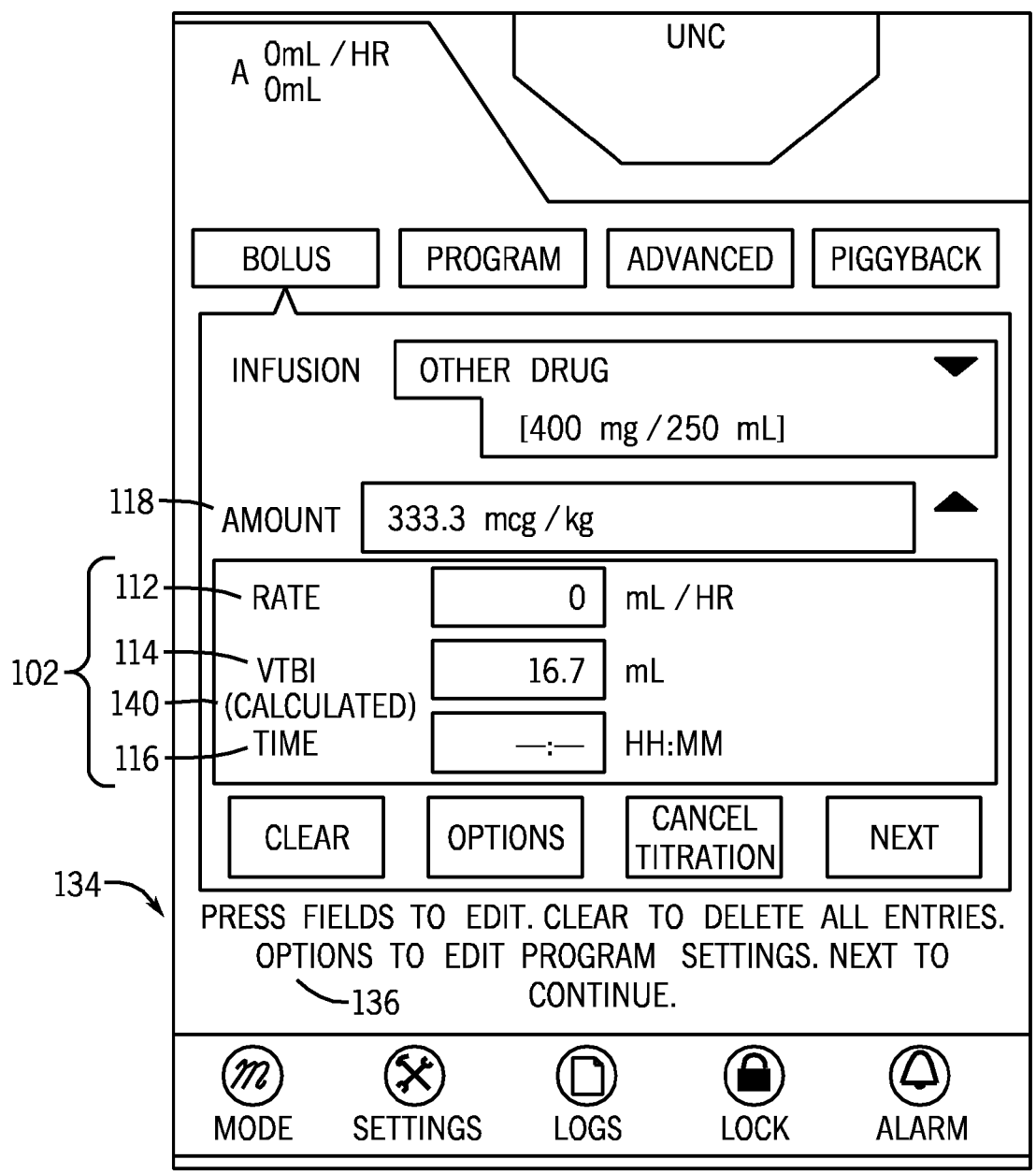
FIG. 6 is a screen shot of a medical device according to the present invention.
Figure 7:
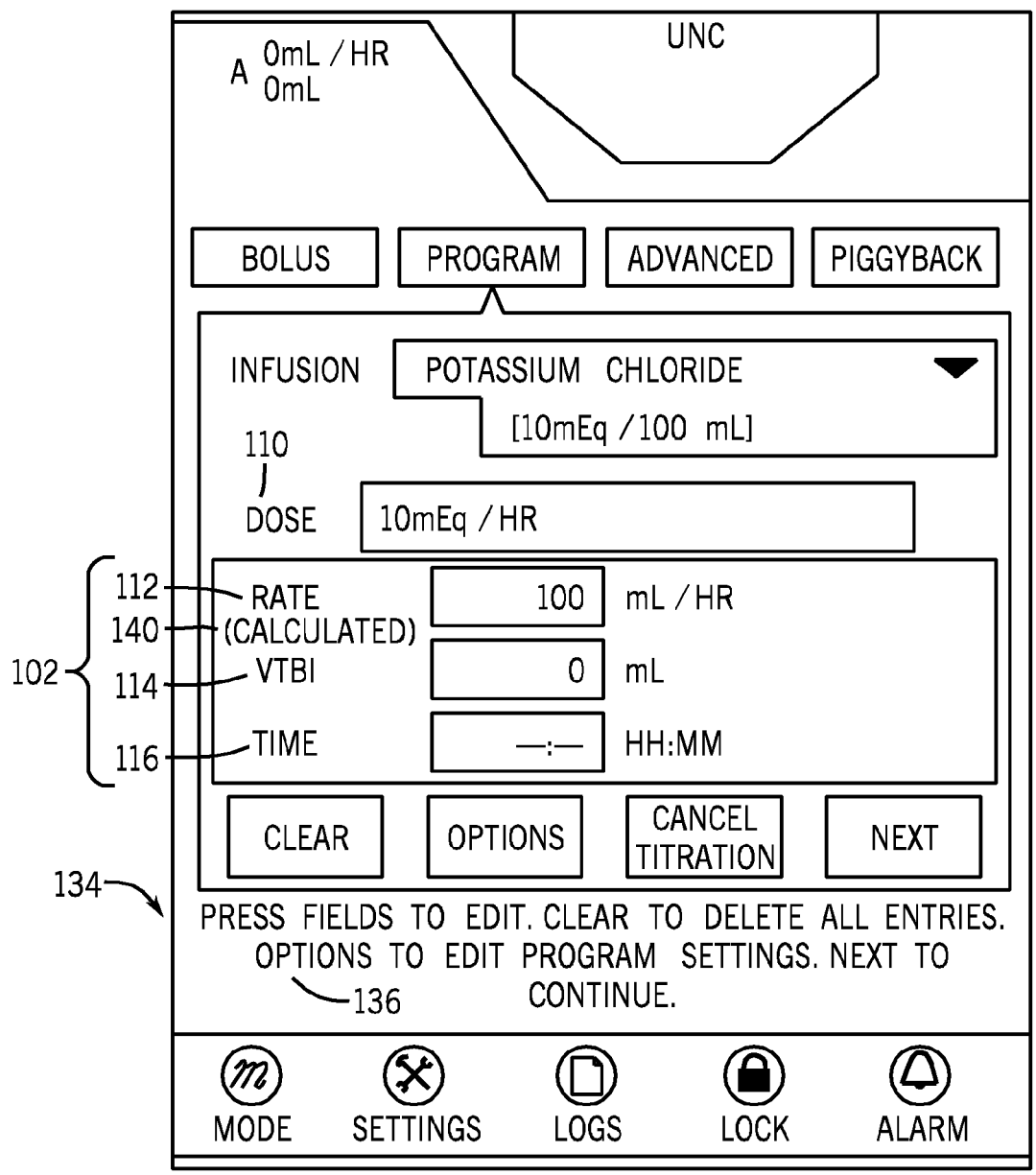
FIG. 7 is a screen shot of a medical device according to the present invention.
Figure 8:
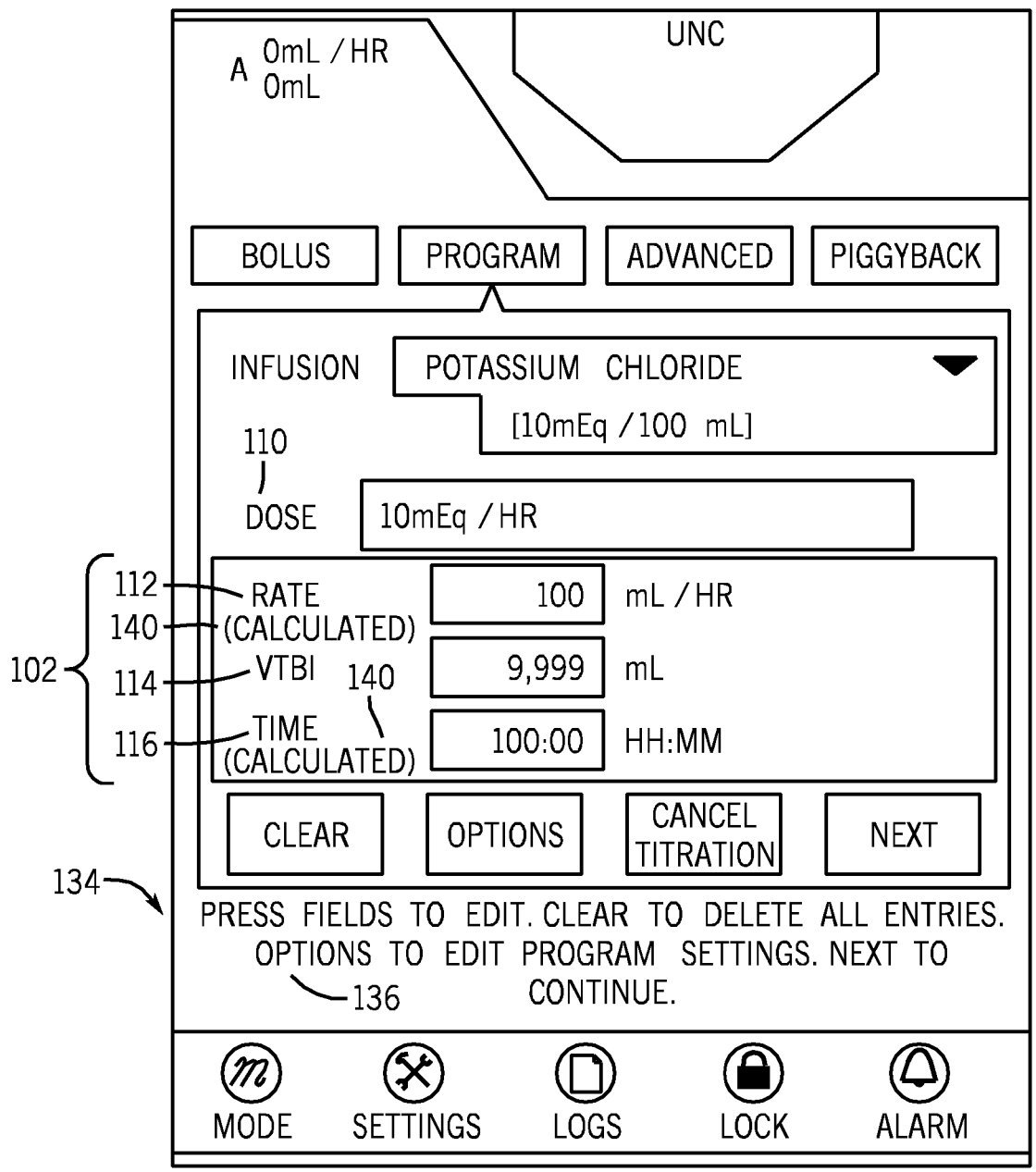
FIG. 8 is a screen shot of a medical device according to the present invention.
Figure 9:
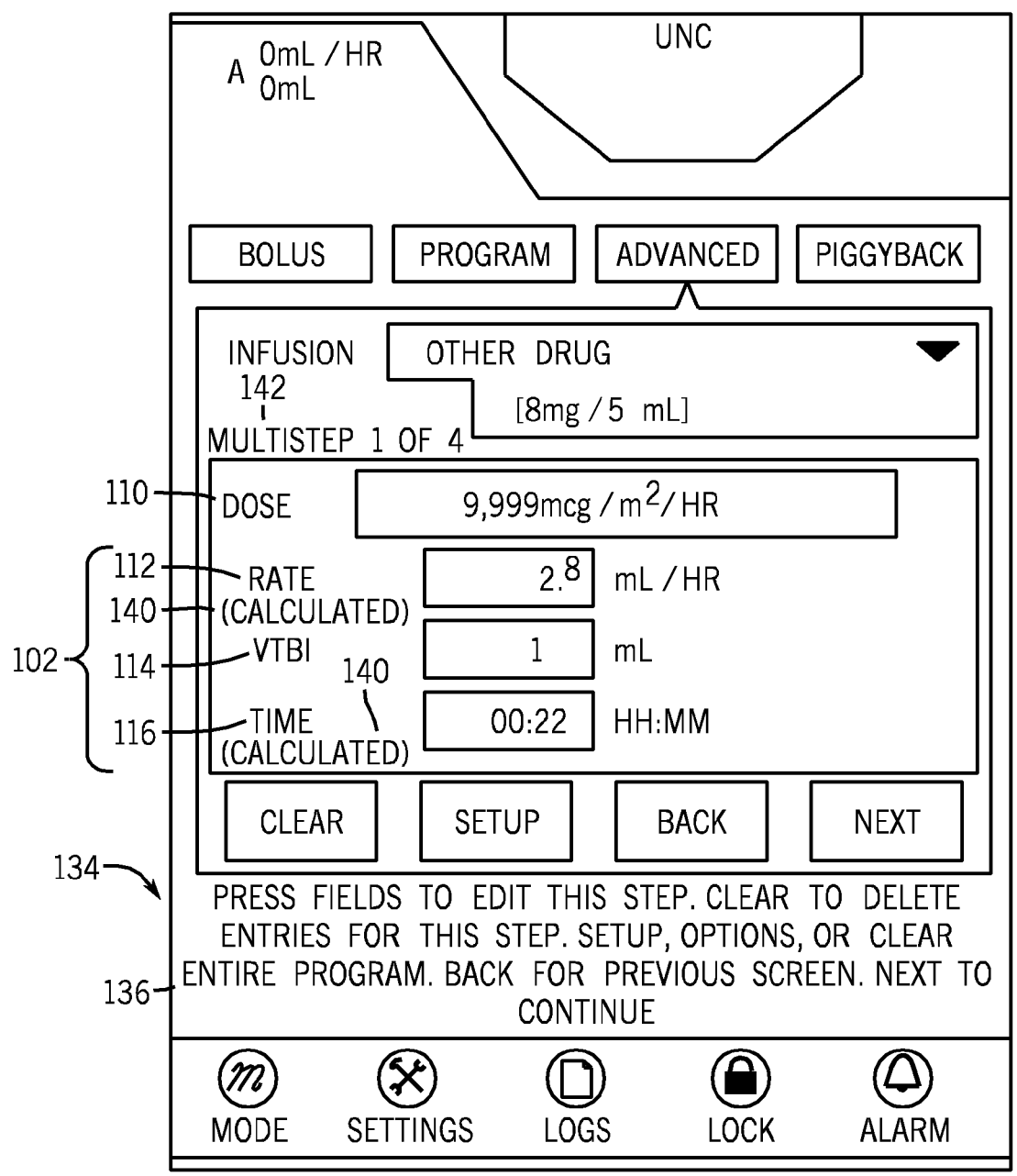
FIG. 9 is a screen shot of a medical device according to the present invention.

As shown in FIGS. 6-8 the output device 18 additionally indicates when parameters have been calculated, as indicated by reference numeral 140. As also shown multiple parameters may be calculated and displayed as will be discussed. The output device also provides an option for multi step infusion processes 142 as provided in FIG. 9. FIGS. 2-9 are examples of several different outputs an output device 18 may present to a user.

By back calculating equations used in the system the user can be presented with a valid range 138 of values that may be entered (FIG. 4) or if there is no valid value to be entered (FIG. 3). There are two different scenarios for these back calculations: (1) there are no other parameters entered; or (2) other parameters are already entered.

In the first scenario minimum and maximum ranges for all patient medical information and parameters are used to back calculate the range for each piece of patient medical information and/or parameters currently being adjusted (about to be entered). In the second scenario the entered values for the information and/or parameters that are not affected by modifying the current parameter, and the range of information and/or parameters which are affected by a modification to the current information and/or parameters are used to back calculate the range of the information and/or parameter currently being adjusted (about to be entered). Below is an illustration of these two scenarios using rate, VTBI, and time dependency:

$$\text{Rate} = VTBI/\text{time}$$

Each parameter (rate, VTBI, and time) has its own minimum and maximum value which may be configurable.

When no other parameters that have already been entered, if the user wants to enter a new rate 112, the valid range for rate 112 would be calculated as follows:

$$\text{Rate Min} = VTBI\text{ Min}/\text{Time Max}$$

$$\text{Rate Max} = VTBI\text{ Max}/\text{Time Min}$$

When there are other parameters such as VTBI already entered, if the user wants to enter a new rate 112, the time is recalculated such that the valid range for rate 112 would be calculated as follows:

$$\text{Rate Min} = VTBI/\text{Time Max}$$

$$\text{Rate Max} = VTBI/\text{Time Min}$$

The possible values to be entered are also dependent upon the precision in which the user enters values. Depending on the precision/exactness of the internal math being used, the valid range calculation should use either rounding (may be used on both the upper and lower valid range), truncating (may be used on the upper valid range), or ceiling (may be used on the lower valid range) of the adjusted valid range values when calculating the range to be used.

Once the adjusted valid range has been calculated, the first time using rounding, the just calculated minimum and maximum values are used in the original equation to calculate what should be calculated when modifying the current parameter. If the calculated value ends up outside its valid range values (which may be either the machine limitations or adjusted valid ranges themselves) truncation for the upper valid range or ceiling for the lower valid range may be used.

To illustrate this with an example, if the machine limitations for rate 112 are 10 ml/hr-500 ml/hr and the user is able to program rate values 112 in one decimal place precision (0.1 ml/hr increments) then if rate (MIN) is calculated to 15.015 the value could be ceiled to 15.1. Meanwhile, if rate (MAX) value was calculated to 85.4996 the rate MAX value should be truncated to 85.4. If the rate (MIN) value and the rate (MAX) values are allowed to be entered as the rounded values 15.0 and 85.5 the result would have been that the calculated time would have ended up outside the machine limitations.

Flow equations are being used in the system during programming, and the same method can be reapplied multiple times each modifying a weight which is part of a BSA (body surface area) calculation, which is part of a dose calculation, which ultimately recalculates time 116. Once the valid ranges for each of the parameters are calculated, the ranges should be compared against the machine/configurable limitations for the current information and/or parameter. The most stringent range is what should be used.

FIGS. 10-44 are a plurality of flowcharts that show the system processes used in order for the processor 12 to calculate valid ranges, determine what those ranges are (if they exist), and whether entered information or parameters fall outside of said range. If no valid range exists or the entry is outside of the valid range an indication of that fact is generated to the user. If a valid range exists, the valid range can also be indicated to the user prior to entry of the parameter. In one embodiment, the indication to the user is a user message 136 that is displayed on the display 18. Thus, each flowchart represents a different process that can be involved in performing these functions.

Figure 10:
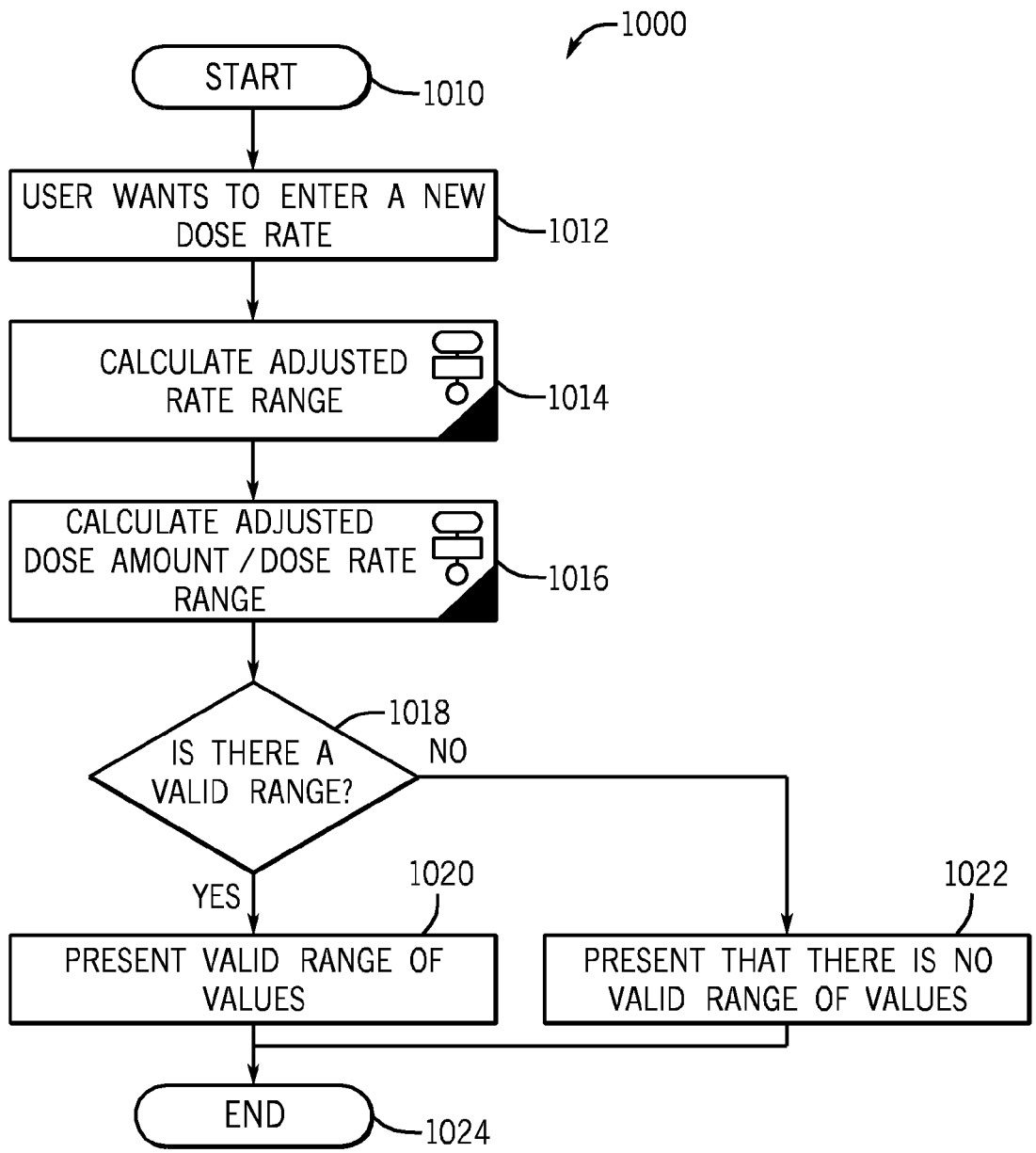
FIG. 10 is a flowchart of a process that calculates and displays the adjusted valid range for dose rate before a dose rate is entered.
Figure 24A:
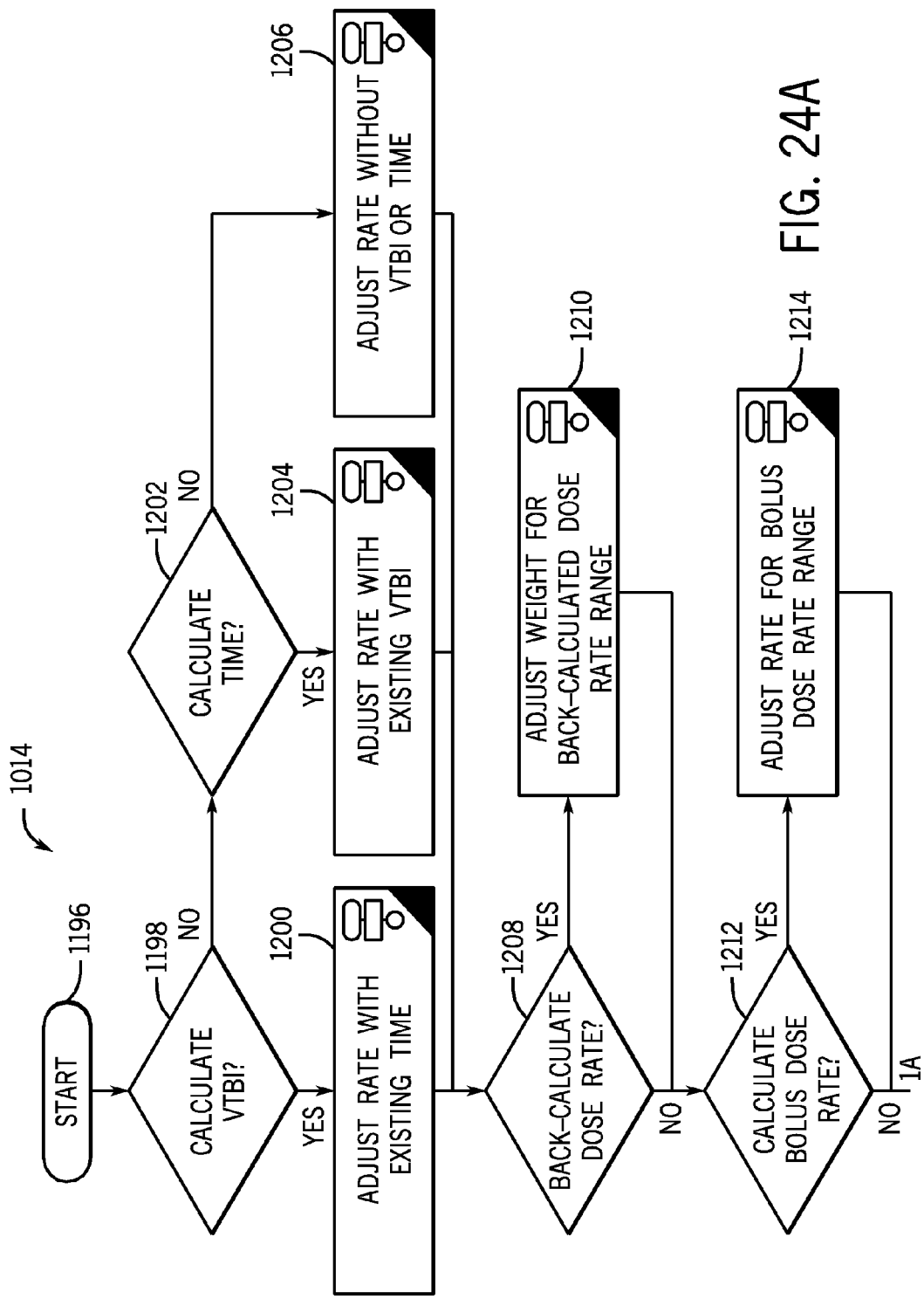
FIG. 24A is the initial portion of a flowchart of a process that calculates the adjusted valid range for rate.
Figure 24B:
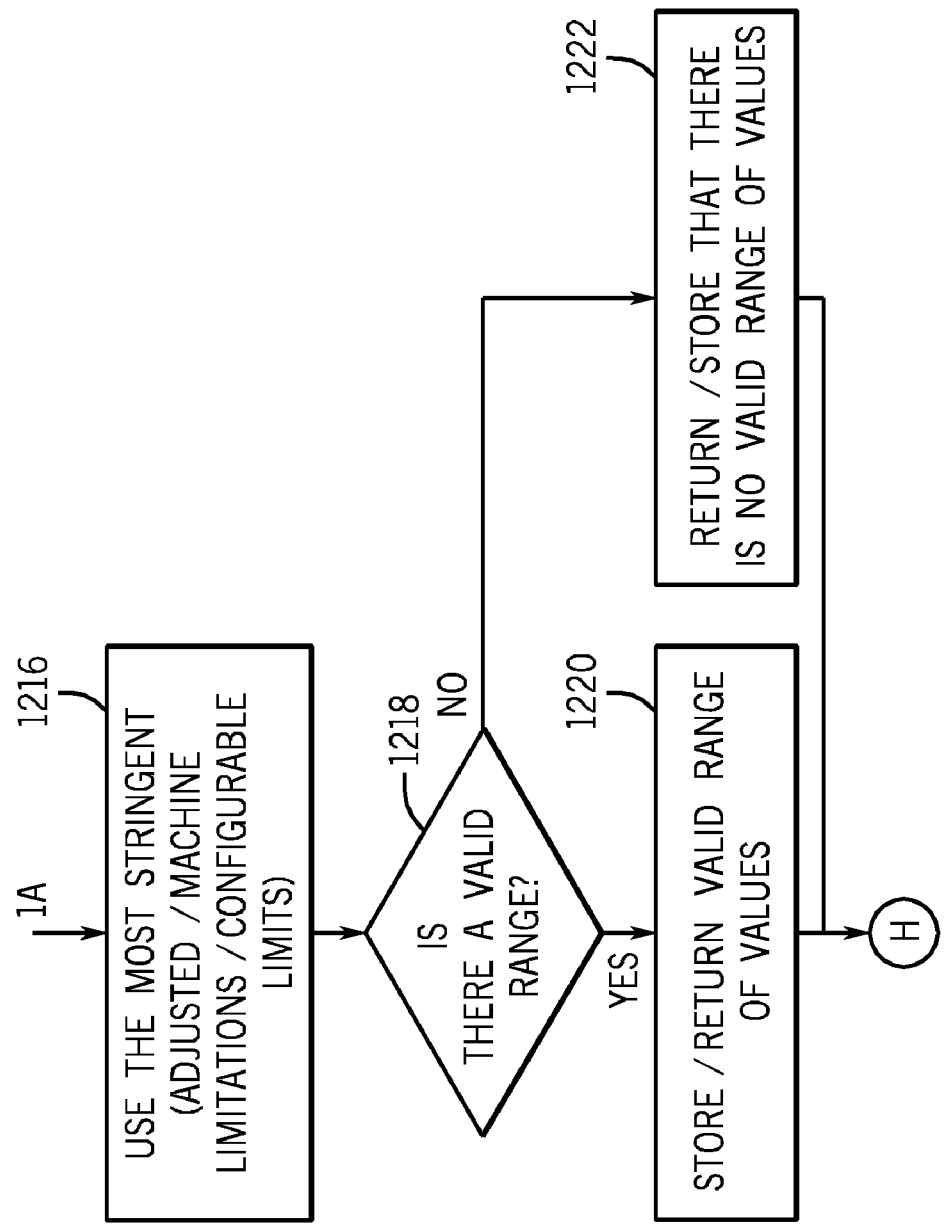
FIG. 24B is a continuation of the flowchart of FIG. 24A and shows the remaining portion of a process that calculates the adjusted valid range for rate.

Specifically, FIG. 10 shows a process 1000 for calculating and displaying an adjusted valid range for the dose rate before a dose rate is entered. After starting at step 1010 the processor 12 detects that the user wants to enter a new dose rate as shown at step 1012 in which time the processor, based upon the parameters already entered into the processor, calculates an adjusted valid range for rate at step 1014. A process that provides for this calculation is seen in FIGS. 24A and 24B and will be discussed.

Figure 20A:
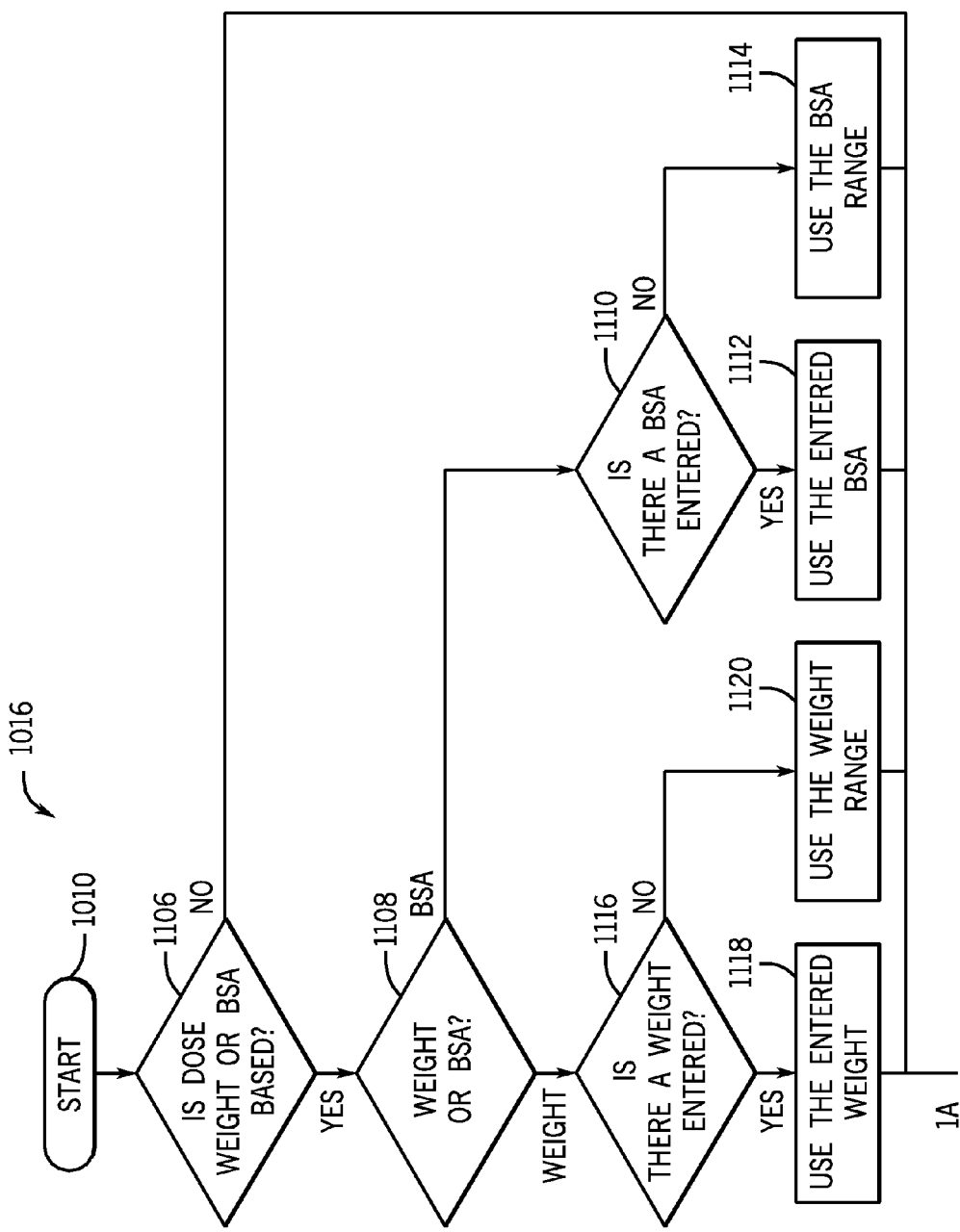
FIG. 20 is a flowchart of a process that calculates the adjusted valid range for dose rate or dose amount.
Figure 20B:
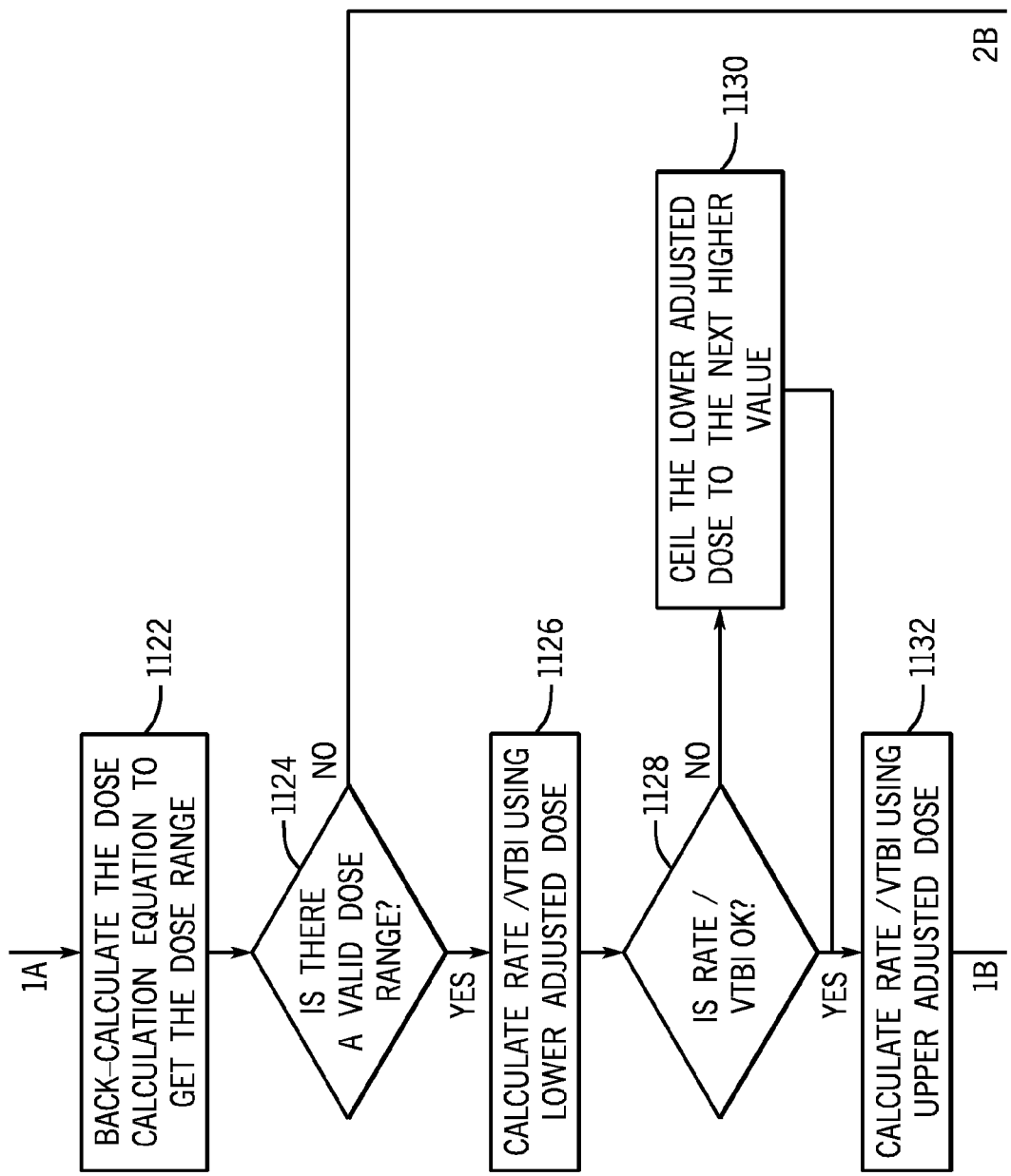

Once an adjusted valid range for the rate is calculated at step 1014 the processor 12 then at step 1016 calculates the adjusted valid range for the dose rate or dose amount (see FIGS. 20A, 20B and 20C for greater detail on step 1016). Dose rate is a term in the infusion device art that refers to delivering an amount of medication over a given unit of time. For example, a dose rate can be expressed in units including but not limited to mcg/hr or units/kg/day. Dose amount is a term in the infusion device art that refers to delivering an amount of medication, without regard to time, usually in a bolus. For example, a dose amount can be expressed in units including but not limited to mcg or units/kg. At step 1018 a determination is made whether there is a valid range for a new dose rate or dose amount. If there is a valid range then at step 1020 this valid range of values is presented in the text box 134 on the output device 18 (FIG. 4) to alert a user what values may be entered. If there is not a valid range of values available then at step 1022 the processor 12 displays in the text box 134 that there is no valid range of values that may be entered. Thus, the process is ended at step 1024.

Figure 11:
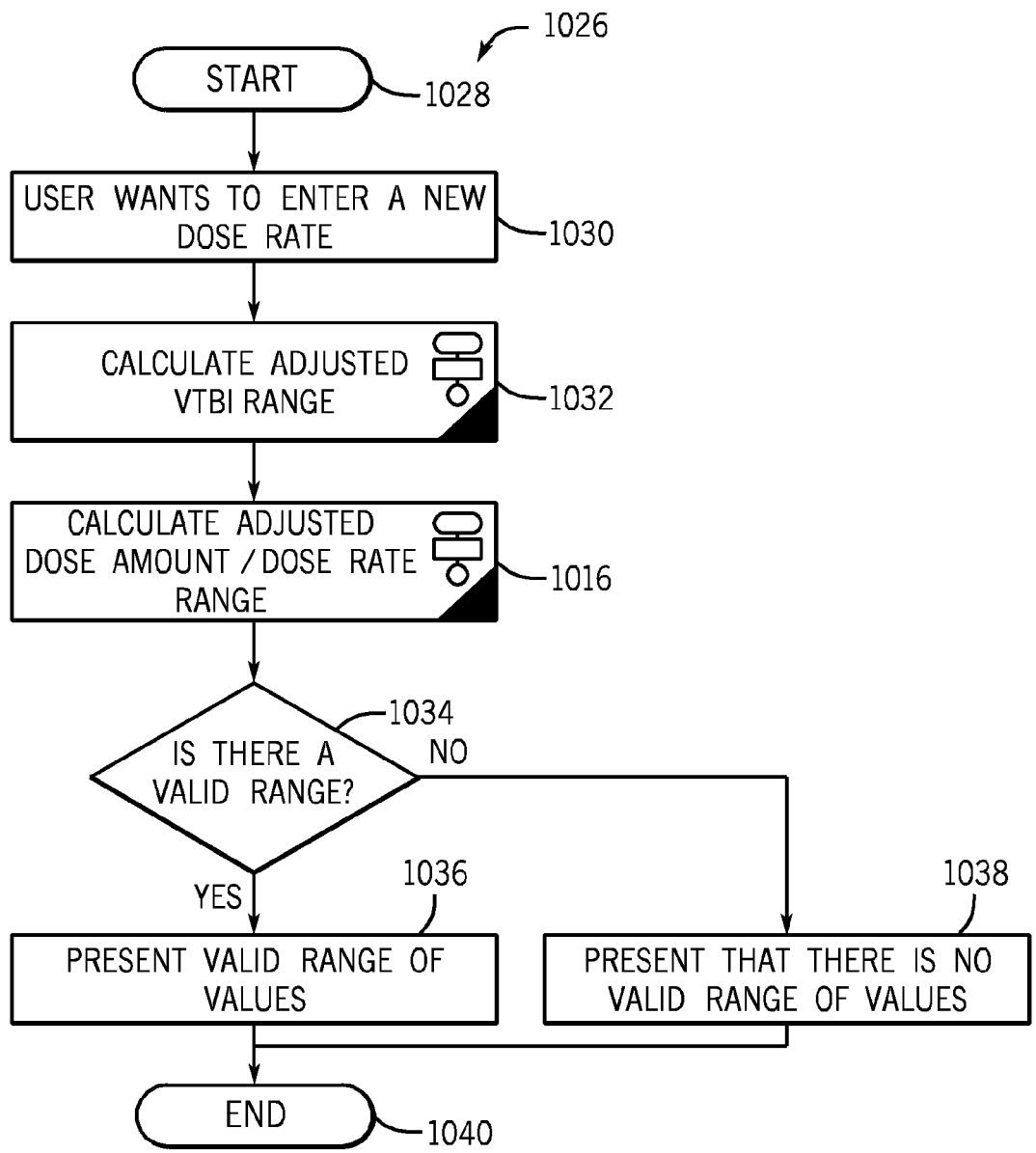
FIG. 11 is a flowchart of a process that calculates and displays the adjusted valid range for dose amount before a dose amount is entered.
Figure 25A:
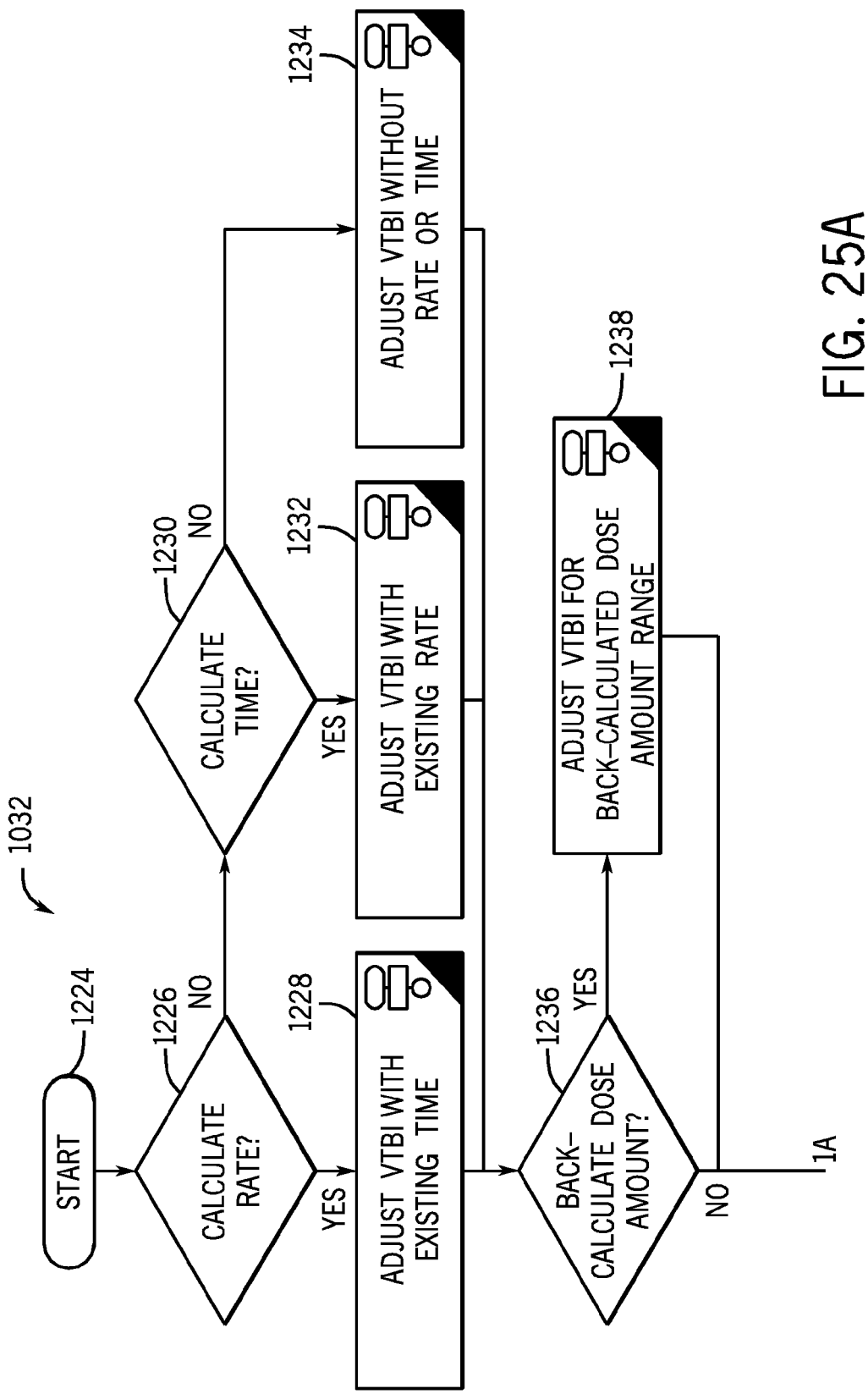
FIG. 25A is the initial portion of a flowchart of a process that calculates the adjusted valid range for VTBI.
Figure 25B:
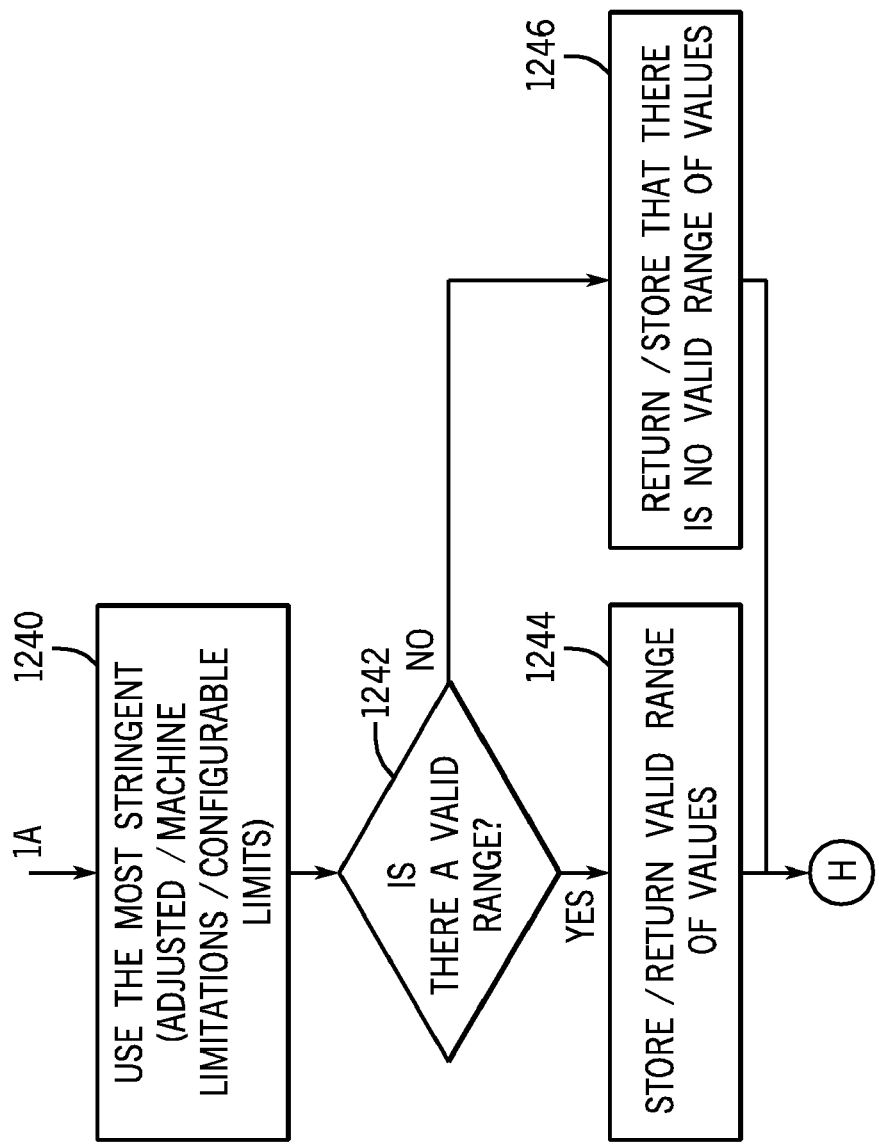
FIG. 25B is a continuation of the flowchart of FIG. 25A and shows the remaining portion of a process that calculates the adjusted valid range for VTBI.

FIG. 11 shows a process 1026 for calculating and displaying the adjusted valid range for a dose amount before a dose amount is entered. At step 1028 the process is started wherein the user desires to enter a new dose amount at step 1030. At this time, the processor 12 calculates an adjusted valid range for VTBI (volume to be infused) at step 1032 (FIGS. 25A and 25B). After calculating an adjusted valid range for the VTBI the processor 12 then calculates an adjusted valid range for dose amount at step 1016 (shown in greater detail in FIGS. 20A, 20B and 20C). Then at step 1034 a determination is made whether there is a valid range. If there is a valid range at step 1034 the processor 12 presents the valid range of values in the text box 134 at step 1036 and if there is not a valid range of values the processor 12 displays as such in the text box 134 of output device 18 as indicated by step 1038. At this point the process has ended at step 1040.

Figure 12:
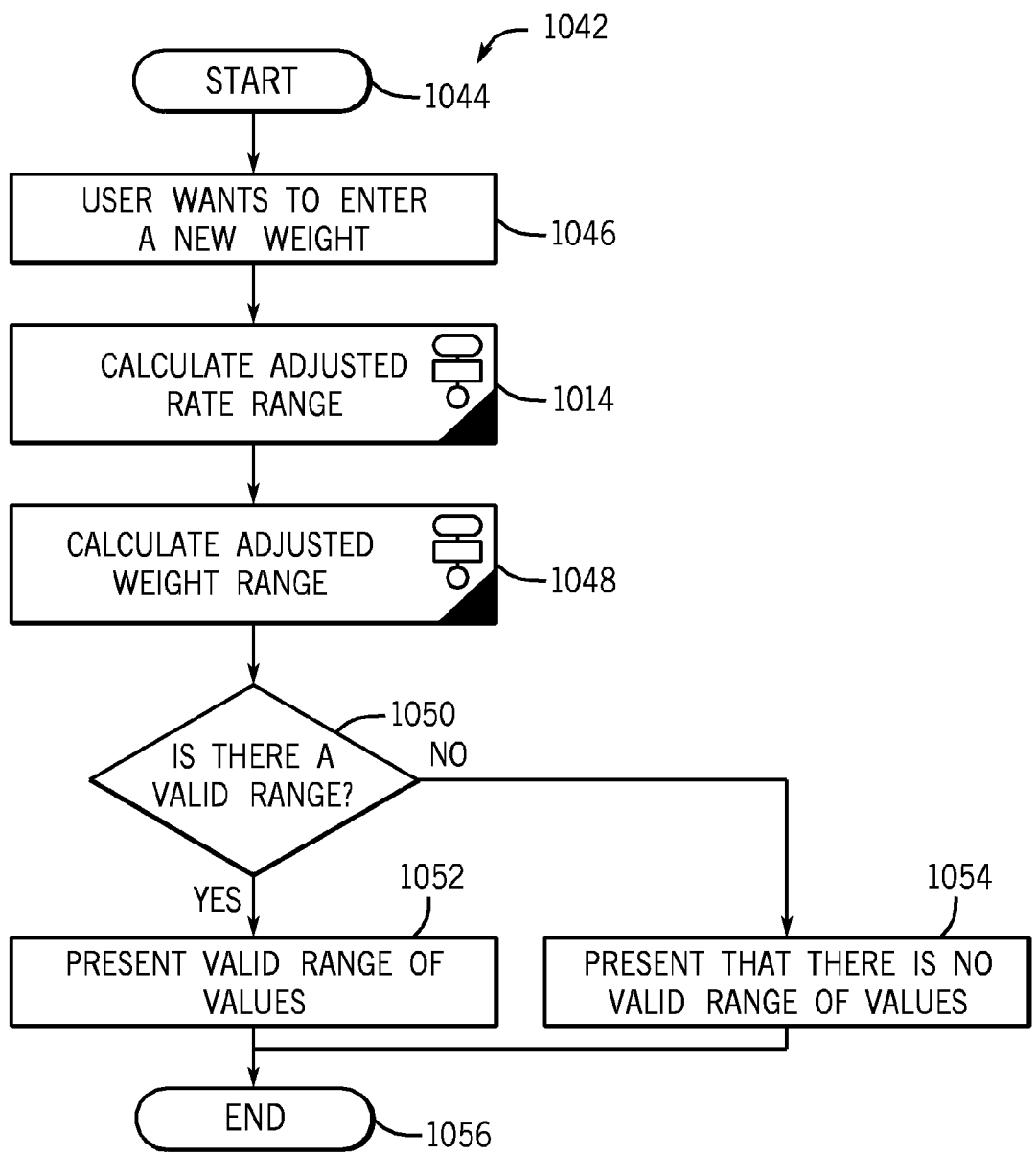
FIG. 12 is a flowchart of a process that calculates and displays the adjusted valid range for weight before a weight is entered when weight is part of a dose rate.
Figure 21:
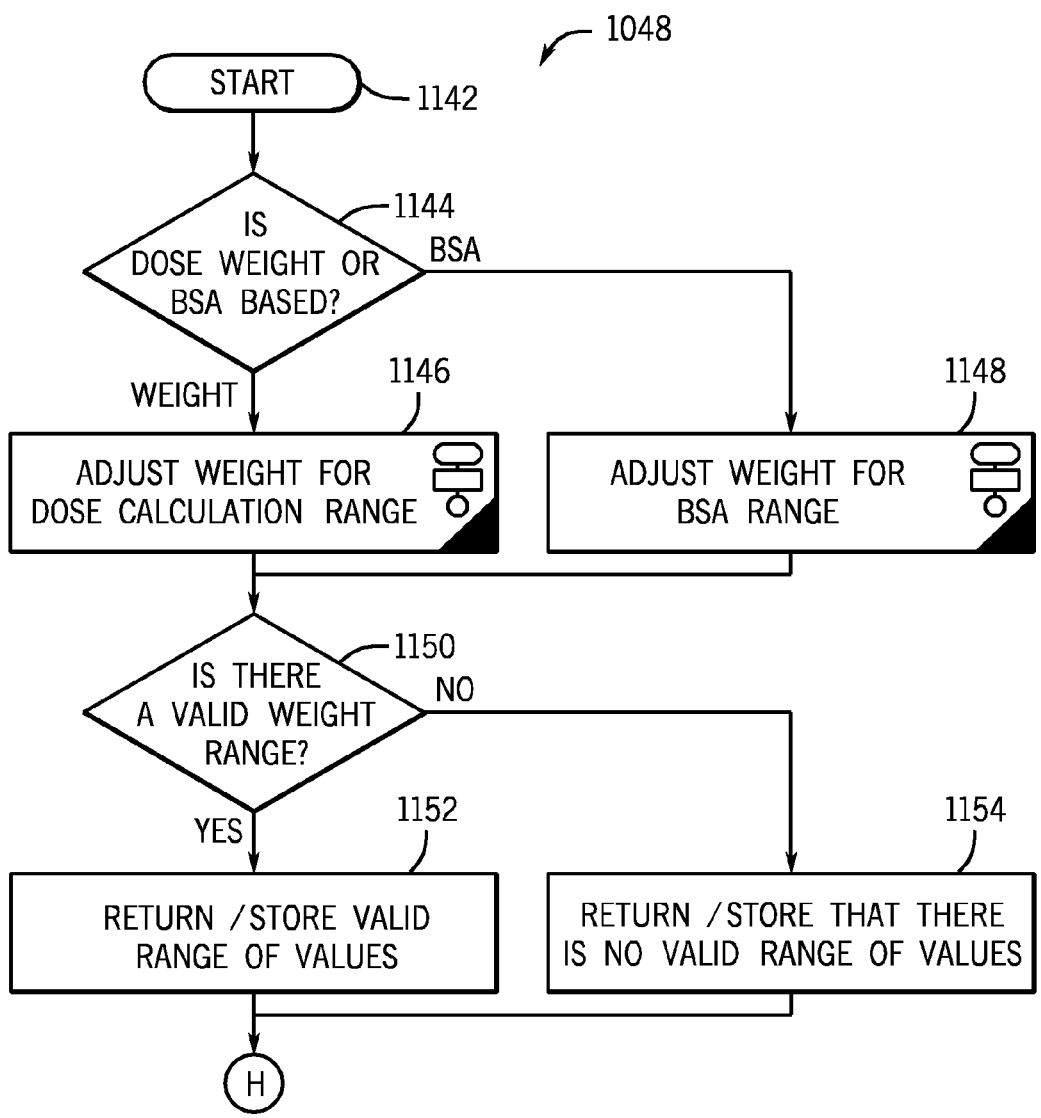
FIG. 21 is a flowchart of a process that calculates the adjusted valid range for weight.

FIG. 12 shows a process 1042 for calculating and displaying the adjusted valid range for a weight before a weight is entered when weight is part of a dose rate. Specifically, after the start step 1044 a user decides to enter a new weight at step 1046. The processor 12 then calculates an adjusted valid range for rate at step 1014 (shown in FIGS. 24A and 24B). After doing so, the processor 12 calculates an adjusted valid range of weight at step 1048 (FIG. 21). Then at step 1050 a determination is made whether a valid range exists and if a valid range exists, this range is displayed at step 1050 whereas if a valid range does not exist this is displayed as indicated by step 1054, either of which provides an end at step 1056.

Figure 13:
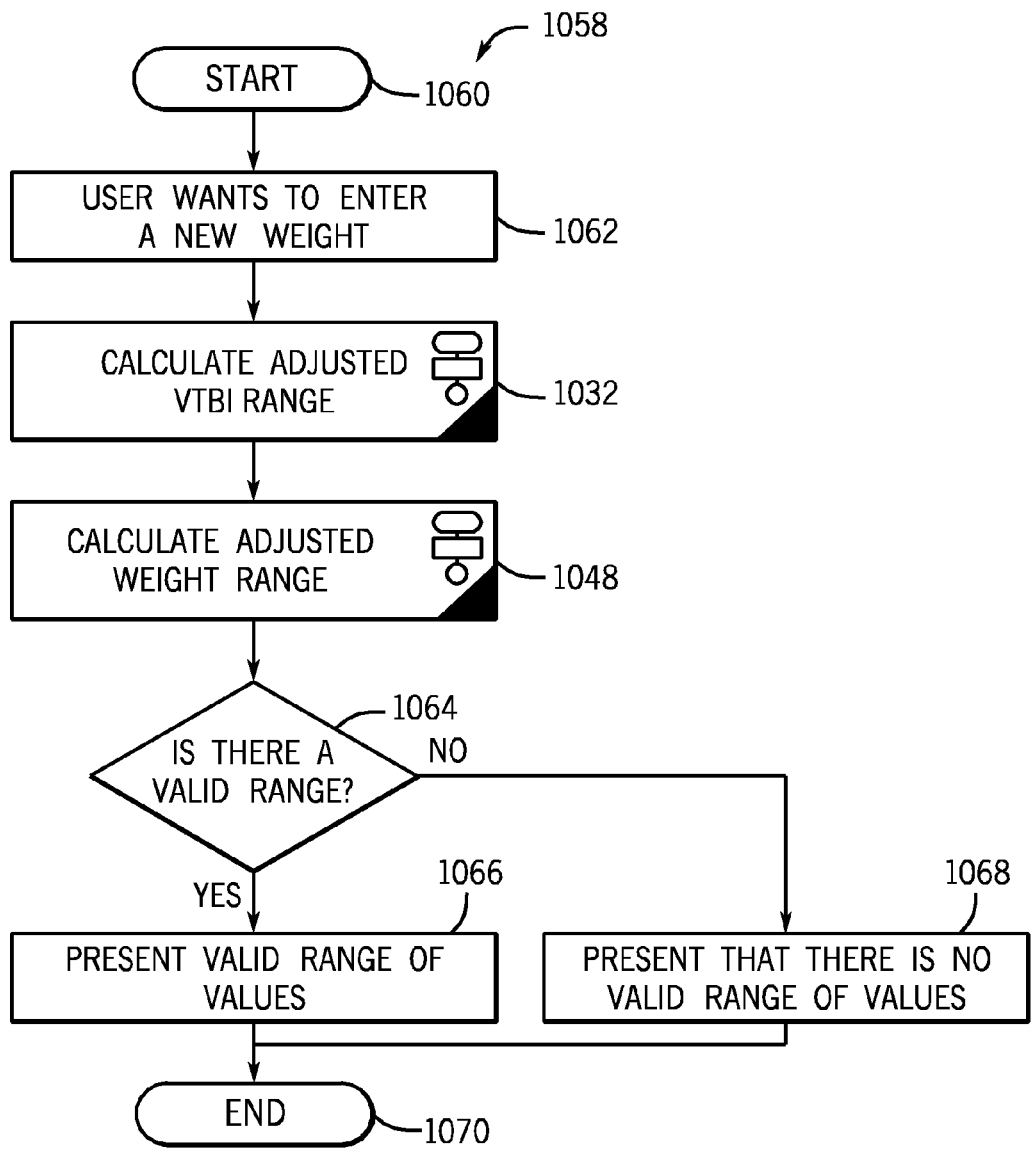
FIG. 13 is a flowchart of a process that calculates and displays the adjusted valid range for weight before a weight is entered when weight is part of a dose amount.

FIG. 13 shows a process 1058 for calculating and displaying the adjusted valid range for a weight before a weight is entered when weight is part of a dose amount. Starting at step 1060 a user wants to enter a new weight at step 1062 and the processor 12 calculates an adjusted valid range for VTBI to be entered at step 1032 (FIGS. 25A and 25B). Once an adjusted valid range is calculated for VTBI the processor 12 then calculates an adjusted valid range for weight to be entered at 1048 (FIG. 21) such that a determination of a valid range can be made at step 1064. If a valid range is present the processor 12 displays the values in the text box 134 on the output device 18 at step 1066 and if not, then the fact that no valid range is present is displayed at step 1068 and thus provides an end at step 1070.

Figure 14:
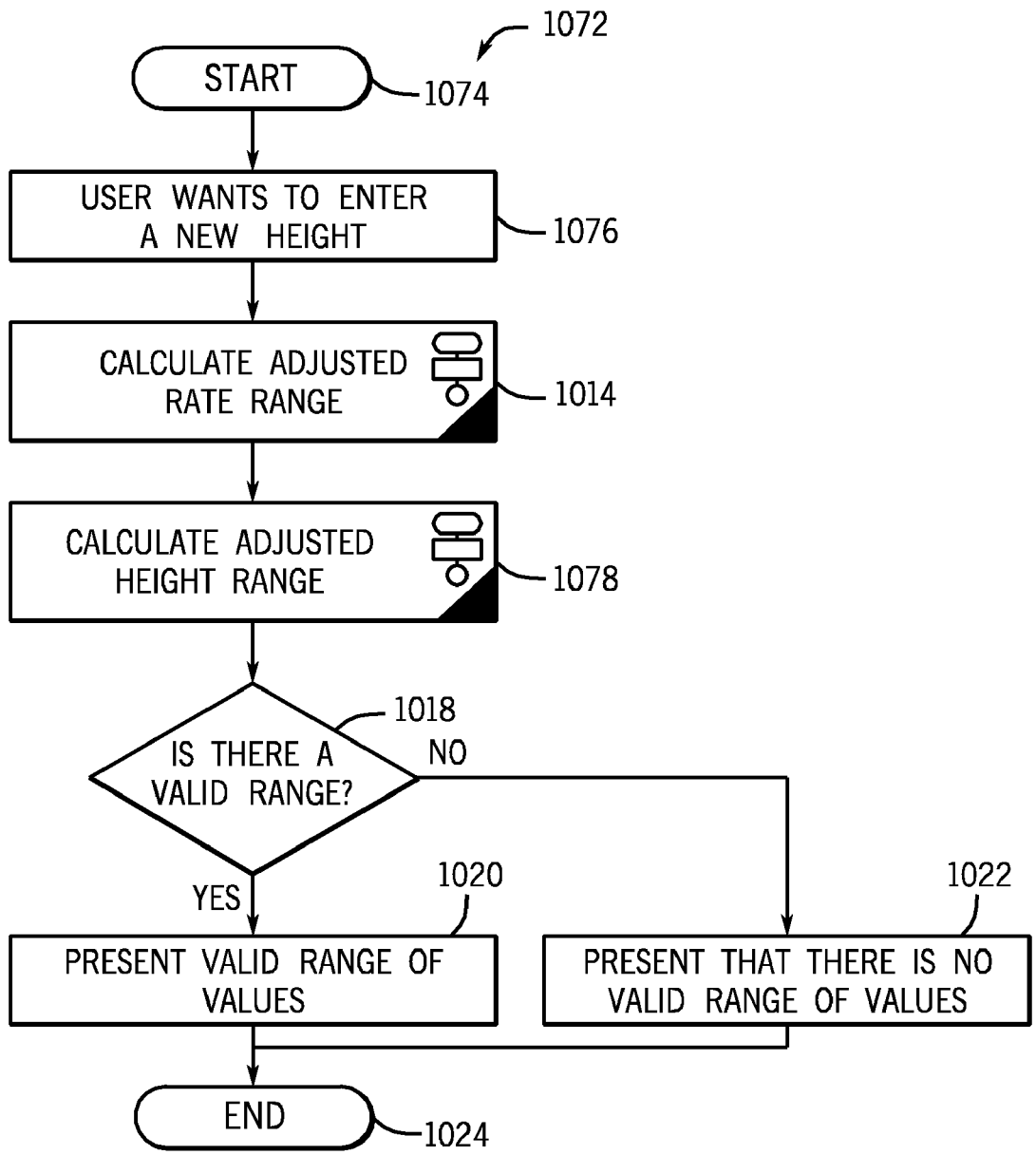
FIG. 14 is a flowchart of a process that calculates and displays the adjusted valid range for height before a height is entered when height is part of a dose rate.

FIG. 14 shows a process 1072 for calculating and displaying the adjusted valid range for a height before a height 106 is entered when height is part of a BSA (body surface area) which is part of a dose rate. At the start at step 1074 a user wants to enter a new height 106 at step 1076. This time the processor 12 calculates an adjusted valid range for rate 110 at step 1014 (FIGS. 24A and 24B). After calculating an adjusted valid range for rate 110 the processor 12 then calculates an adjusted valid range for height 106 at step 1078 (FIG. 22) so that a determination may be made at step 1018. If yes, step 1020 requires the processor 12 to display the valid range on the output device 18. Whereas if the answer is no, at step 1022 the fact that there is no valid range of values is presented on the output device 18 bringing the process 1072 to an end at step 1024.

Figure 15:
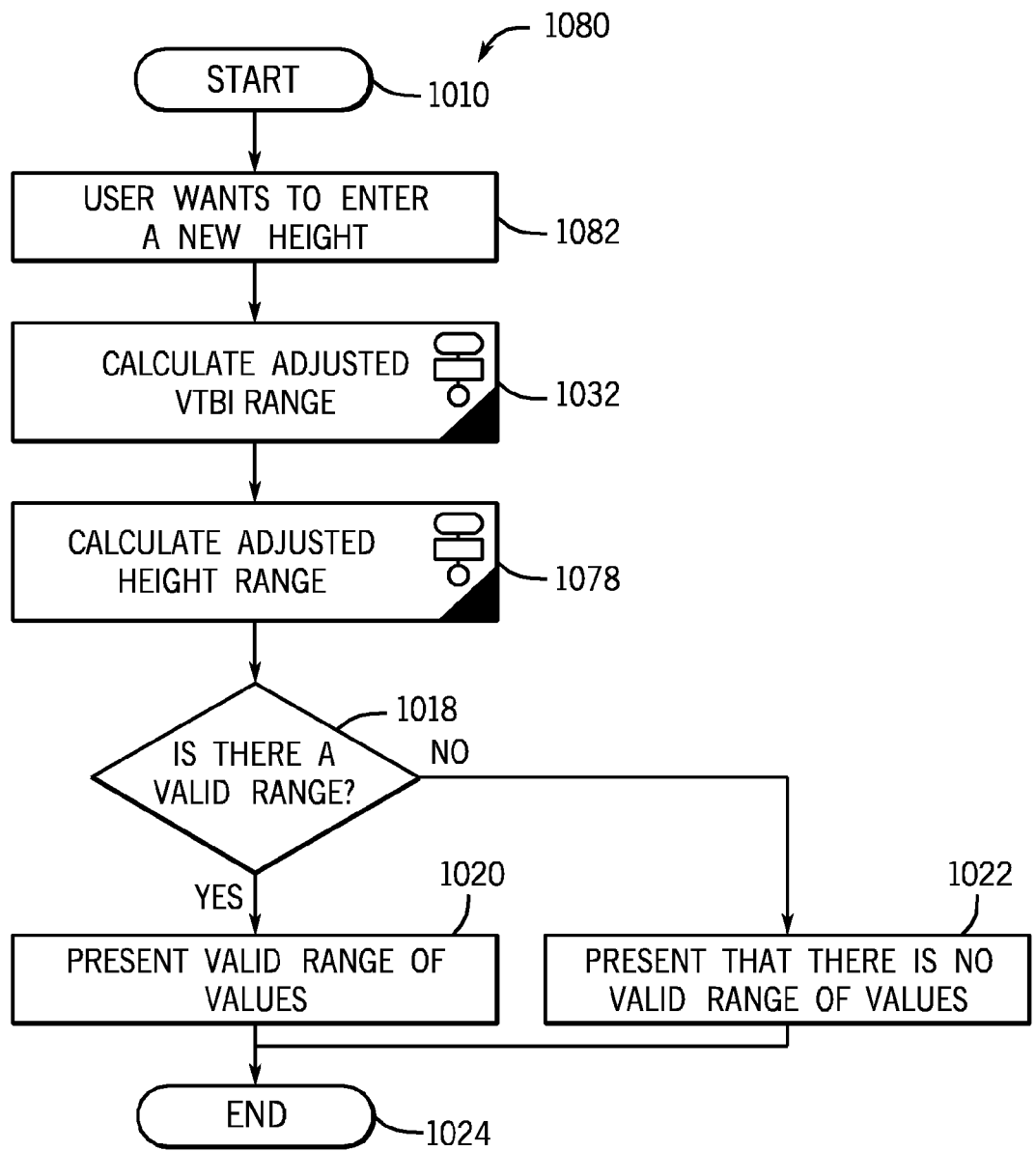
FIG. 15 is a flowchart of a process that calculates and displays the adjusted valid range for height before a height is entered when height is part of a dose amount.
Figure 22:
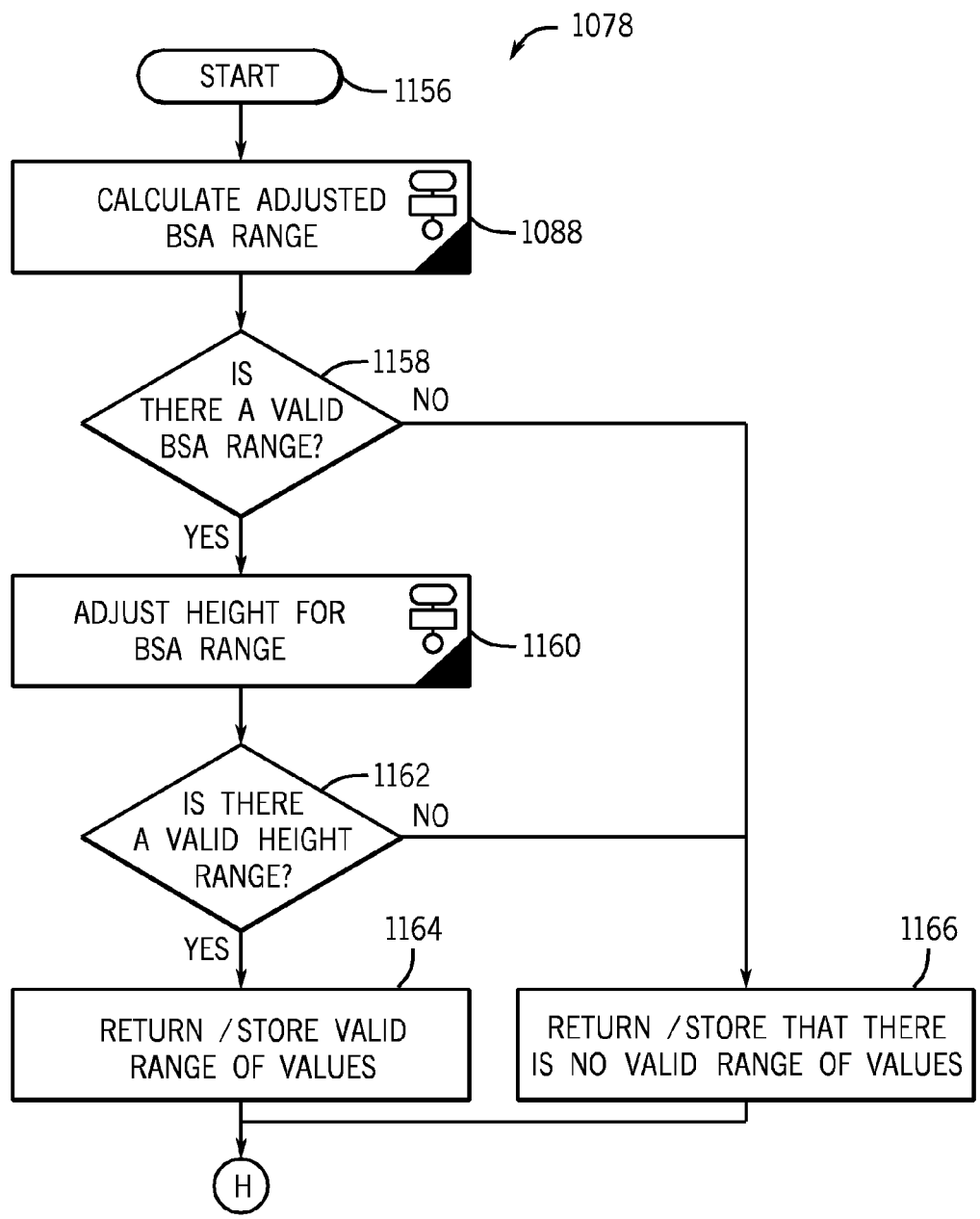
FIG. 22 is a flowchart of a process that calculates the adjusted valid range for height.

FIG. 15 shows a process 1080 for calculating and displaying the adjusted valid range for height before a height 106 is entered when height is part of a BSA (body surface area) which is part of a dose amount. After starting at step 1010 the user wants to enter a new height at step 1082. At this time the processor 12 calculates an adjusted valid range for VTBI (volume to be infused) at step 1032 (FIGS. 25A and 25B). After calculating an adjusted valid range for VTBI the processor 12 then calculates an adjusted valid range for height 106 at step 1078 (FIG. 22). At that time the processor 12 then makes a determination at step 1018 whether or not there is a valid range present and if so, displays the valid range at step 1020, and if not, displays that there is no valid range to provide at step 1022 and ends as in step 1024.

Figure 16:
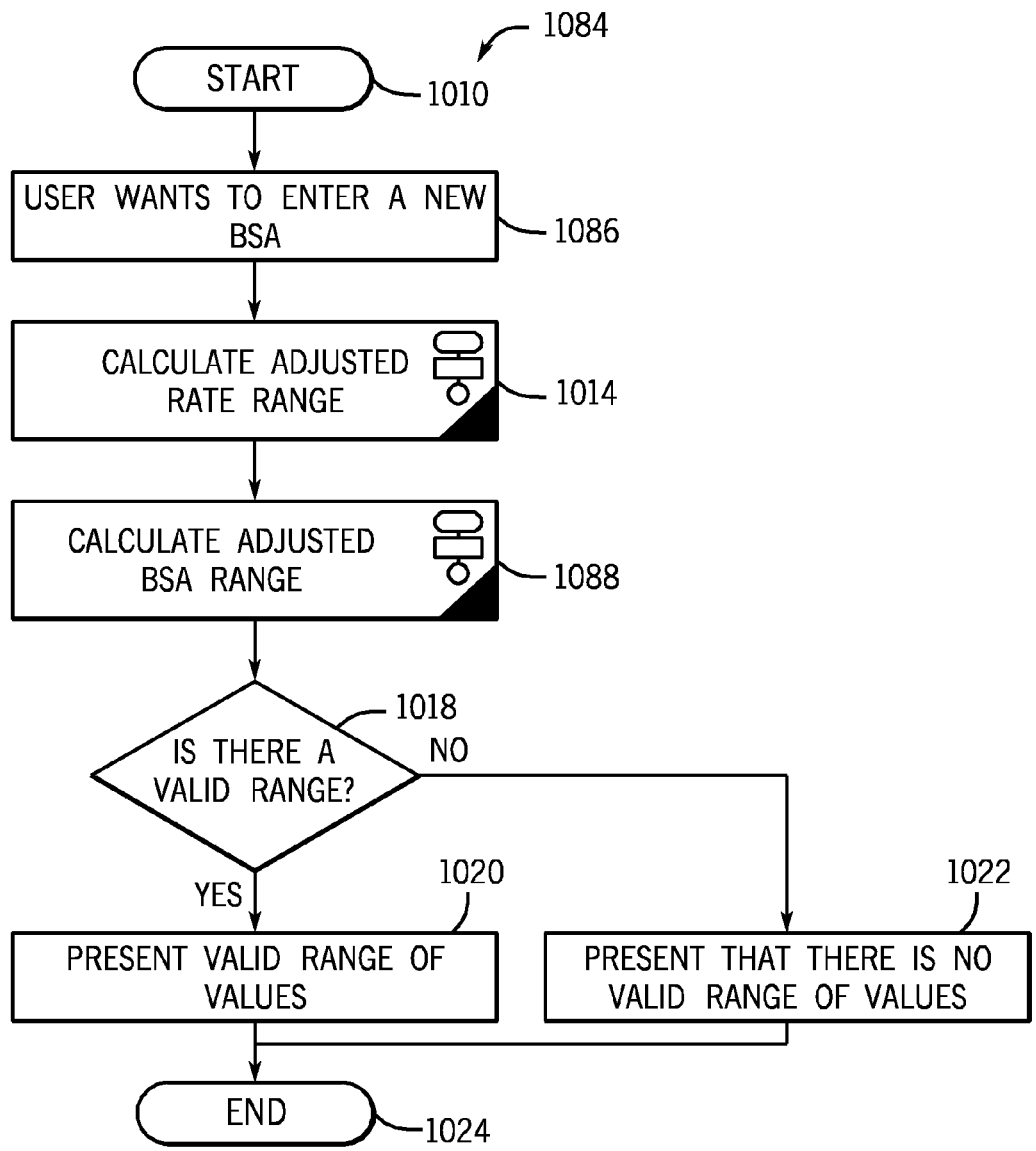
FIG. 16 is a flowchart of a process that calculates and displays the adjusted valid range for BSA before a BSA is entered when BSA is part of a dose rate.
Figure 23A:
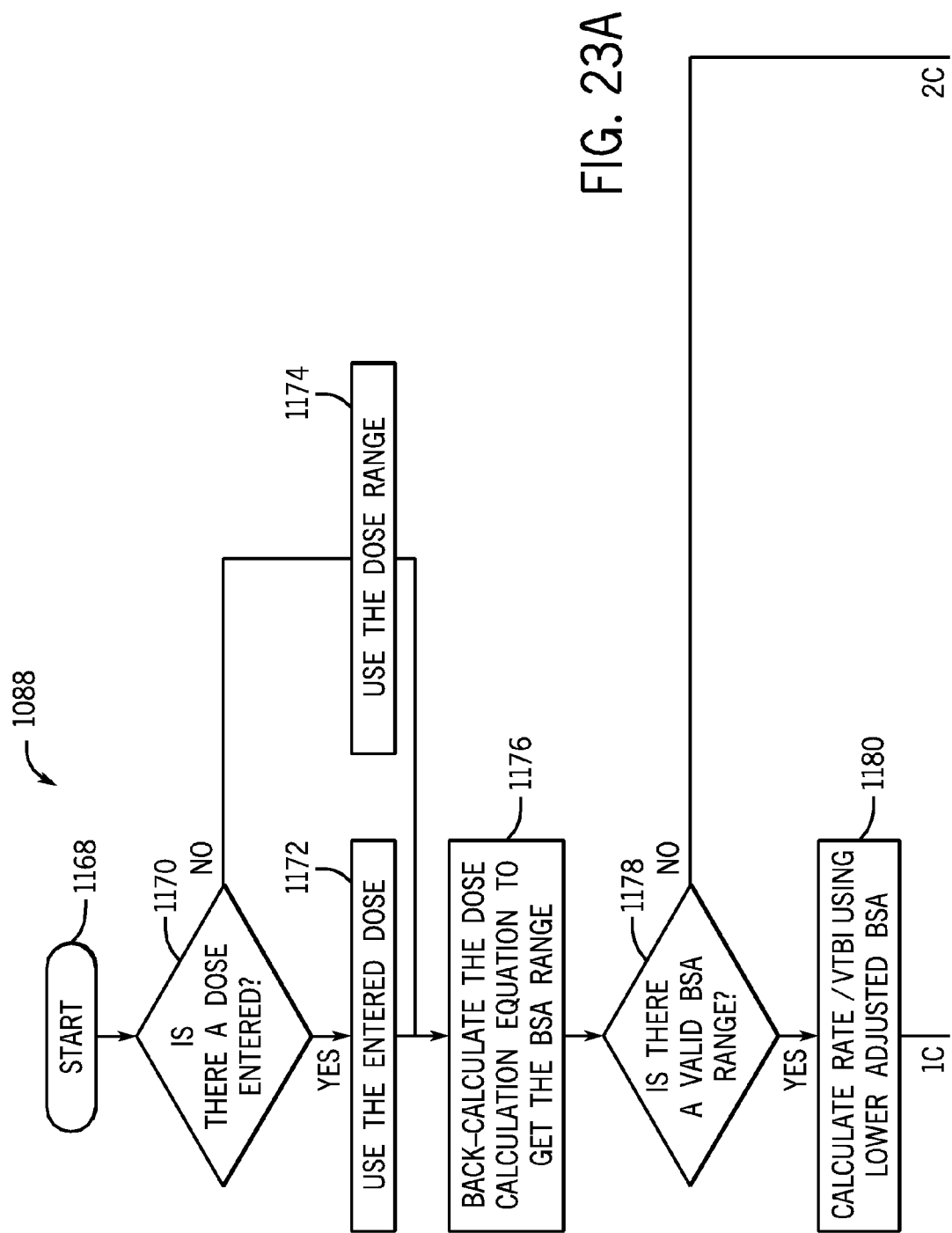
FIG. 23A is the initial portion of a flowchart of a process that calculates the adjusted valid range for BSA.
Figure 23B:
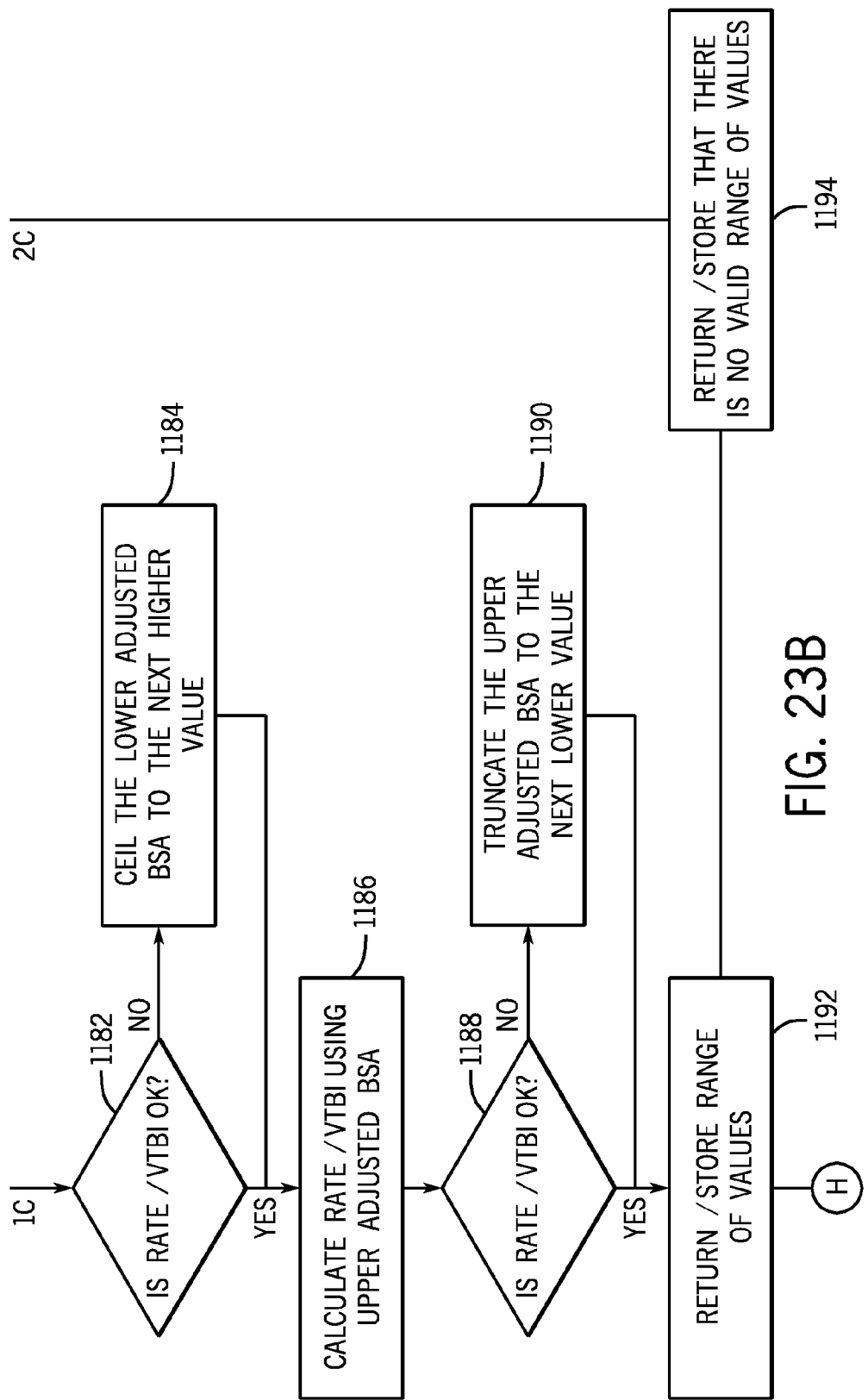
FIG. 23B is a continuation of the flowchart of FIG. 23A and shows the remaining portion of a process that calculates the adjusted valid range for BSA.

FIG. 16 shows a process 1084 for calculating and displaying the adjusted valid range for BSA (body surface area) before a BSA is entered when BSA is part of a dose rate. Starting at step 1010 a user wants to enter a new BSA (body surface area) at step 1086 and as such the processor 12 calculates an adjusted valid range for rate at step 1014 (FIGS. 24A and 24B). At this time the processor 12 calculates an adjusted valid range for BSA (body surface area) at step 1088 (FIGS. 23A and 23B). At step 1018 a determination is made whether or not there is a valid range present. If a valid range is present the processor 12 displays the values in text box 134 on the output device 18 at step 1020 and if not, then the fact that no valid range is present is displayed at step 1022 and thus provides an end at step 1024.

Figure 17:
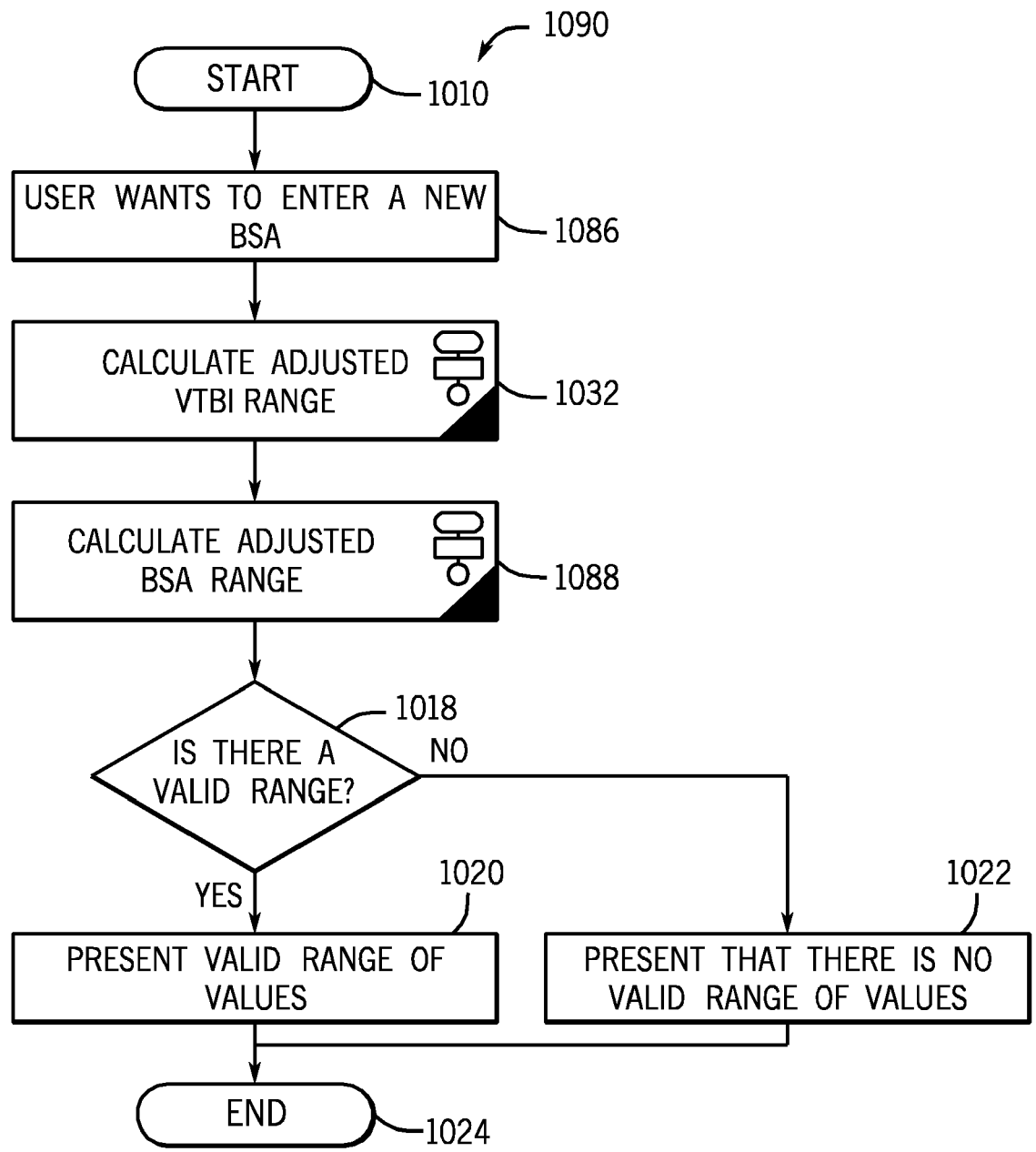
FIG. 17 is a flowchart of a process that calculates and displays the adjusted valid range for BSA before a BSA is entered when BSA is part of a dose amount.

FIG. 17 shows a process 1090 for calculating the adjusted valid range for BSA (body surface area) before BSA is entered when BSA is part of a dose amount. Starting at step 1010 a user wants to enter a new BSA (body surface area) at step 1086. The processor 12 calculates an adjusted valid range for VTBI (volume to be infused) at step 1032 (FIGS. 25A and 25B). At this time the processor 12 then calculates an adjusted valid range for BSA (body surface area) at step 1088 (FIGS. 23A and 23B). At step 1018 a determination is made whether or not there is a valid range present. If a valid range is present the processor 12 displays the valid range at step 1020 and if not, then fact that there is no valid range is displayed at step 1022 and thus provides an end at step 1024.

Figure 18A:
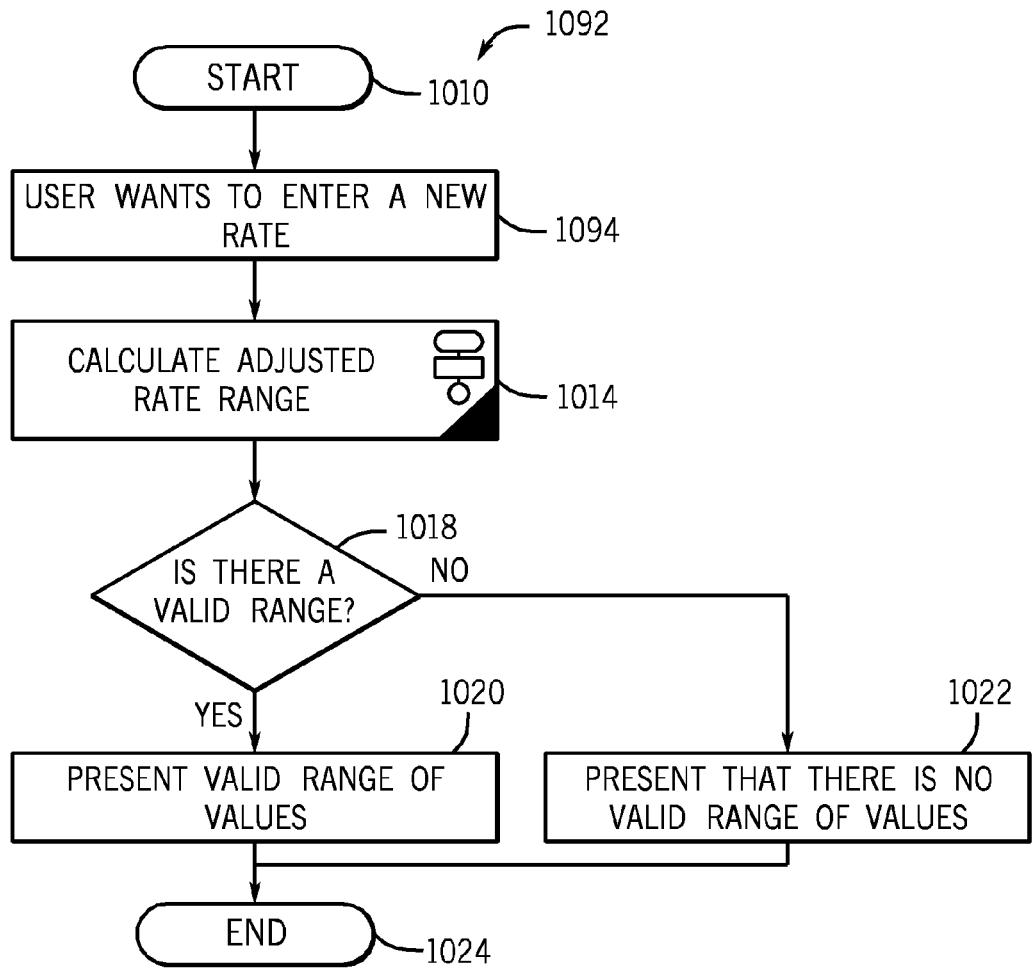
FIG. 18A is a flowchart of a process that calculates and displays the adjusted valid range for rate.

FIG. 18A shows a process 1092 for calculating and displaying the adjusted valid range for rate before entering a new rate. After starting at step 1010 a user wants to enter a new rate at step 1094 the processor 12 calculates an adjusted valid range for the rate at step 1014 (FIGS. 24A and 24B). At step 1018 a determination is made whether or not there is a valid range present. If a valid range is present the processor 12 displays the valid range at step 1020 and if not, the fact that there is no valid range is displayed at step 1022 and thus provides an end at step 1024.

Figure 18B:
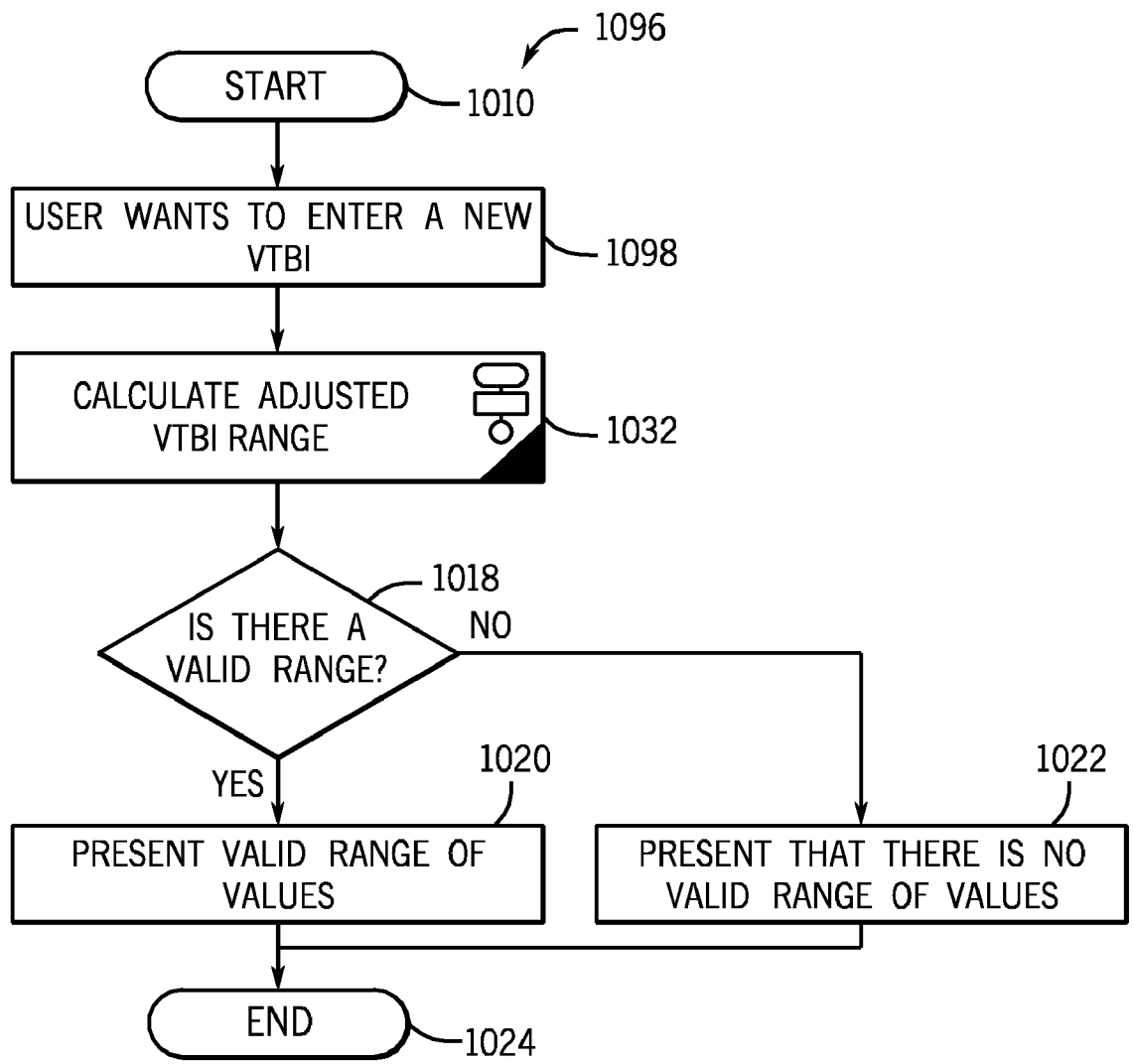
FIG. 18B is a flowchart of a process that calculates and displays the adjusted valid range for VTBI.

FIG. 18B shows a process 1096 for calculating and displaying the adjusted valid range for VTBI (volume to be infused) before a VTBI is entered. Starting at step 1010 the user desires to enter a new VTBI as shown at step 1098. At that point in time, the processor 12 calculates an adjusted valid range for the VTBI at step 1032 (FIGS. 25A and 25B). A determination is then made at step 1018 whether or not there is a valid range present. If there is a valid range present the valid range is displayed by the processor 12 at step 1020 and if not, the fact that there is no valid range present is displayed at step 1022 and thus provides an end at step 1024.

Figure 19:
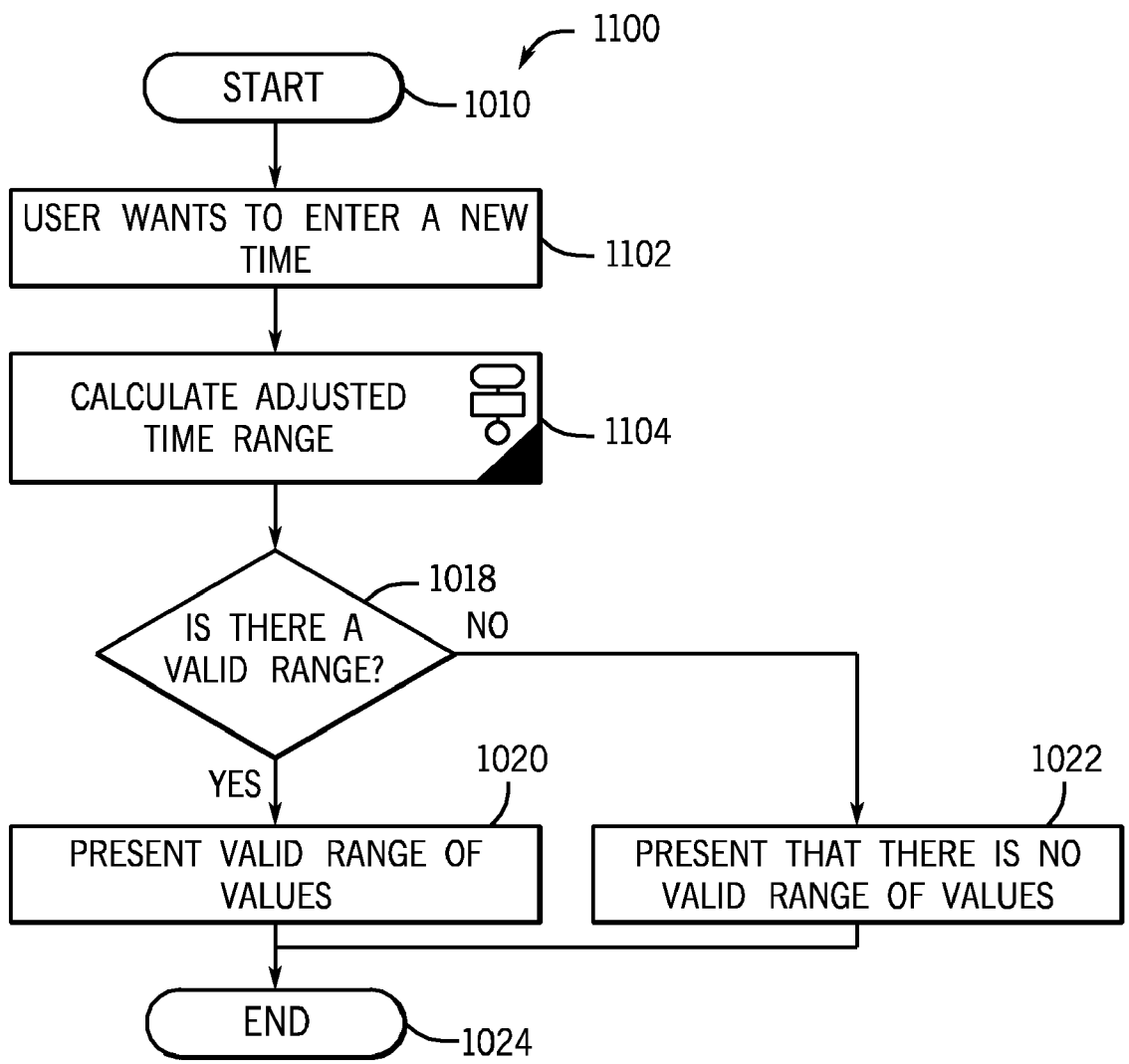
FIG. 19 is a flowchart of a process that calculates and displays the adjusted valid range for time.
Figure 26:
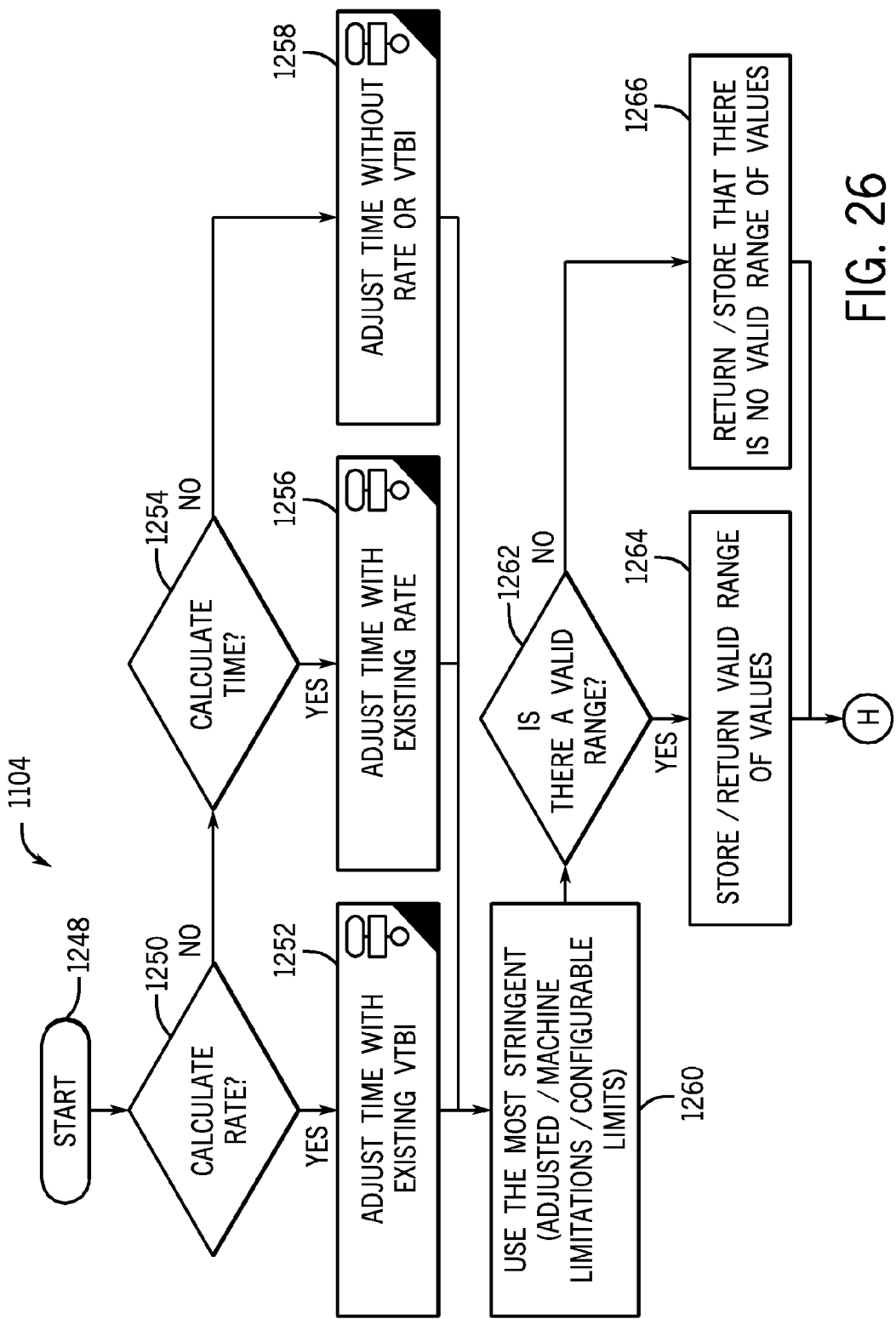
FIG. 26 is a flowchart of a process that calculates the adjusted valid range for time.

FIG. 19 shows a process 1100 for calculating and displaying the adjusted valid range for time 116 before time 116 is entered. Specifically, after starting at step 1010 a user wants to enter a new time 116 at step 1102 the processor 12 calculates an adjusted valid range of time 116 at step 1104 (FIG. 26). Thus, the processor 12 determines whether a valid range is present as step 1018. I a valid range is present the valid range is displayed at step 1020 and if not, the fact that there is no valid range is displayed by the processor 12 at step 1022 and thus provides an end at step 1024.

FIG. 20 shows the process 1016 used to calculate the adjusted valid range for dose rate or dose amount 118. Specifically, after a start at step 1010 a determination is made at step 1106 regarding whether the dose is weight or BSA (body surface area) based. If the dose is weight or BSA based then the processor 12 makes a determination whether the dose is weight based or BSA based at step 1108.

If the dose is BSA based then a determination is made at step 1110 whether a BSA has been entered previously. If yes, the entered BSA will be used during later calculations as indicated at step 1112 and if not, a BSA range will be used during later calculations as indicated at step 1114. If instead, the dose is weight based at step 1108 the processor 12 determines if there is a weight previously entered at step 1116 and if yes, this weight will be used during later calculations as indicated by step 1118 and if no, a weight range will be used during later calculations as indicated by step 1120.

Once the processor 12 determines whether an entered weight, a weight range, an entered BSA, a BSA range or that the dose is neither weight nor BSA based, the processor 12 back calculates the dose calculation equation to get an adjusted valid dose range at step 1122. After the processor 12 back calculates the dose calculation equation to get the adjusted dose range at step 1122 a determination is made at step 1124 whether there is a valid dose range. If there is a valid dose range at step 1124 then at step 1126 the processor 12 calculates, using rounding, either rate (dose rate therapies) or the VTBI (dose amount therapies) using the lower limit value of the adjusted valid range for dose.

At this time a determination is made at step 1128 regarding whether the calculated rate or VTBI is proper. If not, at step 1130 the lower adjusted value of the adjusted valid range for rate or VTBI is ceiled to the next higher value. At this point, or if the rate or VTBI at step at 1128 is proper, rate or VTBI is then calculated, using rounding, using the upper adjusted dose range value at 1132.

A determination is then again made if the rate or VTBI is proper and if not, the upper adjusted valid range value of the dose is truncated to the next lower value at step 1136.

After the processor 12 determines that the rate or VTBI is proper at step 1134 or after truncation of the adjusted range limit at step 1136 a new valid range for the dose rate or dose amount is presented, returned, and/or stored within the memory 24 at step 1138. If, on the other hand, at step 1124 there is not a valid dose range then the processor 12 determines that there is no valid range of values and this information is presented, retuned, and/or stored within the memory 24 instead of the new valid range of values at step 1140. After either step 1138 or 1140 the process 1016 is ended and the processor 12 continues execution of the process which called process 1016.

Figure 27A:
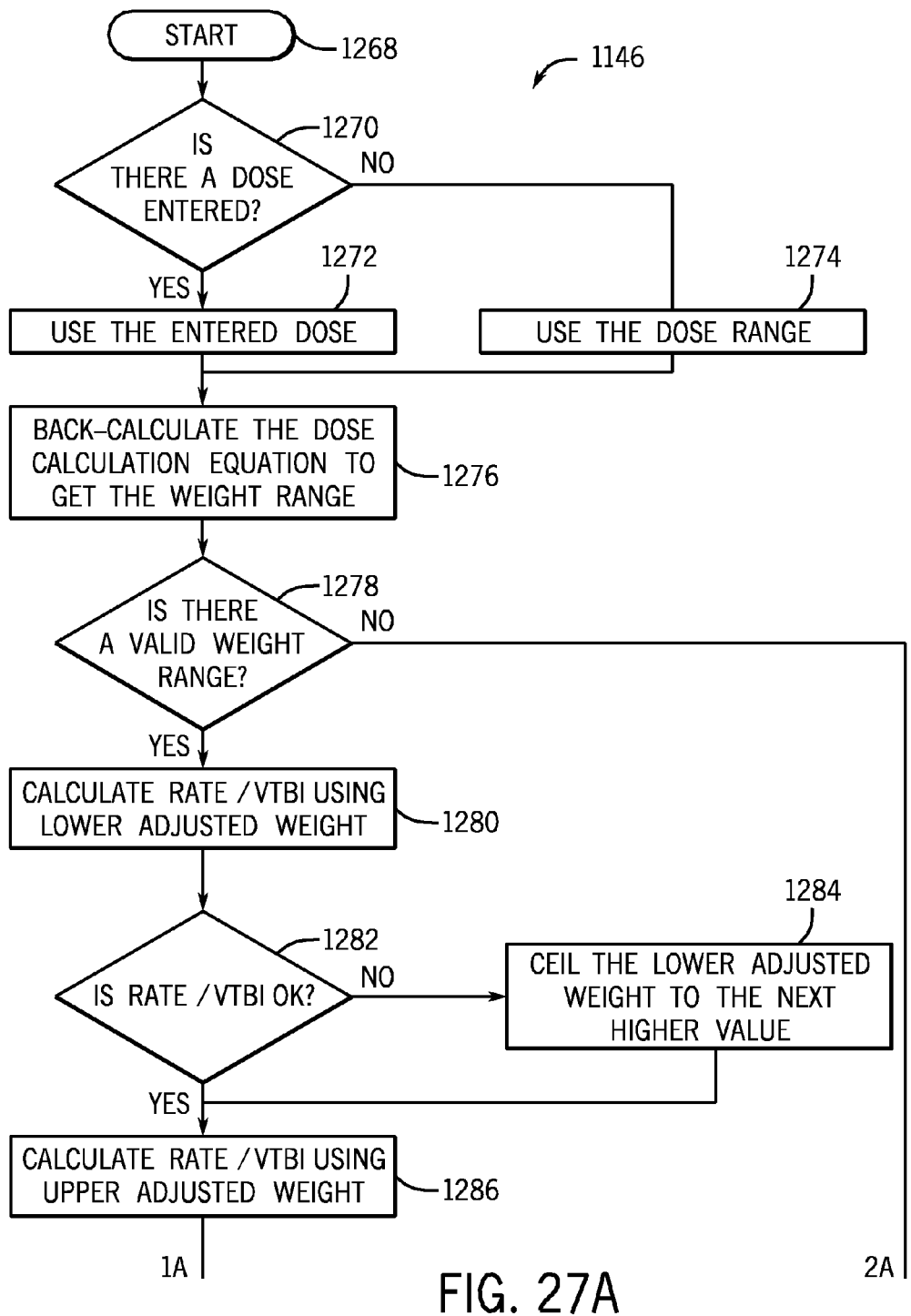
FIG. 27A is the initial portion of a flowchart of a process that calculates the adjusted valid range for weight when weight is part of a dose calculation.
Figure 27B:
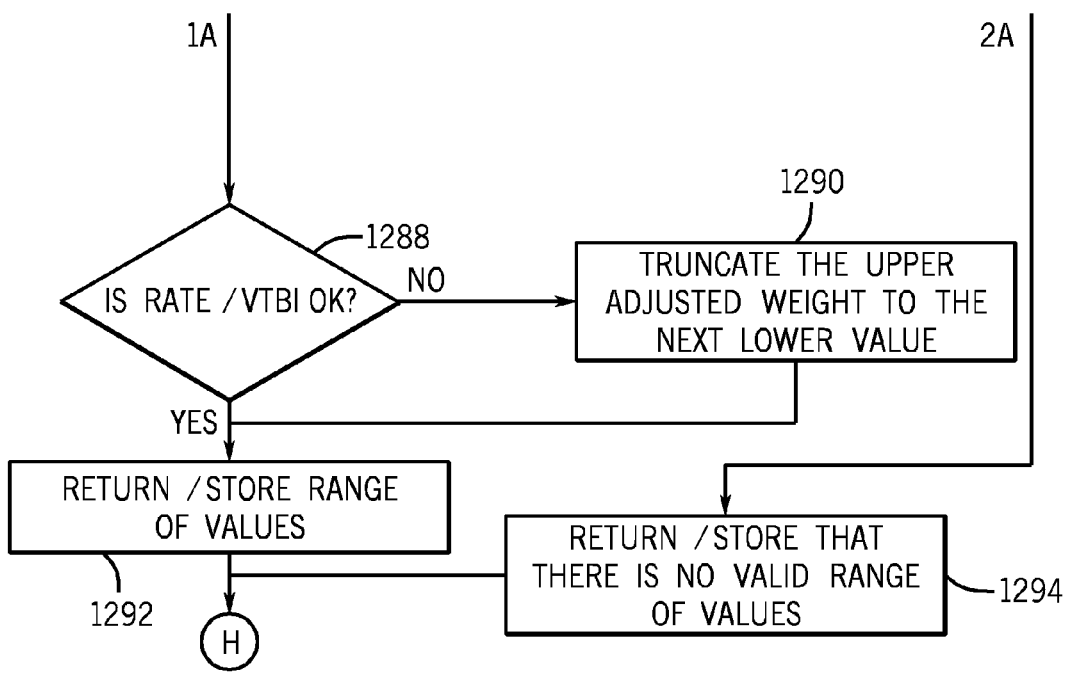
FIG. 27B is a continuation of the flowchart of FIG. 27A and shows the remaining portion of a process that calculates the adjusted valid range for weight when weight is part of a dose calculation.
Figure 28A:
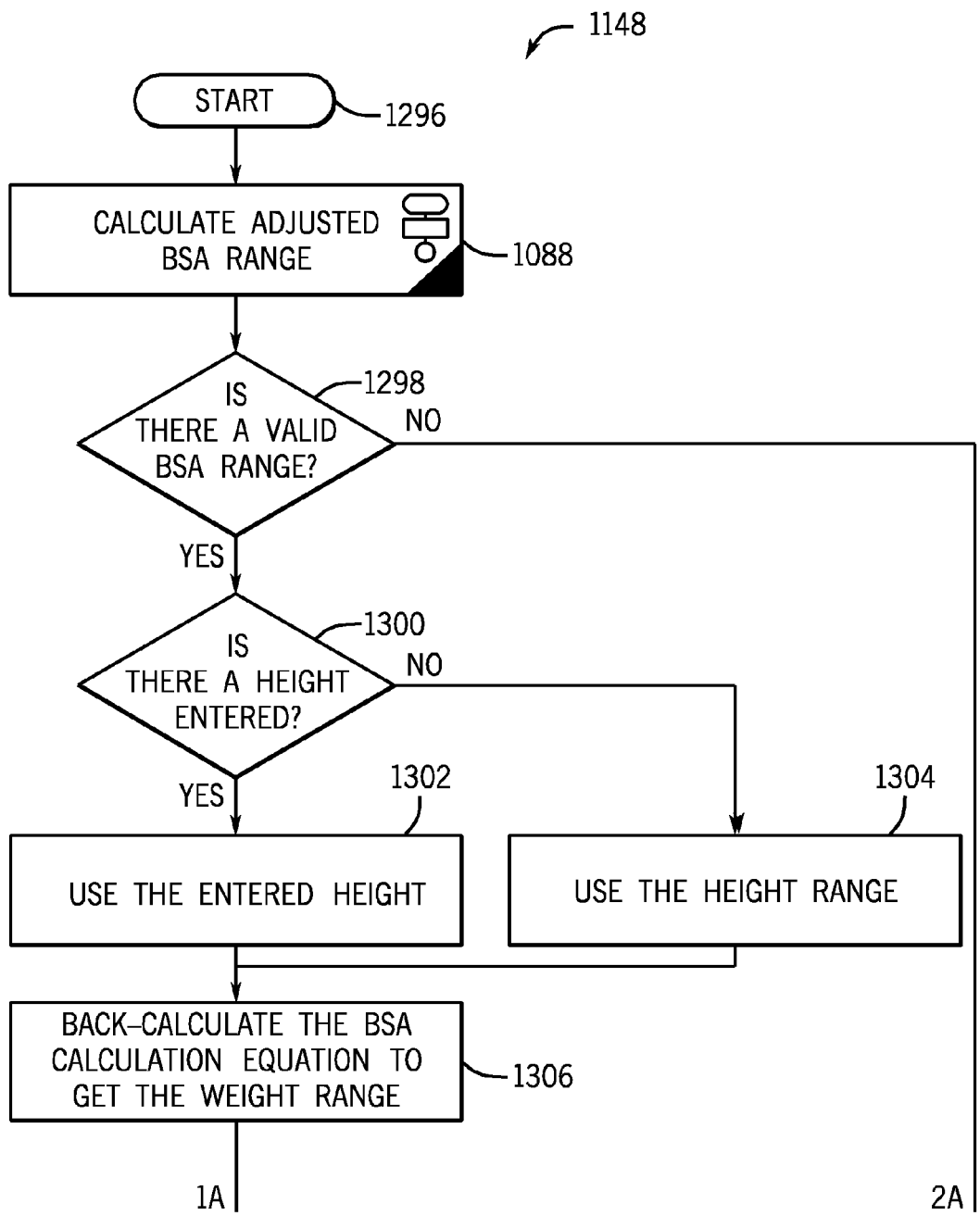
FIG. 28A is the initial portion of a flowchart of a process that calculates the adjusted valid range for weight when weight is part of a BSA calculation.
Figure 28B:
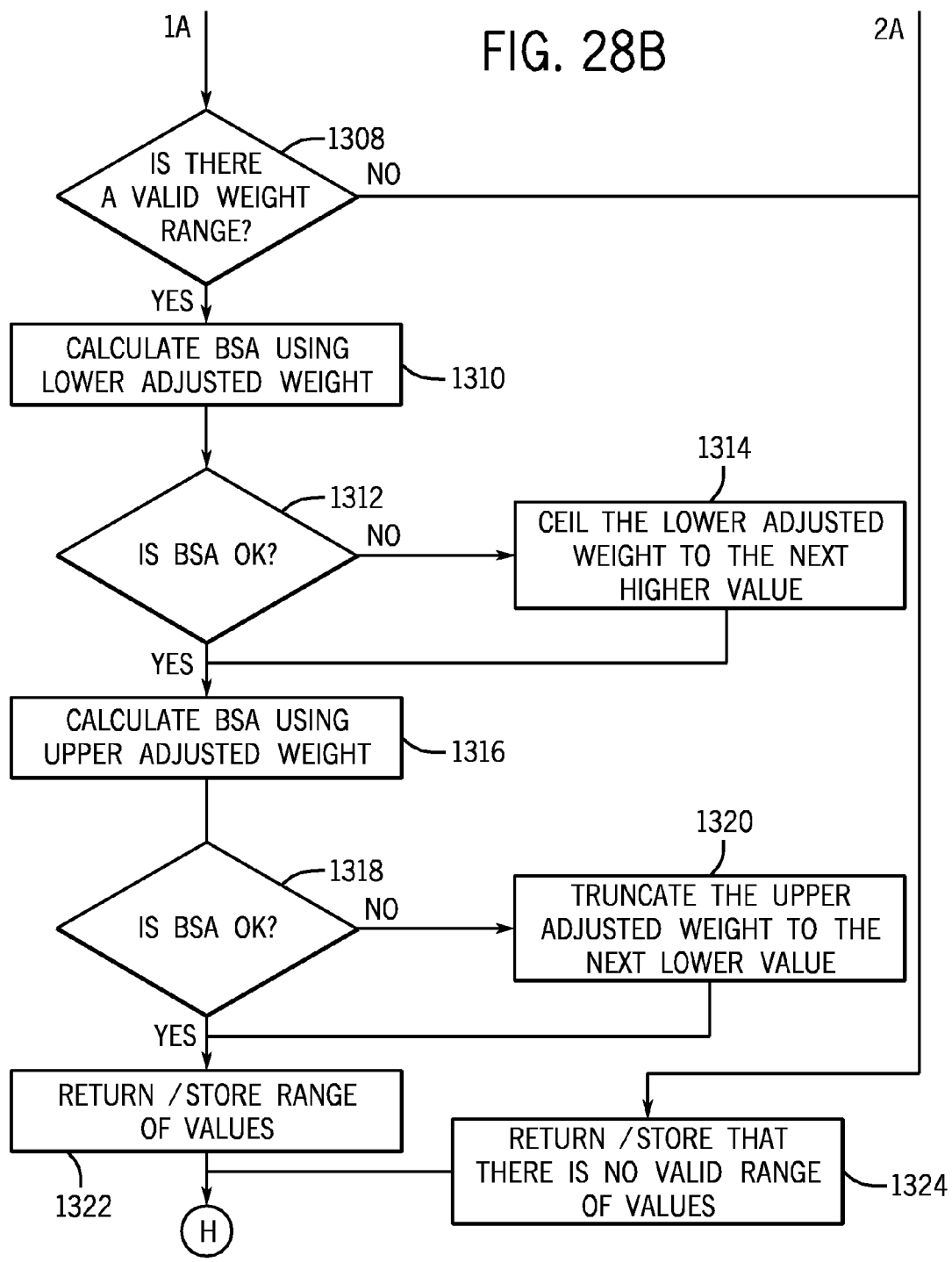
FIG. 28B is a continuation of the flowchart of FIG. 28A and shows the remaining portion of a process that calculates the adjusted valid range for weight when weight is part of a BSA calculation.

FIG. 21 shows the process 1048 for calculating an adjusted valid range for weight 104. Specifically, at the start 1142 a determination is made whether the dose rate or dose amount is weight or BSA based at step 1144. If weight based the valid range for the weight 104 is adjusted for the dose calculation range at step 1146 (FIGS. 27A and 27B). If instead, the dose rate is BSA (body surface area) based, the processor adjusts the valid range for the weight for the BSA range as shown in step 1148 (FIGS. 28A and 28B). At this time, the processor 12 determines if there is a valid range for weight at step 1150. If there is a valid range for weight that valid range is returned and/or stored in the memory 24 at step 1152. Whereas if there is not a valid weight range, that information similarly is returned and/or stored in the memory at step 1154. After either step 1152 or 1154 the process 1048 is ended and the processor 12 continues execution of the process which called process 1048.

Figure 29A:
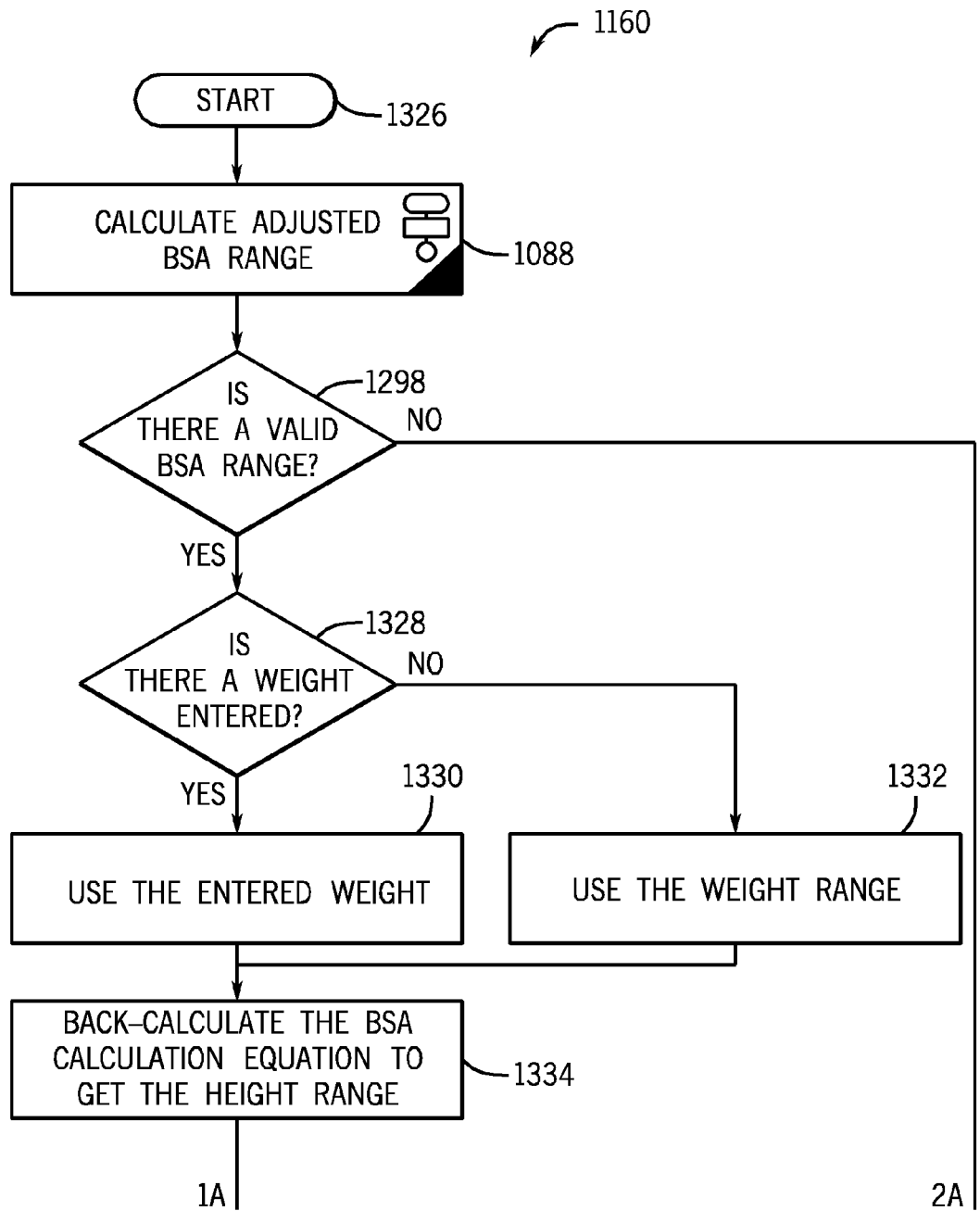
FIG. 29A is the initial portion of a flowchart of a process that calculates the adjusted valid range for height when height is part of a BSA calculation.
Figure 29B:
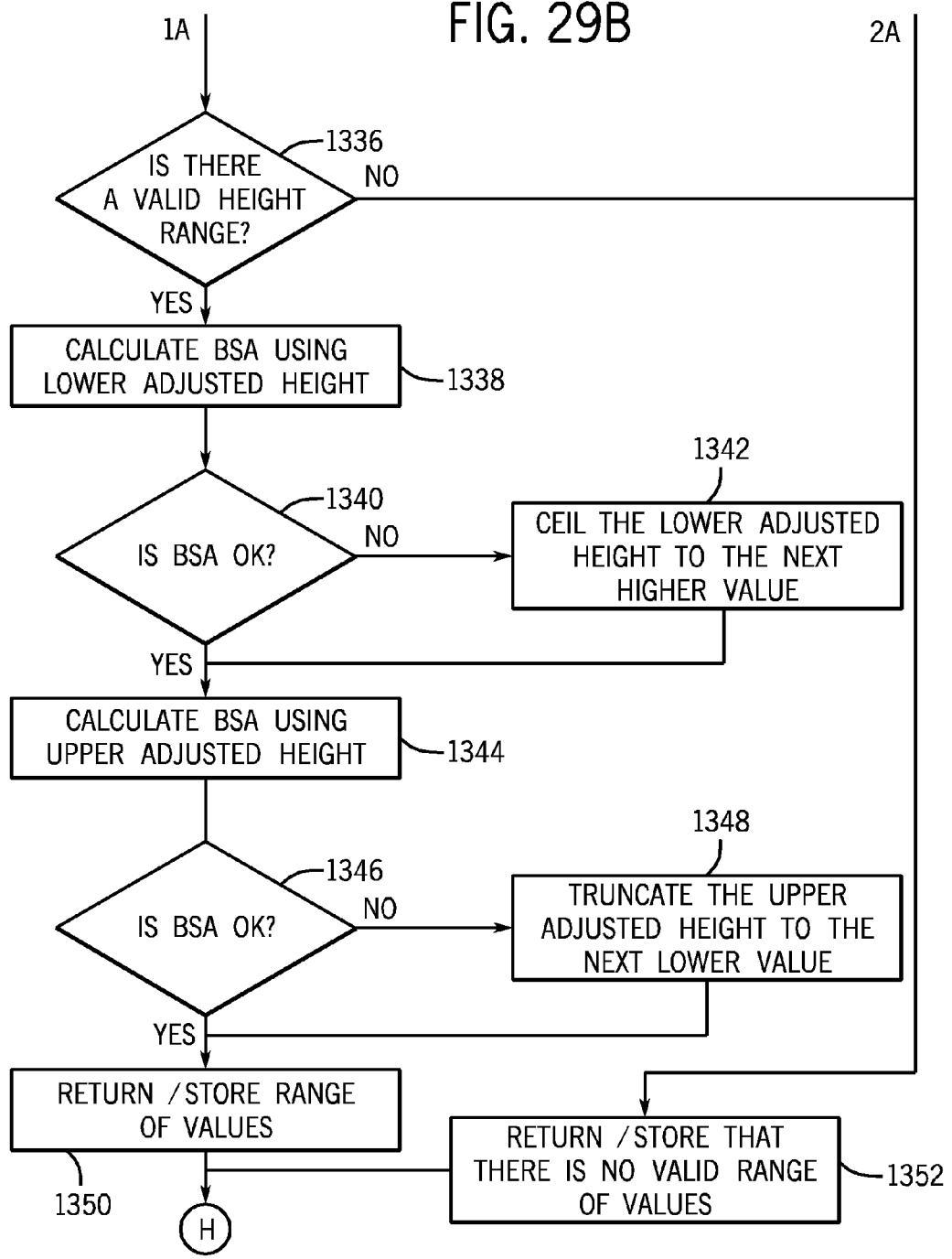
FIG. 29B is a continuation of the flowchart of FIG. 29A and shows the remaining portion of a process that calculates the adjusted valid range for height when height is part of a BSA calculation.

FIG. 22 shows a process 1078 for calculating an adjusted valid range of height 106. After starting at step 1156 the processor 12 calculates an adjusted valid range for BSA (body surface area) as shown in step 1088 (FIGS. 23A and 23B). A determination is then made at step 1158 whether there is a valid BSA range. If there is a valid BSA range then the valid range for height 106 is adjusted for the BSA range at step 1160 (FIGS. 29A and 29B). A determination is then made at step 1162 whether there is a valid range for height. If there is a valid range for height, this valid range of values is returned and/or stored in the memory 24 of the processor 12 as indicated at step 1164. If, however, there is either not a valid BSA range in regards to step 1158 or there is not a valid range for height in regard to step 1162 then the processor returns and/or stores within the memory 24 the information that there is not a valid range of values for height at step 1166. After either step 1164 or 1166 the process 1078 is ended and the processor 12 continues execution of the process which called process 1078.

FIGS. 23A and 23B show a process 1088 for calculating an adjusted valid range for BSA (body surface area). After starting at 1168 a determination is made whether a dose is entered at step 1170. If a dose is entered, that dose will be used during later calculations as indicated at step 1172 whereas if a dose is not entered, the processor 12 uses a dose range during later calculations as indicated at step 1174. Whether using an actual dose or a dose range the next step is to back calculate the dose calculation equation to get a BSA (body surface area) range at step 1176.

After back calculating the dose calculation equation to get the BSA (body surface area) range at step 1176 a determination is made regarding whether there is a valid range for BSA at step 1178. If there is a valid range for BSA the processor 12 then calculates, using rounding, rate 112 (dose rate therapies) or VTBI (dose amount therapies) using the lower limit value of the adjusted valid range for BSA at step 1180. Then a determination is made if the rate or VTBI is proper at step 1182 and if not, the lower adjusted valid range limit value for BSA is ceiled to the next higher value at step 1184.

Either after the rate or VTBI calculation is considered proper at step 1182 or is considered improper and the lower adjusted valid range value for BSA is ceiled at step 1184 the processor 12 calculates, using rounding, the rate or VTBI using the upper limit value of the adjusted valid range for BSA at step 1186. At this point in time the processor again determines if the calculated rate or VTBI is proper at step 1188. If improper the processor 12 truncates the upper limit value of the adjusted valid range for BSA to the next lower value at step 1190. Either after the rate or VTBI is considered proper at step 1188 or the upper limit value of the adjusted valid range for BSA is truncated at step 1190, this range of values is returned and/or stored by the processor 12 in its memory 24 at step 1192. In opposite, if at step 1178 there was not a valid BSA range, the processor 12 returns and/or stores this information instead in its memory at step 1194. After either step 1192 or 1194 the process 1088 is ended and the processor 12 continues execution of the process which called process 1088.

Figure 31:
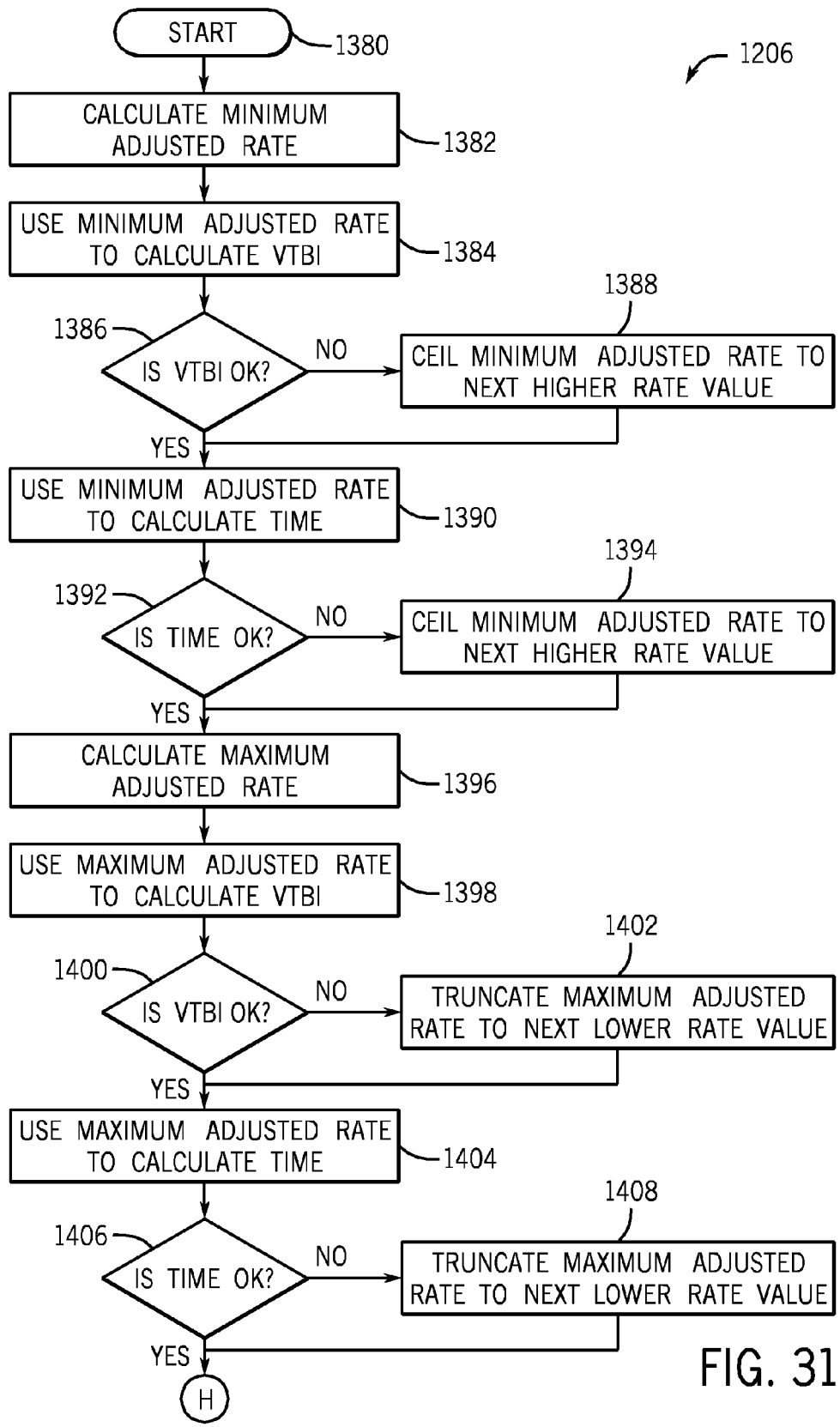
FIG. 31 is a flowchart of a process that calculates the adjusted valid range for rate without any existing VTBI or time.
Figure 32:
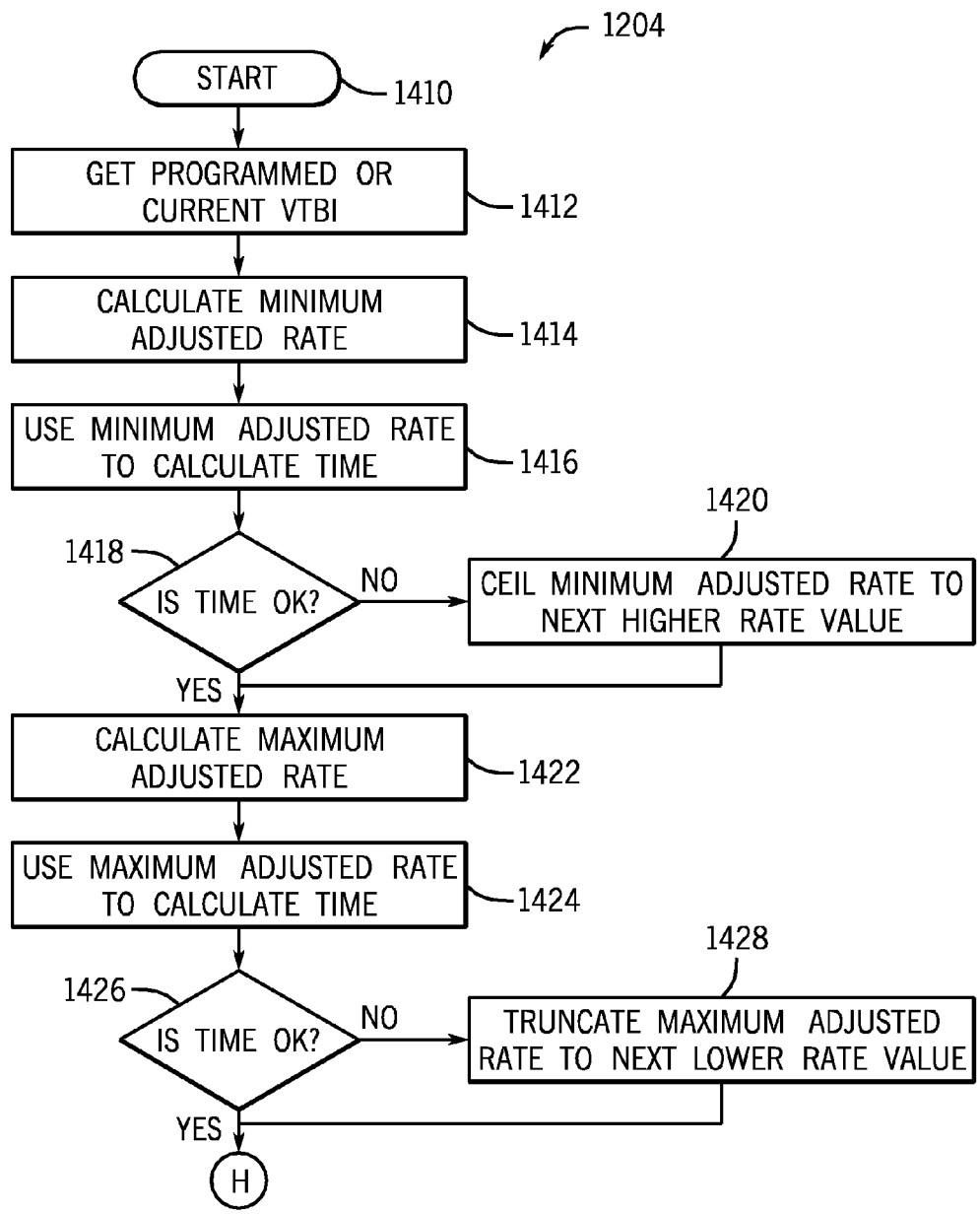
FIG. 32 is a flowchart of a process that calculates the adjusted valid range for rate when an existing VTBI is present such that time is calculated once the new rate is entered.
Figure 33A:
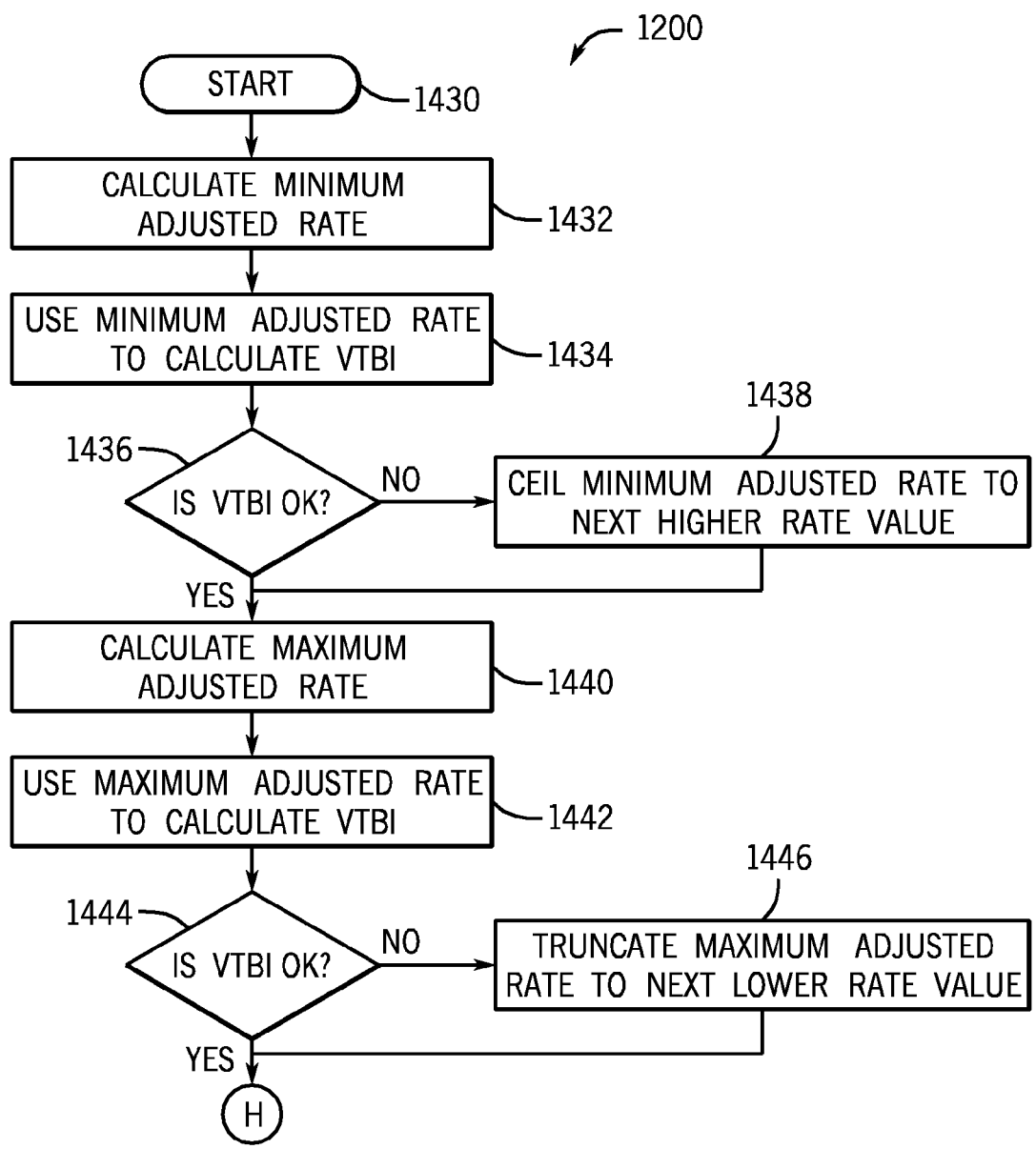
FIG. 33A is a flowchart of a process that calculates the adjusted valid range for rate when an existing time is present such that VTBI is calculated once the new rate is entered.

FIGS. 24A and 24B show a process 1014 for calculating an adjusted valid range for rate. At the start 1196 a determination is made at step 1198 whether or not to calculate VTBI (volume to be infused) once a new rate is entered. If VTBI is to be calculated then the valid range for rate is adjusted with the existing time at step 1200 (FIG. 33A). If VTBI is determined not to be calculated once a new rate is entered at step 1198 then a second determination is made regarding whether time is to be calculated once a new rate is entered at step 1202. If time is to be calculated then the valid range of rate is adjusted with the existing VTBI at step 1204 (FIG. 32). Whereas if time is determined not to be calculated once a new rate is entered at step 1202, the valid range of the rate is adjusted without any existing VTBI or time at step 1206 (FIG. 31).

Figure 30:
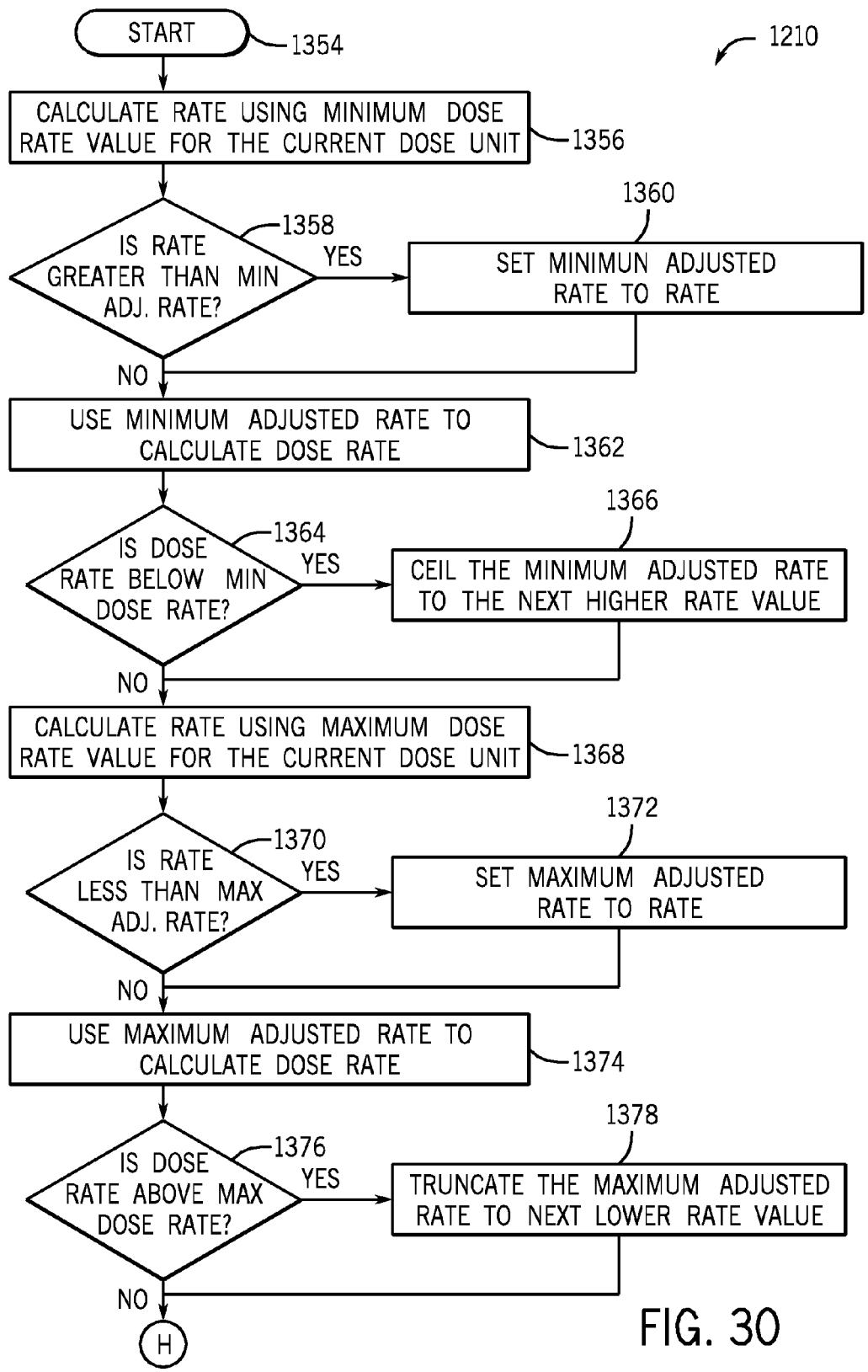
FIG. 30 is a flowchart of a process that calculates the adjusted valid range for rate from a dose rate range.

Once the valid range for rate is adjusted via steps 1200, 1204 or 1206 a determination is made regarding whether or not the dose rate is to be back calculated once a new rate is entered at step 1208. If the dose rate is to be back calculated the valid range for rate is again adjusted for the back calculated dose rate range at step 1210 (FIG. 30).

Figure 33B:
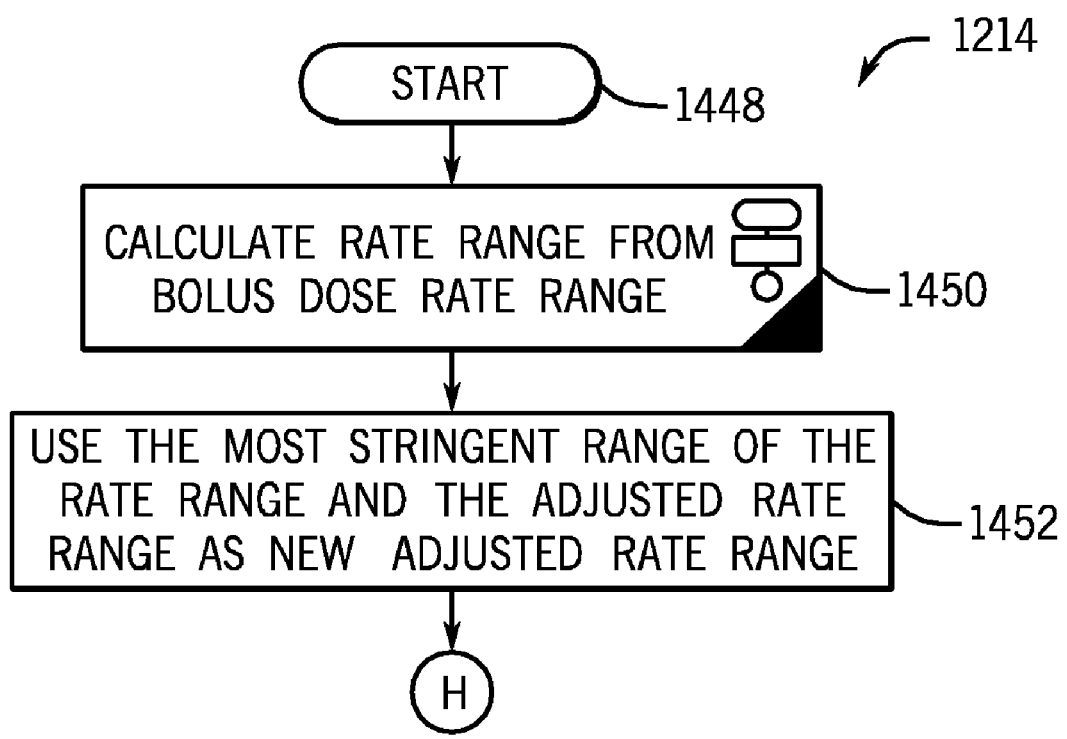
FIG. 33B is a flowchart of a process that calculates the adjusted valid range for rate from a bolus dose rate range.

After the valid range for rate is back calculated from the dose rate range at step 1210 or if the dose rate is not to be back calculated once a new rate is entered a second determination is made at step 1212 regarding whether or not the bolus dose rate 118 is to be calculated once a new rate is entered. If bolus dose rate is to be calculated, the valid range for rate is adjusted for the bolus dose rate range at step 1214 (FIG. 33B). After the adjustment at step 1214 or if the bolus dose rate is determined not to be calculated once a new rate is entered at step 1212 the processor 12 then uses the most stringent valid range determined in accordance with the adjusted valid range, machine limitations and configurable limits at step 1216. At that time a determination is made if there is a valid range at step 1218 and if there is, this valid range is considered to be the new adjusted valid range for rate and is returned and/or stored in the memory 24 at step 1220. If there is not a valid range this means that there is no valid value of rate that may be entered and this is instead returned and/or stored in the memory 24 at step 1222. After either step 1220 or 1222 the process 1014 is ended and the processor 12 continues execution of the process which called process 1014.

Figure 35A:
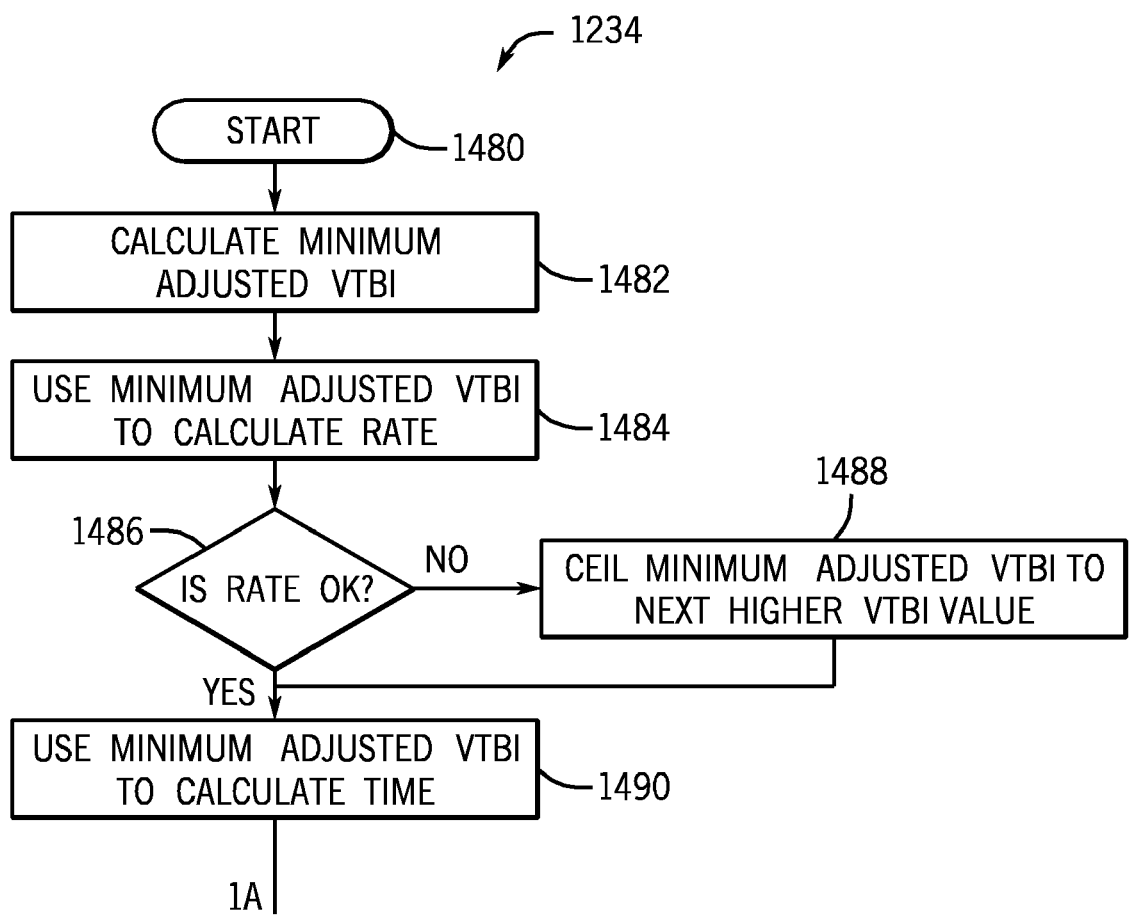
FIG. 35A is the initial portion of a flowchart of a process that calculates the adjusted valid range for VTBI without any existing rate or time.
Figure 35B:
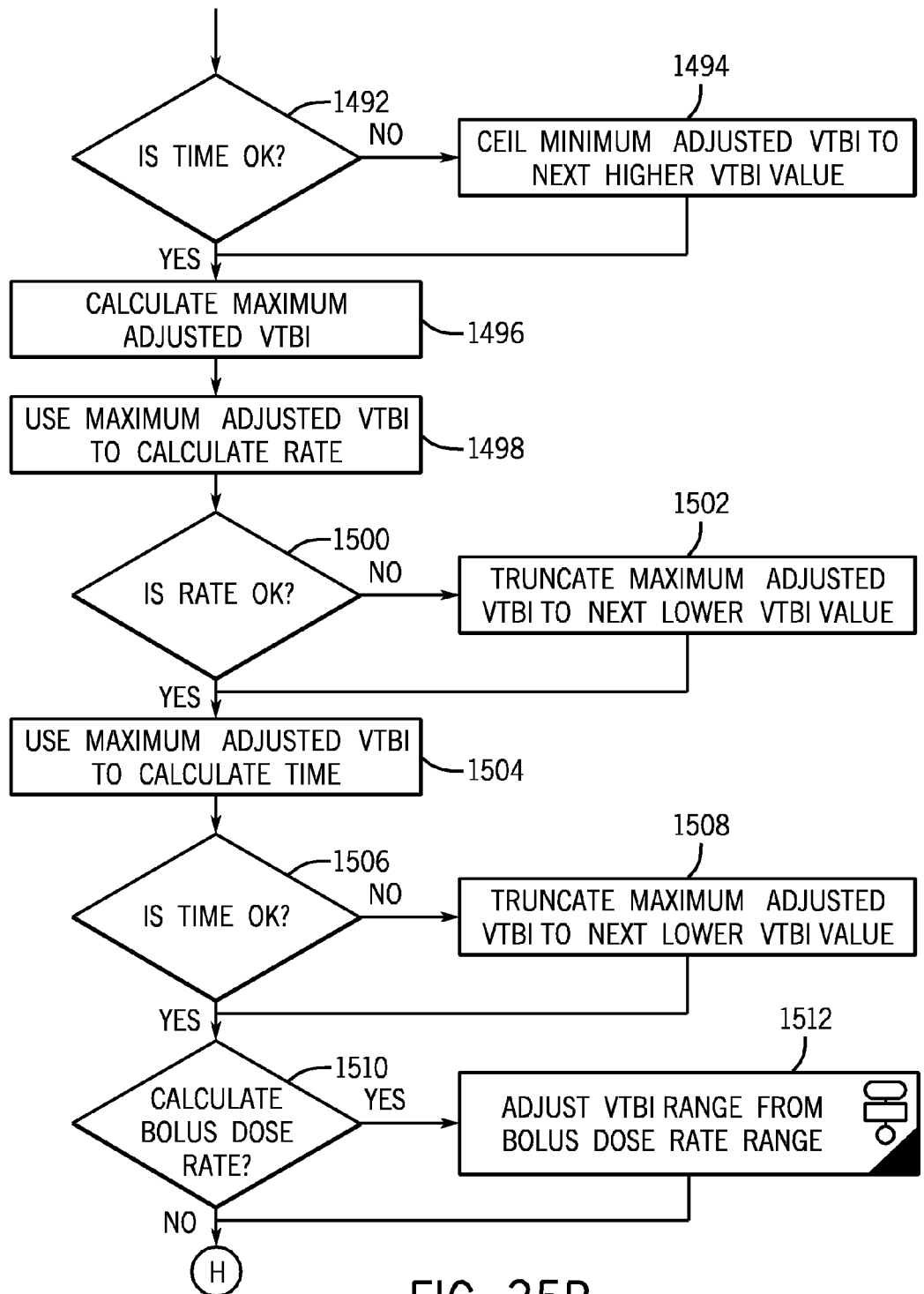
FIG. 35B is a continuation of the flowchart of FIG. 35A and shows the remaining portion of a process that calculates the adjusted valid range for VTBI without any existing rate or time.
Figure 36:
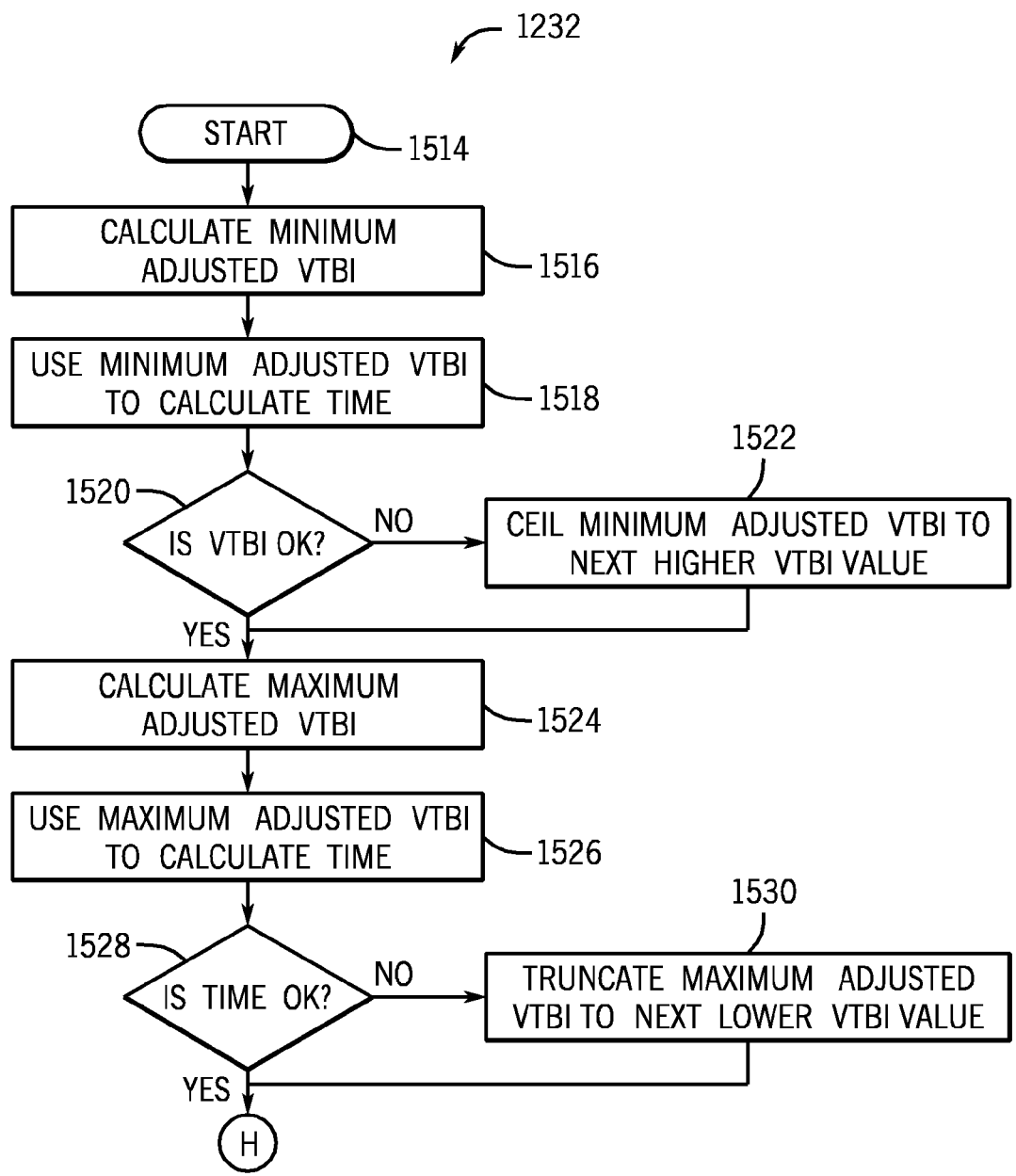
FIG. 36 is a flowchart of a process that calculates the adjusted valid range for VTBI with an existing rate such that time is calculated once the new VTBI is entered.
Figure 37:
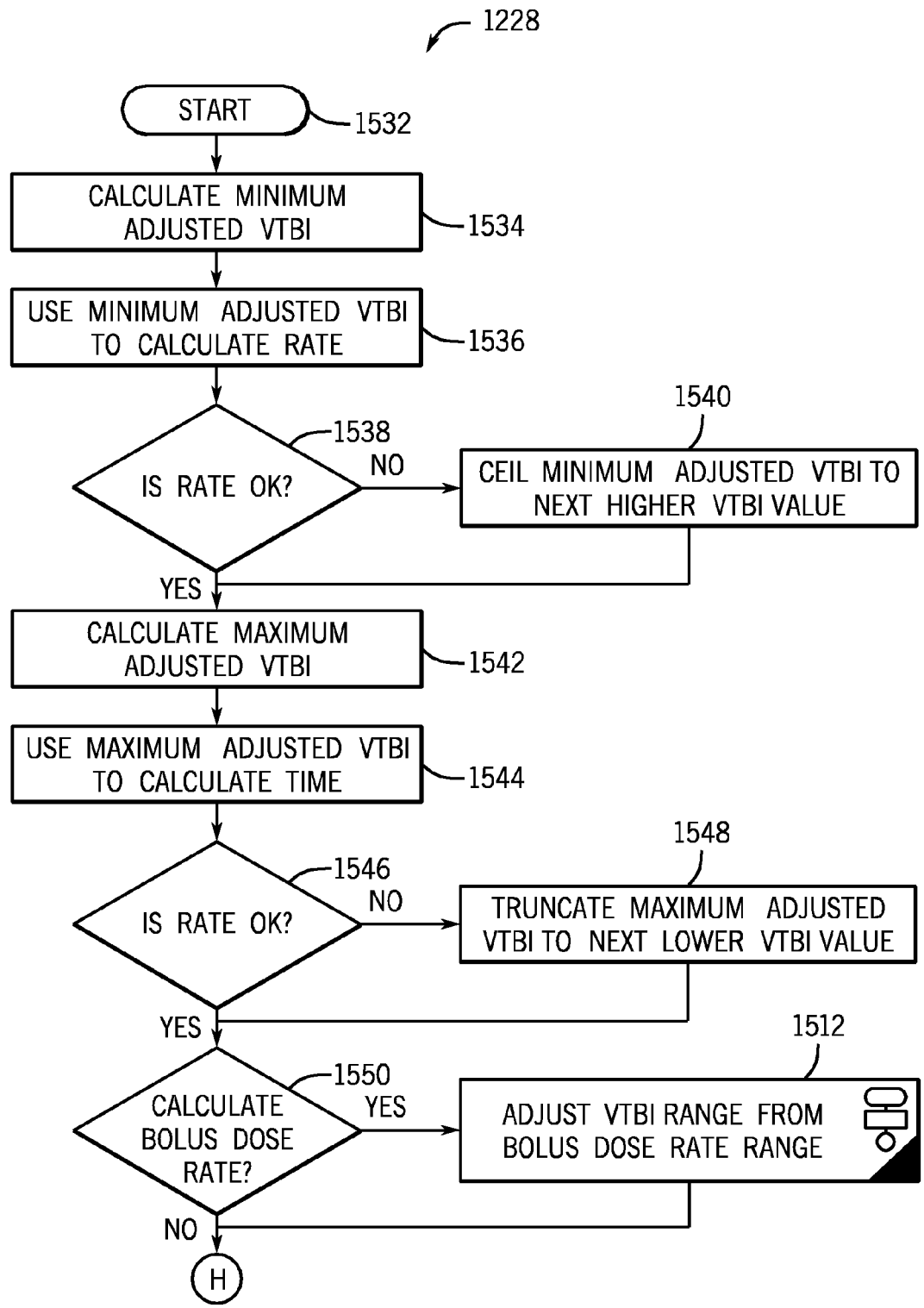
FIG. 37 is a flowchart of a process that calculates the adjusted valid range for VTBI with an existing time such that rate is calculated once the new VTBI is entered.

FIG. 25 shows a process 1032 for calculating an adjusted valid range for VTBI (volume to be infused). After starting at step 1124 a determination is made whether or not rate is to be calculated once a new VTBI is entered at step 1226. If rate is to be calculated then the valid range of the VTBI is adjusted with existing time information at step 1228 (FIG. 37). If rate is determined not to be calculated once a new VTBI is entered at step 1126 the processor 12 will determine if time is to be calculated once a new VTBI is entered at step 1230. If time is to be calculated then the valid range of the VTBI will be adjusted with the existing rate at step 1232 (FIG. 36). If time is determined not to be calculated once a new VTBI is entered at step 1230 the valid range for the VTBI will be adjusted without any known rate or time at step 1234 (FIG. 35).

Figure 34:
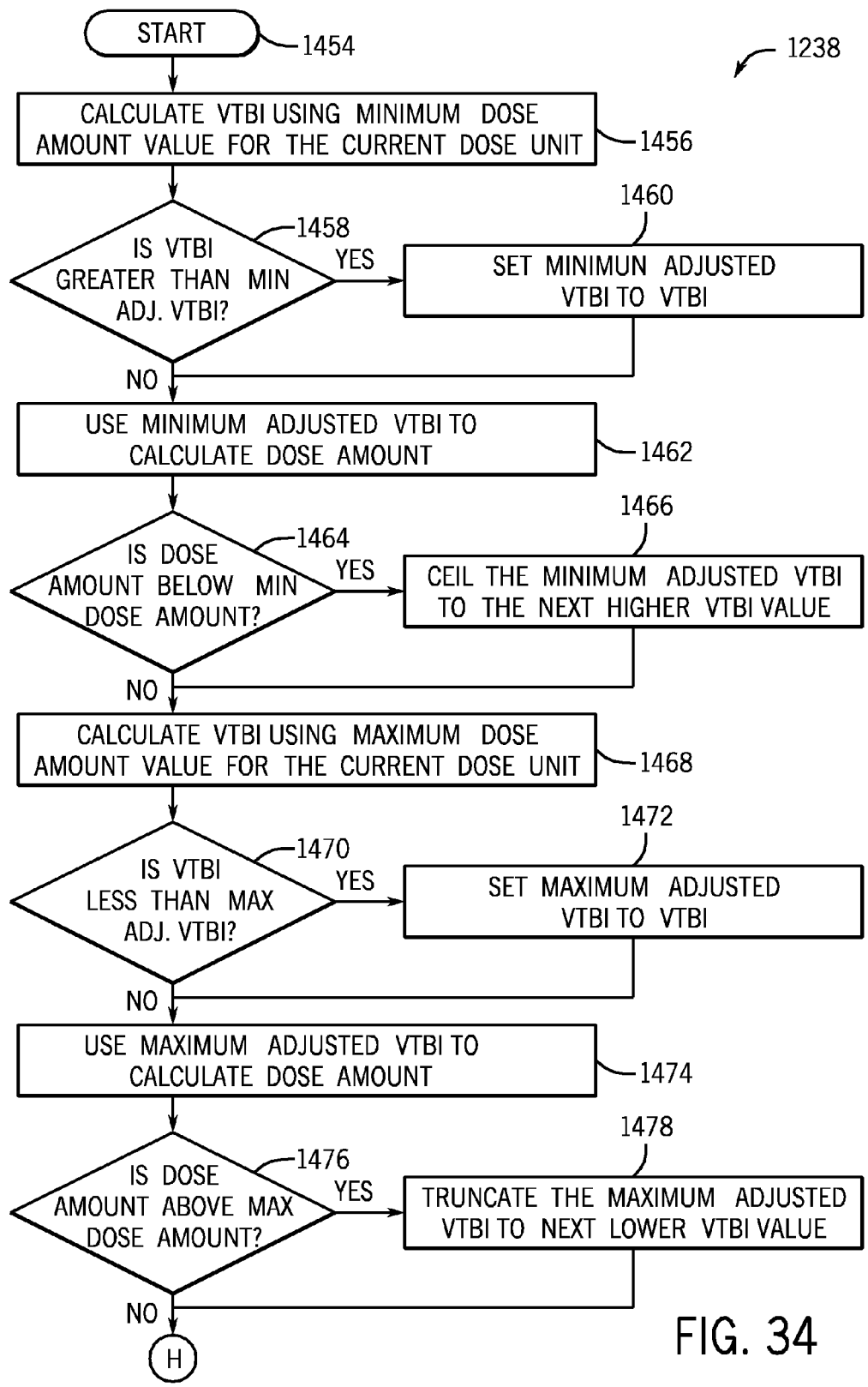
FIG. 34 is a flowchart of a process that calculates the adjusted valid range for VTBI from a dose amount range.

Once a valid range for the VTBI has been adjusted in either step 1128, 1232, or 1234 the processor 12 makes a determination whether the dose amount is to be back calculated once a new VTBI is entered at step 1236. If the dose amount is to be back calculated the adjusted valid range for VTBI will again be adjusted taking into account the dose amount range at step 1238 (FIG. 34). Once readjusted at step 1238 or if a the dose amount is determined not to be back calculated once a new VTBI is entered at step 1236 the process then uses the most stringent valid range limitations in regard to the adjusted valid range, machine limitations, and configurable limits at step 1240. Once the most stringent valid range limits are used the processor 12 determines if there is a valid range at step 1242. If there is a valid range that valid range is considered the new adjusted valid range for VTBI and is returned and/or stored in the memory 24 at step 1244 whereas if there is not a valid range that means that there is no valid VTBI to be entered and that information is returned and/or stored in the memory 24 at step 1246. After either step 1244 or 1246 the process 1032 is ended and the processor 12 continues execution of the process which called process 1032.

Figure 39A:
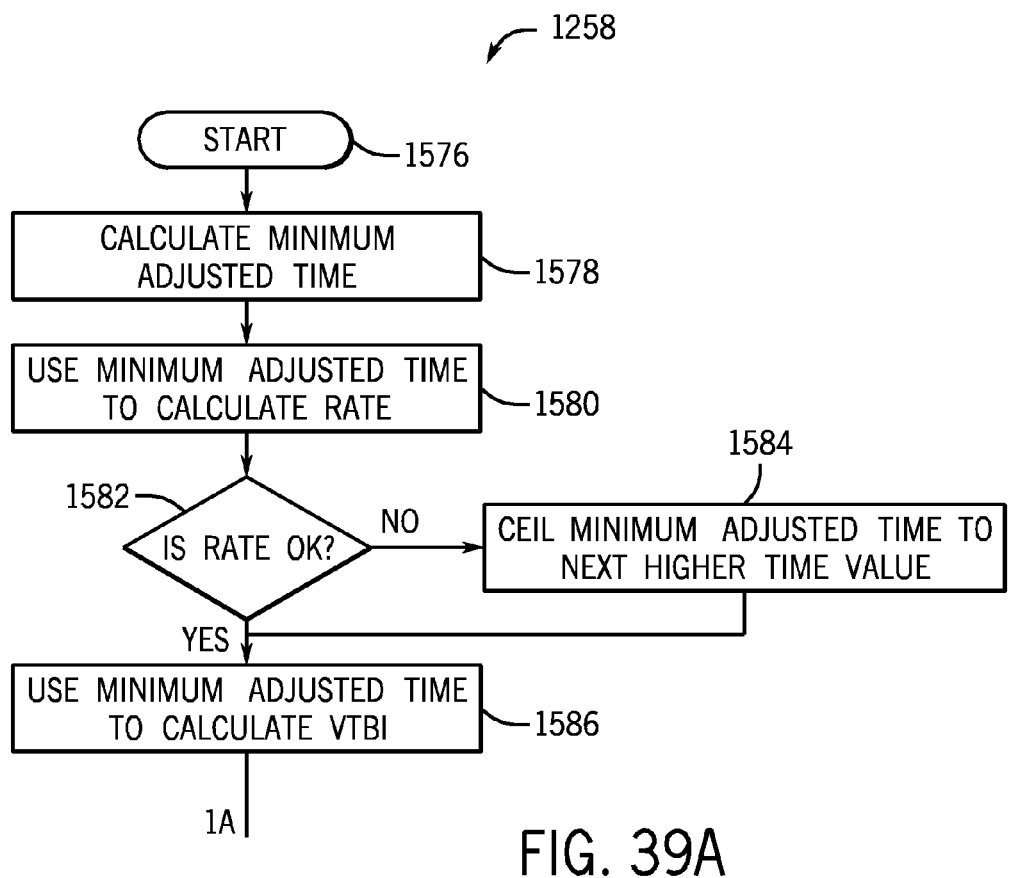
FIG. 39A is the initial portion of a flowchart of a process that calculates the adjusted valid range for time without having an existing rate of VTBI.
Figure 39B:
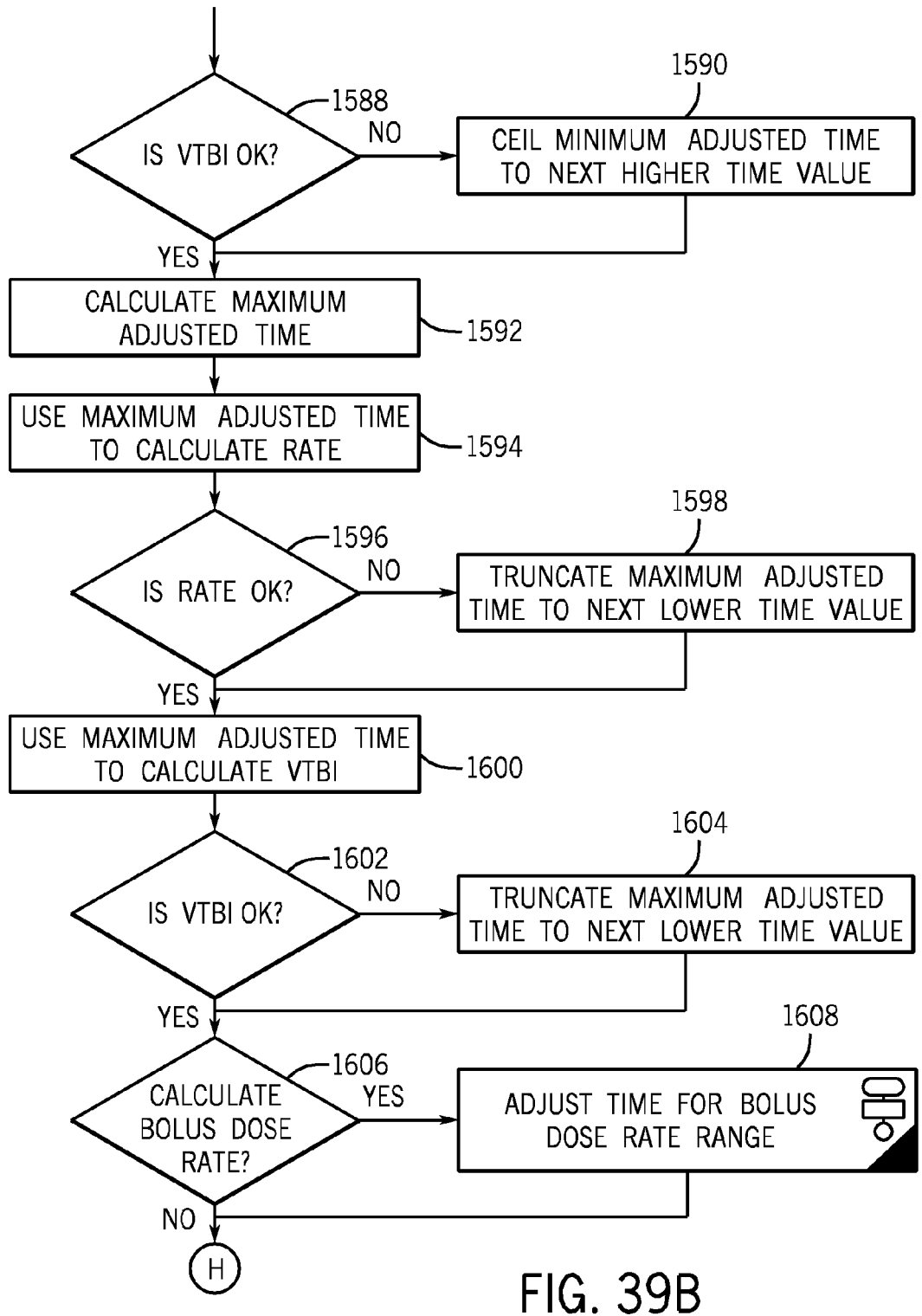
FIG. 39B is a continuation of the flowchart of FIG. 39A and shows the remaining portion of a process that calculates the adjusted valid range for time without having an existing rate of VTBI.
Figure 40:
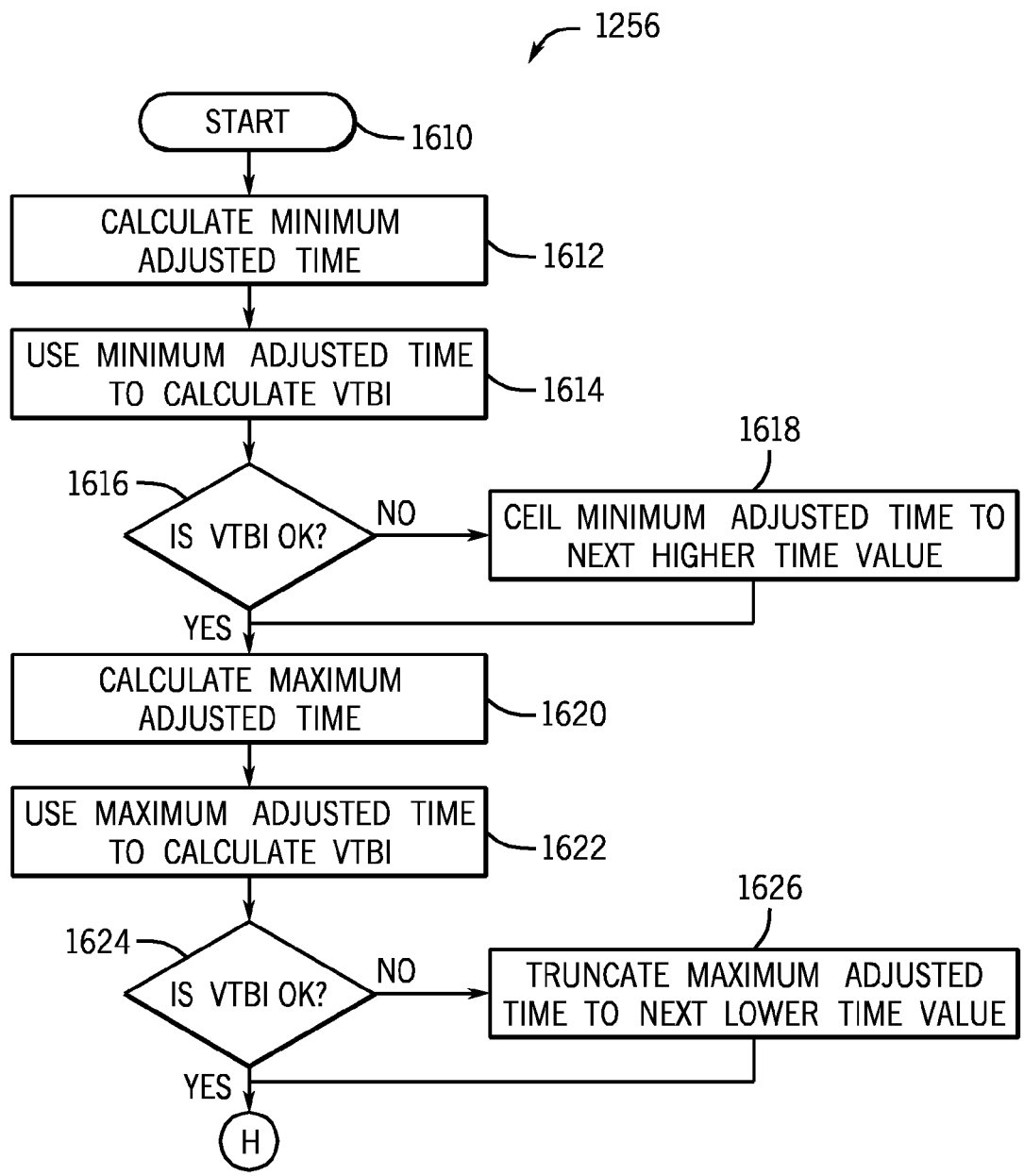
FIG. 40 is a flowchart of a process that calculates the adjusted valid range for time when having an existing rate wherein VTBI is calculated once the new time is entered.
Figure 41:
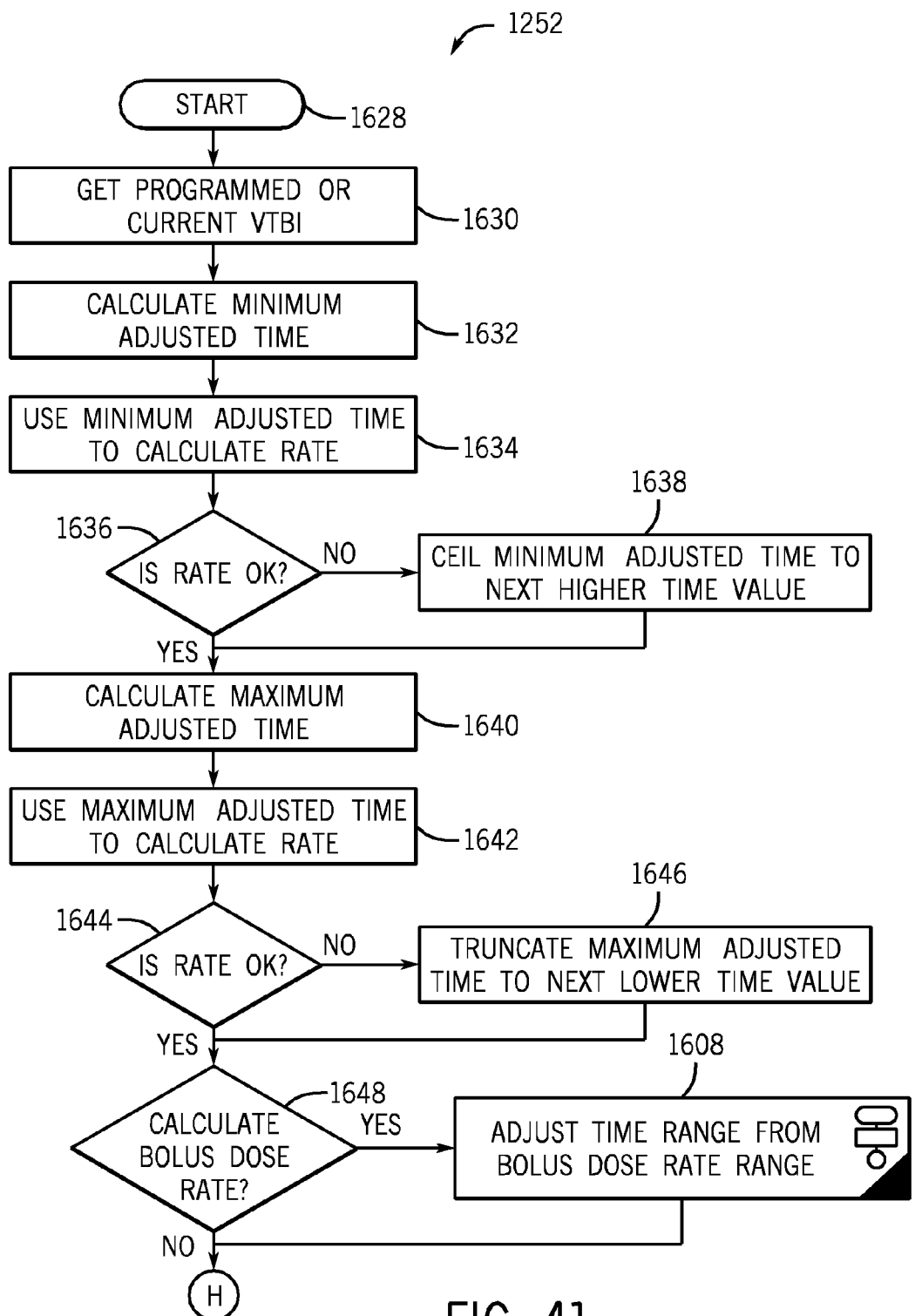
FIG. 41 is a flowchart of a process that calculates the adjusted valid range for time when having an existing VTBI such that a rate is calculated once the new time is entered.

FIG. 26 shows process 1104 for calculating the adjusted valid range of time 116. After starting at step 1248 the process involves first determining whether rate is to be calculated once a new time is entered at 1250. If rate is to be calculated, the processor 12 will adjust the valid range for time with the existing VBTI (volume to be infused) at step 1252 (FIG. 41). If the rate is determined not to be calculated once the new time is entered the processor 12 will then determine if VTBI is to be calculated once a new time is entered at step 1254. If VTBI is to be calculated, then the valid range of time will be adjusted in with the existing rate at step 1256 (FIG. 40). If VTBI is determined not to be calculated once a new time is entered at step 1254 then the valid range for time will be adjusted without any known rate or VTBI at step 1258 (FIG. 39).

Once the valid range for time is adjusted in one of the previous steps 1252, 1256, or 1258 the processor 12 then uses the most stringent valid range provided when accounting for the adjusted valid range, machine limitations, and configurable limits at step 1260. The process then requires the processor 12 to determine if there is a valid range at step 1262. If there is a valid range that valid range is considered to be the new adjusted valid range for time and is returned and/or stored in the memory 24 at step 1264 whereas if there is no valid range that means that there is no valid time to be entered and that information returned and/or stored in memory 24 at step 1266. After either step 1264 or 1266 the process 1104 is ended and the processor 12 continues execution of the process which called process 1104.

FIG. 27 shows process 1146 for calculating the adjusted valid range for weight when the dose is weight based and hence weight is part of the dose calculation. When starting at step 1268 the process 1146 first requires that the processor 12 determine if there is a dose entered at step 1270. If a dose is entered at step 1272 the entered dose is used in later calculations whereas if there is not a dose entered then a dose range at step 1274 is used in later calculations instead. At this time at step 1276 using either the entered dose or a dose range, a dose calculation equation is back calculated to get a weight range.

Once a weight range is back calculated the processor 12 then determines if there is a valid weight range at step 1278.

If there is, the next step is to calculate, using rounding, the rate (dose rate therapies) or VTBI (dose amount therapies) using the lower limit value of the adjusted valid range of weight at step 1280. At that time, the processor 12 determines if the rate or VTBI is proper at step 1282 and if not, at step 1284, the lower limit value of the adjusted valid range for weight is ceiled to the next higher value. Upon ceiling the lower limit at step 1284 or determining that the rate or VTBI is proper at step 1282 the upper limit value of the valid range for weight is used to calculate, using rounding, the rate or VTBI at step 1286. Then at step 1288 the processor 12 determines if the rate or VTBI is proper. If not, the upper limit value of the adjusted valid range for weight is truncated to the next lower value at step 1290. Either after the rate or VTBI is determined proper in step 1288 or the upper adjusted limit value for weight is truncated at step 1290 the valid range values are then considered the new adjusted valid range values for weight and returned and/or stored in memory at step 1292. In contrast, if at step 1278 there was no valid weight range the processor 12 will return and/or store in its memory that there is not a valid range of values as provided in step 1294 which means that there are no valid weight values to be entered. After either step 1292 or 1294 the process 1146 is ended and the processor 12 continues execution of the process which called process 1146.

FIGS. 28A and 28B show a process 1148 wherein the adjusted valid range for weight is calculated from a BSA (body surface area) range. Thus, the dose unit is BSA based and modifying the weight may calculate the BSA. After starting at step 1296 the adjusted valid range for BSA is calculated at step 1088 (FIG. 23). The processor 12 then determines if there is a valid BSA range at step 1298. If there is a valid BSA range then at step 1300 the processor 12 determines if there is a height 106 entered. If a height 106 is entered then at step 1302 that entered height will be used in later calculations whereas if a height is not entered then at 1304 the height range will be used during later calculations. Then at step 1306 by using either the entered height of 1302 or the height range of 1304 a BSA calculation equation is back calculated to determine a weight range.

The process 1148 then requires the processor 12 to determine whether the weight range of 1306 is a valid weight range at step 1308. If there is a valid weight range at 1308 then at step 1310 the BSA is calculated, using rounding, using the lower limit value of the adjusted valid range for weight. Once BSA is calculated at 1312 the processor 12 determines if the BSA value is proper. If the BSA is not proper then the lower limit value of the adjusted valid range for weight is ceiled to the next higher value at step 1314. After the BSA is found proper or the lower limit value of the adjusted valid range for weight is ceiled, BSA is calculated, using rounding, using the upper limit value of the adjusted valid range for weight at step 1316. At step 1318 this BSA is checked to determine if it is proper or not. If not, the upper limit value of the adjusted valid range for weight will be truncated to the next lower value at step 1320.

Once a proper BSA is found at step 1318 or the adjusted valid range for weight is truncated at step 1320 the adjusted valid range for weight is returned and/or stored in the memory 24 of the processor 12 at step 1322. If during the process 1148 the processor 12 determines that there is not a valid BSA range at step 1298 or that there is not a valid weight range at step 1308 the fact no valid range values exist is instead returned and/or stored in the memory 24 by the processor at step 1324. After either step 1322 or 1324 the process 1148 is ended and the processor 12 continues execution of the process which called process 1148.

FIGS. 29A and 29B show a process 1160 for adjusting the valid range for height from a BSA (body surface area) range. Thus the dose unit is BSA (body surface area) based and modifying height may calculate the BSA. After starting at step 1326 the adjusted valid range for BSA is calculated at step 1088 (FIG. 23). The processor 12 then determines if there is a valid BSA range at step 1298. If there is a valid BSA range then at step 1328 the processor 12 then determines if there is a weight entered at step 1328. If a weight is entered the processor 12 will use the entered weight in later calculations in step 1330, however, if a weight is not entered then the processor 12 uses the weight range in later calculations as indicated in step 1332. Once the processor 12 determines whether an entered weight or a weight range is to be used, the processor 12 back calculates the BSA calculation equation to get a height range in step 1334.

Once calculating the height range in step 1334 the process 1160 then determines if the height range is valid at step 1336. If the height range is valid then at step 1138 a BSA is calculated using the lower limit value of the adjusted valid range for height. Then in step 1340 the processor 12 determines if that calculated BSA is proper and if not, the processor 12 ceils the lower limit value of the adjusted valid range for height to the next higher value at step 1342.

Either after the BSA was determined proper or the lower limit value was ceiled to the next higher value the processor 12 then calculates BSA using the upper adjusted valid range value for height at step 1344. Again, this BSA is checked at step 1346 and if not proper, the upper limit value of the adjusted valid range for height is truncated to the next lower value at step 1348. Thus, once the processor 12 determines if the upper and lower limit values of the height range need to be ceiled or truncated, the adjusted valid range for height is returned and/or stored within the memory 24 at step 1350. If, in step 1298 the processor 12 determines there is not a valid adjusted BSA (body surface area) range, or in step 1336 the processor 12 determines there is not a valid height range this information is returned and/or stored in memory 24 at step 1352. After either step 1350 or 1352 the process 1160 is ended and the processor 12 continues execution of the process which called process 1160.

FIG. 30 shows process 1210 for adjusting the valid range for rate from the dose rate range. After starting at step 1354 the processor 12 calculates a rate using the minimum dose rate value for the current dose unit at step 1356. Then, at step 1358 a determination is made whether or not the calculated rate is greater than the minimum adjusted rate value. If the calculated rate is greater then at step 1360 the minimum adjusted valid range value is set to the rate calculated in step 1356. In step 1362 the minimum adjusted range value for rate is used to calculate a dose rate.

In step 1364 there is a determination made if the dose rate calculated in step 1362 is below the minimum dose rate value. If so, the minimum adjusted valid range value for rate is set to the next higher rate value in step 1366. Once a proper minimum valid range value for rate is determined in either step 1364 or 1366 the processor 12 then calculates rate using the maximum dose rate value for the current dose unit at step 1368. If the rate calculated in 1368 is less than the maximum adjusted valid range for rate as determined in 1370, the maximum adjusted valid range value for rate is set to the calculated rate in step 1372.

The lower adjusted range value for rate then is used to calculate dose rate at step 1374. The processor 12 then determines at step 1376 if the dose rate calculated at step 1374 is above the maximum dose rate value for the current dose unit. If so, the maximum valid range value for rate is set to the next lower rate value at step 1378. After either step 1376 or 1378 the process 1210 is ended and the processor 12 continues execution of the process which called process 1210.

FIG. 31 shows the process 1206 for adjusting the valid range for rate without any existing VTBI 114 (volume to be infused) or time 116, i.e. neither VTBI nor time will be calculated once the new rate is entered. After starting at step 1380 the processor 12 calculates the minimum adjusted valid range value for rate at step 1382. This minimum value is then used to calculate VTBI at step 1384. Then the processor 12 determines in step 1386 whether the VTBI is proper. If the VTBI of step 1386 is not considered proper the minimum adjusted valid range value for rate is ceiled to the next higher rate value at step 1388.

Once the calculated VTBI of 1384 is used to determine if the minimum adjusted valid range value for rate needs to be ceiled the processor 12 then uses the minimum adjusted valid range value for rate to calculate time 116 at step 1390. The processor 12 then determines at step 1392 whether the time calculated in step 1390 is proper. If not, the minimum adjusted valid range value for rate is ceiled to the next higher rate value at step 1394.

After the time calculation and adjustments of steps 1392 and 1394 the processor 12 then calculates a maximum value for the adjusted valid range for rate at step 1396. At step 1398 this calculated maximum value for rate is used to calculate VTBI (volume to be infused). Once VTBI is calculated using the maximum value for rate the processor 12 determines if the VTBI is proper at step 1400. If not, at step 1402 the processor 12 truncates the maximum adjusted valid range value for rate to the next lower rate value.

In step 1404 the processor 12 similarly uses the maximum adjusted valid range value for rate to calculate time 116. Then using the time calculated in step 1404 the processor 12 determines in step 1406 whether this time falls within the valid range for time. If not, at step 1408 the processor 12 truncates the maximum adjusted valid range value for rate to the next lower rate value. After either step 1406 or 1408 the process 1206 is ended and the processor 12 continues execution of the process which called process 1206.

FIG. 32 provides process 1204 for adjusting the valid range for rate using an existing VTBI (volume to be infused). As such, time is calculated from the existing VTBI and the new rate once a new rate is entered. After starting at step 1410 the programmed or current VTBI is retrieved at step 1412. At this time the processor 12 calculates a minimum adjusted valid range value for rate at step 1414. At step 1416 the processor 12 uses the calculated minimum adjusted valid range value for rate to calculate time 116. Then at step 1418 a determination is made regarding the calculated time and whether it falls within the valid range for time. If the calculated time does not fall within the valid range then the minimum adjusted valid range value is ceiled to the next higher rate value at step 1420.

Once the decision is made regarding whether the calculated time is correct or whether the minimum rate range value limit needed to be ceiled in steps 1418 and 1420 is complete the processor 12 then calculates the maximum adjusted valid range value for rate at step 1422. Once calculated the processor 12 at 1424 uses the maximum adjusted valid range value for rate to again calculate time. Then a determination again is made at 1426 whether the time is proper. If not, the maximum adjusted valid range value for rate is truncated to the next lower rate value at step 1428. After either step 1426 or 1428 the process 1204 is ended and the processor 12 continues execution of the process which called process 1204.

FIG. 33A shows a process 1200 for adjusting the valid range of rate with an existing time 116 such that VTBI (volume to be infused) is calculated from the existing time and the new rate once a new rate is entered. In the process after the start at step 1430 the processor 12 calculates a minimum adjusted valid range value for rate at step 1432. The processor 12 then uses that calculated value of 1432 to calculate VTBI at step 1434. A determination at 1436 is then made regarding whether the VTBI is proper. If the VTBI of step 1436 is not proper the minimum limit value of the adjusted valid range for rate is ceiled to the next higher rate value at step 1438.

After determining the VTBI is proper or after the minimum limit value is ceiled the processor 12 then calculates a maximum limit value for the adjusted valid range for rate at 1440. At 1442 this maximum adjusted valid range value for rate is used to calculate VTBI. Then at step 1444 the processor 12 determines if the VTBI is correct and if not, truncates the maximum adjusted valid range value for rate to the next lower rate value at 1446. After either step 1444 or 1446 the process 1200 is ended and the processor 12 continues execution of the process which called process 1200.

Figure 43A:
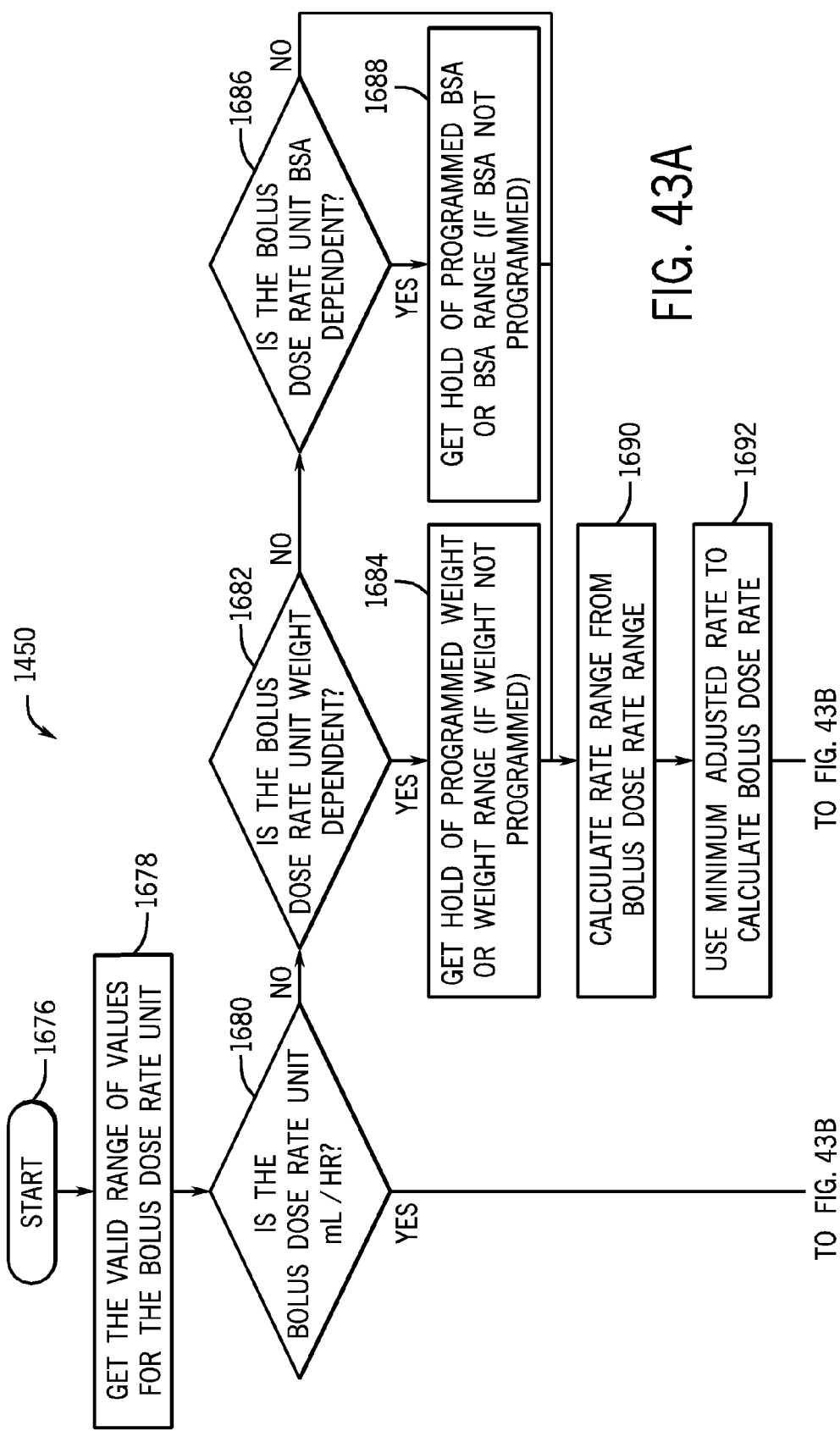
FIG. 43 is a flowchart of a process that calculates the adjusted valid range for rate from a bolus dose rate range.
Figure 43B:
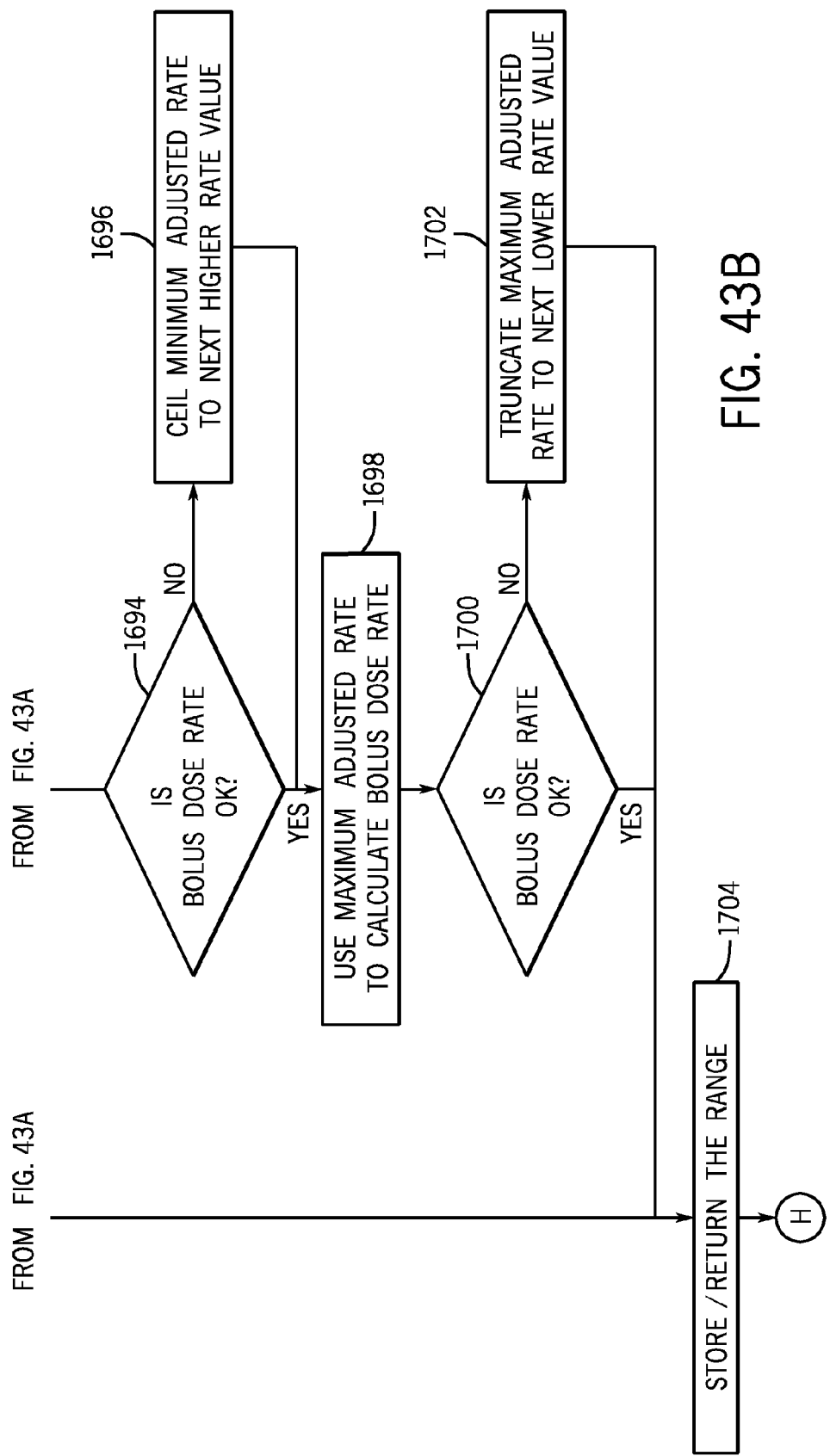

FIG. 33B shows the process 1214 for adjusting the valid range for rate from the bolus dose rate range. After starting at step 1448 the processor 12 calculates a valid rate range from the bolus dose rate range at step 1450 (FIG. 43). Then, at step 1452 the processor 12 uses the most stringent range of the valid rate range and the adjusted valid range for rate as a new adjusted valid range for rate. After step 1452 the process 1214 is ended and the processor 12 continues execution of the process which called process 1214.

FIG. 34 shows the process 1238 for adjusting the valid range of VTBI (volume to be infused) from the dose amount range for the current dose amount unit. After starting at step 1454 the processor 12 calculates VTBI using the minimum dose amount range value for the current dose unit at step 1456. At step 1458 the processor 12 determines if the VTBI is greater than the minimum adjusted VTBI value. If yes, the minimum adjusted valid range value for VTBI is set to the calculated VTBI of step 1456 at step 1460. Then at step 1462 the minimum adjusted valid range value for VTBI is used to calculate a dose amount. Once the dose amount is calculated at step 1464 the processor 12 determines if the dose amount is below the present minimum dose amount value. If so, the minimum adjust valid range is set to the next higher level of VTBI at step 1466.

At step 1468 a VTBI is calculated using the maximum dose amount value for the current unit dose. As such, at step 1470 the processor 12 determines if the VTBI is less than the maximum adjusted VTBI value. If it is, then the maximum adjusted valid range value for VTBI is set to the calculated VTBI of step 1468 at step 1472. Then the maximum range value for VTBI is used to calculate a dose amount at step 1474. At step 1476 the processor 12 determines if the calculated dose amount is above the maximum dose amount value. If it is, the maximum adjusted valid range value is set to the next lower VTBI at step 1478. After either step 1476 or 1478 the process 1238 is ended and the processor 12 continues execution of the process which called process 1238.

FIG. 35 shows the process 1234 for adjusting the valid range of VTBI without using any existing rate or time, i.e. neither rate nor time will be calculated once a new VTBI is entered. After starting at step 1480 the processor 12 calculates the minimum adjusted valid range value for VTBI at step 1482. This calculated VTBI value is then used to calculate rate at step 1484. At step 1486 the processor 12 determines if the rate is proper. If not, the minimum adjusted valid range value for VTBI is ceiled to the next higher VTBI value at step 1488. At that time the processor 12 uses the minimum adjusted valid range value for VTBI to calculate time at 1490.

The processor then determines at step 1492 if the time is proper and if not, ceils the minimum adjusted valid range value for VTBI to the next higher VTBI value at step 1494.

Next, the processor 12 calculates the maximum adjusted valid range value for VTBI at step 1496. This maximum adjusted valid range value for a VTBI is then used to calculate rate at 1498. The processor 12 determines if the rate is proper at step 1500 and if not, truncates the maximum adjusted valid range value for VTBI to the next lower VTBI value at step 1502.

Figure 38:
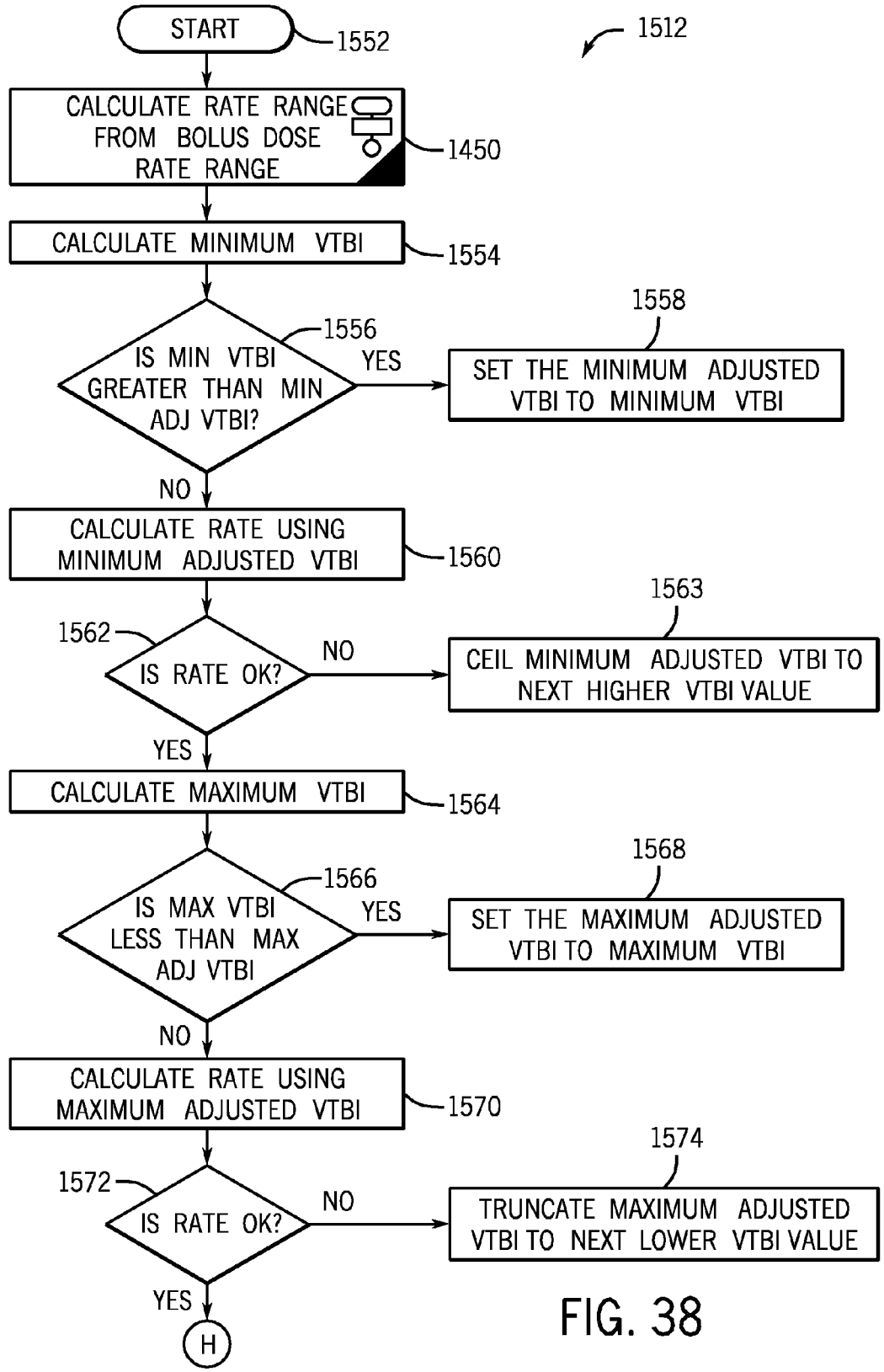
FIG. 38 is a flowchart of a process that calculates the adjusted valid range for VTBI from a bolus dose rate range.

The processor 12 then takes the maximum adjusted range value for VTBI to calculate time at 1504. At step 1506 the processor 12 determines if the time is proper and if not, the maximum adjusted valid range value for VTBI is truncated to the next lower VTBI value at step 1508. The processor 12 then determines if the bolus dose rate is to be calculated once a new VTBI is entered at step 1510 and if it is, the valid range for VTBI is adjusted from the bolus dose rate range at step 1512 (FIG. 38). After either step 1510 or 1512 the process 1234 is ended and the processor 12 continues execution of the process which called process 1234.

FIG. 36 shows the process 1232 for adjusting the valid range for VTBI with an existing rate such that time is calculated from the existing rate and the new VTBI once the new VTBI is entered. After starting at step 1514 the processor 12 calculates the minimum adjusted valid range value for VTBI at step 1516. The processor 12 then uses this calculated value to calculate time at step 1518. The processor 12 at step 1520 then determines if time is proper and if not, the minimum adjusted valid range value for VTBI is ceiled to the next higher VTBI value at step 1522.

The processor 12 at step 1524 calculates a maximum adjusted valid range value for VTBI. Then at step 1526 that maximum adjusted valid range value for VTBI is used to calculate time. The processor 12 next determines if the calculated time is proper at step 1528. If the time is not proper the maximum adjusted valid range value for VTBI is truncated to the next lower VTBI value at step 1530. After either step 1528 or 1530 the process 1232 is ended and the processor 12 continues execution of the process which called process 1232.

FIG. 37 shows a process 1228 for adjusting the valid range for VTBI with an existing time such that rate is calculated from the existing time and the new VTBI once a new VTBI is entered. Upon starting at step 1532 the processor 12 calculates the minimum adjusted valid range value for VTBI at step 1534. This value is then used to calculate rate at 1536. At step 1538 the processor 12 determines if the calculated rate is proper and if not, the minimum adjusted valid range value for VTBI is ceiled to the next higher VTBI value at step 1540.

Next the processor 12 calculates the maximum adjusted valid range value for VTBI at step 1542. At step 1544 the processor 12 uses the calculated maximum adjusted valid range value for VTBI to calculate rate. At step 1546 the processor 12 determines if the rate is proper and if not, the maximum adjusted valid range value for VTBI is truncated to the next lower VTBI value at step 1548. Next, the processor 12 determines if a bolus dose rate is to be calculated once a new VTBI is entered at step 1550 and if so, the processor 12 adjusts the valid range for VTBI from the bolus dose rate range at step 1512 (FIG. 38). After either step 1550 or 1512 the process 1228 is ended and the processor 12 continues execution of the process which called process 1228.

FIG. 38 shows a process 1512 for adjusting the valid range for VTBI (volume to be infused) from the bolus dose rate range. After starting with step 1552 the processor 12 calculates a rate range from the bolus dose rate range at step 1450 (FIG. 43). The processor 12 then calculates the minimum VTBI at step 1554 and determines if the minimum VTBI is greater than the minimum adjusted range value for VTBI at step 1556. If the minimum VTBI is greater than the minimum adjusted range value for VTBI then the minimum adjusted valid range value for VTBI is set to the minimum VTBI at step 1558.

Next, the processor 12 calculates rate using minimum adjusted valid range value for VTBI at step 1560. At step 1562 the processor 12 determines if the rate is proper and if not, the minimum adjusted valid range value for VTBI is set to the next higher VTBI.

The next step 1564 involves the processor 12 calculating the maximum VTBI. Then the processor 12 determines at step 1566 if the maximum VTBI is less than the maximum adjusted range value for VTBI. If the maximum VTBI is less than the maximum adjusted range value for VTBI then the maximum adjusted valid range value for VTBI is set to the maximum VTBI at step 1568. Then using the maximum adjusted valid range value for VTBI the processor 12 calculates rate at step 1570. The processor 12 then determines if the rate is proper at step 1572 and if not, the maximum adjusted valid range value for VTBI is set to the next lower maximum VTBI at step 1574. After either step 1572 or 1574 the process 1512 is ended and the processor 12 continues execution of the process which called process 1512.

FIG. 39 provides the process 1258 used to adjust the valid range of time 116 without any existing rate or VTBI, i.e. neither rate nor time will be calculated once a new time is entered. After starting at step 1576 the processor 12 calculates a minimum adjusted valid range value for time at step 1578. The processor 12 then uses the calculated value of 1578 to calculate rate at step 1580. The processor 12 then determines if the rate is proper at step 1582 and if not, the minimum adjusted valid range value for time 116 is ceiled to the next higher time value at step 1584. The minimum adjusted valid range value for time is then used to calculate VTBI at step 1586. The processor 12 then determines at step 1588 if this calculated VTBI is proper and if not, the minimum adjusted valid range value for time is ceiled to the next higher time value at step 1590.

The processor 12 then calculates a maximum adjusted valid range value for time at step 1592. The processor 12 then uses the calculated value of 1592 to calculate rate at step 1594. The processor 12 next determines at step 1596 if the rate is proper and if not, the maximum adjusted valid range value for time is truncated to the next lower time value at step 1598.

Figure 42:
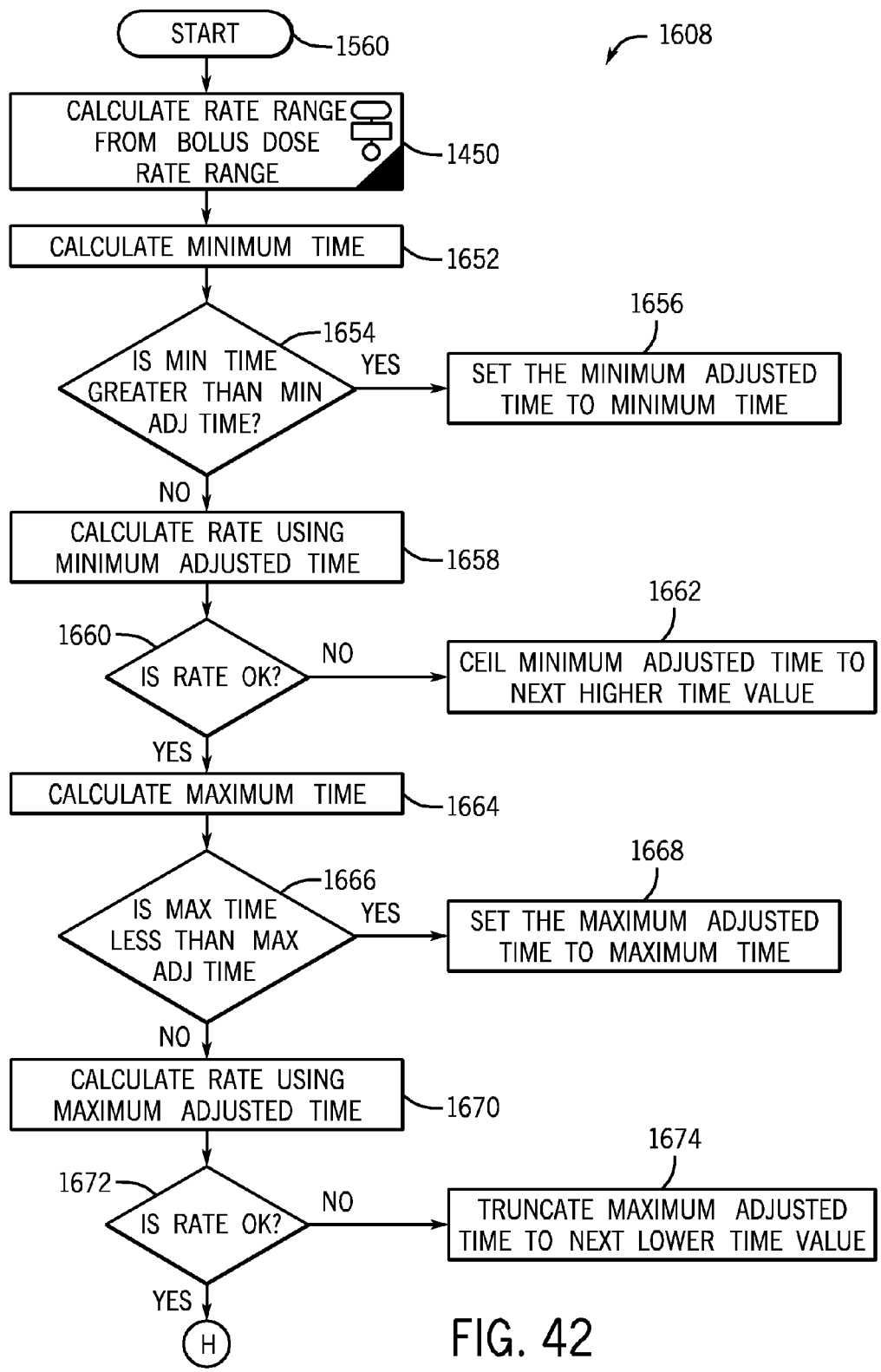
FIG. 42 is a flowchart of a process that calculates the adjusted valid range for time from a bolus dose rate range.

The processor 12 uses the maximum adjusted valid range value for time to calculate VTBI at step 1600. The processor 12 then determines if the VTBI calculated in steps 1600 is proper at step 1602. If not, the maximum adjusted valid range value for time is truncated to the next lower time value at step 1604. Next, the processor 12 determines if the bolus dose rate is to be calculated once a new time is entered at step 1606 and if it is, the valid range for time is adjusted from the bolus dose rate range at step 1608 (FIG. 42). After either step 1606 or 1608 the process 1258 is ended and the processor 12 continues execution of the process which called process 1258.

FIG. 40 shows the process 1256 for adjusting the valid range of time 116 with an existing rate 112 such that VTBI 114 is calculated from the existing rate and the new time once a new time is entered. At the start step 1610 the processor 12 calculates the minimum adjusted valid range value for time at step 1612. The value calculated in step 1612 is then used to calculate VTBI at step 1614. The processor 12 at step 1616 determines if the calculated VTBI of step 1614 is proper and if not, ceils the minimum adjusted valid range value for time to the next higher time value at step 1618.

The processor 12 then calculates the maximum adjusted valid range value for time at step 1620 and uses this calculated value to calculate VTBI at step 1622. Then the processor 12 determines at step 1624 if the VTBI is proper. If not, the maximum adjusted valid range value for time is truncated to the next lower time value at step 1626. Thus, the process 1256 is ended and the processor 12 continues execution of the process which called process 1256.

FIG. 41 is the process 1252 for adjusting the valid range for time 116 with an existing VTBI 114 such that the rate 112 is calculated from the existing VTBI and the new time once a new time is entered. After the start at step 1628 the processor 12 retrieves the programmed or current VTBI at step 1630. The processor 12 then calculates the minimum adjusted valid range value for time at step 1632. Using the calculated value from step 1632 rate is calculated at step 1634. The processor 12 then determines if the rate is proper at step 1636 and if not, at step 1638 the minimum adjusted valid range value for time is ceiled to the next higher time value.

Next, the processor 12 calculates a maximum adjusted valid range value for time at step 1640. The processor 12 then uses the calculated value from step 1640 to calculate rate at step 1642. At step 1644 the processor 12 determines if the rate is proper and if not, the maximum adjusted valid range value for time is truncated to the lower time value at step 1646. The processor 12 additionally determines if the bolus dose rate is to be calculated once a new time is entered at step 1648 and if so, adjusts the valid range for time from the bolus dose rate range at step 1608 (FIG. 42). Thus, the process 1252 is ended and the processor 12 continues execution of the process which called process 1252.

FIG. 42 provides the process 1608 for adjusting the valid range for time 116 from the bolus dose rate range. Step 1650 starts the process and at step 1450 (FIG. 43) the processor 12 calculates a rate range from the bolus dose rate range. Then the processor 12 calculates a minimum time at step 1652. The processor 12 makes a determination at step 1654 regarding whether the minimum time is greater than the minimum adjusted valid range value for time. If so, the minimum adjusted valid range value for time is set to the minimum time as shown in step 1656. Then using the minimum adjusted valid range value for time the processor 12 calculates rate at step 1658. At step 1660 the processor 12 determines if the rate is proper and if not, the minimum adjusted valid range value for time is set to the next higher time value as shown in step 1662.

The processor 12 calculates a maximum time at step 1664. The processor 12 then determines if the maximum time is less than the maximum adjusted valid range value for time at step 1666 and if so, the maximum adjusted valid range value for time is set to the maximum time at step 1668. Rate is then calculated using the maximum adjusted valid range value for time at step at 1670. The processor 12 determines if the rate is proper at step 1672. If the rate is not proper, the maximum adjusted valid range value for time is set to the next lower time value at step 1674. Thus, the process 1608 is ended and the processor 12 continues execution of the process which called process 1608.

FIG. 43 shows the process 1450 for calculating a valid range for rate from the bolus dose rate range. After the start at step 1676 the processor 12 gets the valid range of values for the current bolus dose rate unit at step 1678. Then, the processor 12 determines if the bolus dose rate unit is ml/hr at step 1680. If not, the processor 12 then determines at step 1682 whether the bolus dose rate unit is weight dependent. If the bolus dose rate unit is weight dependent the processor 12 finds a programmed weight or the weight range if there is no weight present as shown in step 1684. If at step 1682 the bolus dose rate unit is not weight dependent then as shown in step 1686 the processor 12 determines if the bolus dose rate unit is BSA (body surface area) dependent. If it is, then the program accesses BSA or the BSA range if there is no BSA present at step 1688. Once either the weight, weight range, BSA, BSA range, or if the bolus dose rate unit is not based on either weight or BSA is determined the processor 12 calculates a rate range from the bolus dose rate range as provided in step 1690.

At step 1692 the minimum adjusted valid range value for rate is used to calculate a bolus dose rate. The processor 12 determines if the bolus dose rate is proper at step 1694. If the bolus dose rate is not proper in step 1694 the minimum adjusted valid range value for rate is ceiled to the next higher rate value at step 1696. The processor 12 then uses the minimum adjusted valid range value for rate to calculate a bolus dose rate in step 1698 and the processor 12 determines if this bolus dose rate is proper in step 1700. If not, the minimum adjusted valid range value for rate is ceiled to the next higher rate value at step 1702.

If the bolus dose rate unit is ml/hr at step 1680 the ml/hr range for bolus dose rate is then returned and/or stored at step 1704. Similarly, if the bolus dose rate is proper in step 1700 or if the valid range of the rate is adjusted in 1702 this range is returned and/or stored in step 1704. Thus, the process 1450 is ended and the processor 12 continues execution of the process which called process 1450.

Figure 44:
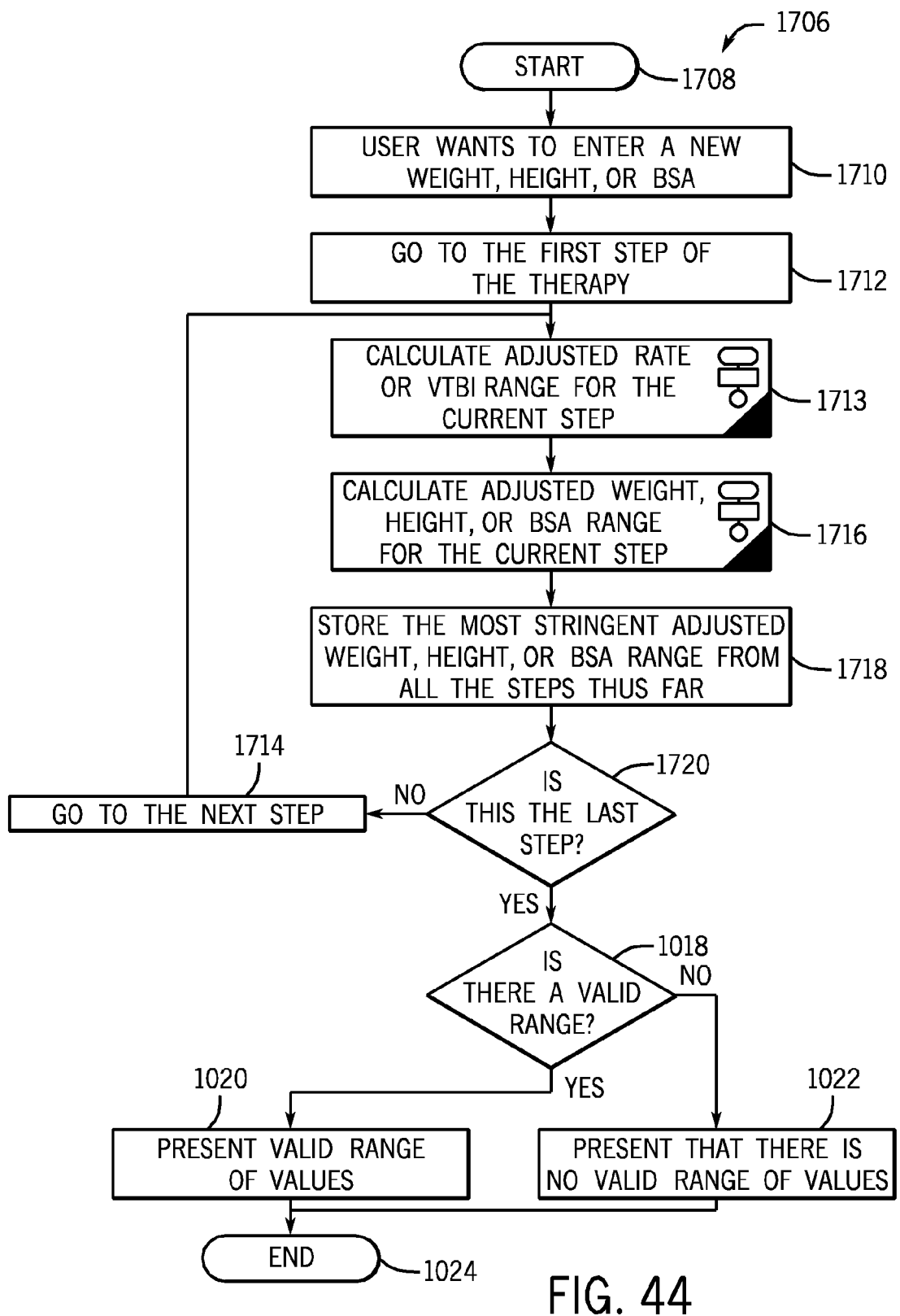
FIG. 44 is a flowchart of a process that calculates the adjusted valid range for a plurality of parameters when entering height, weight, or BSA as part of a multistep infusion therapy.

FIG. 44 provides a process 1706 that adjusts the valid range for weight, height, or BSA (body surface area) for therapies that have weight, height, or BSA common across multiple steps, e.g. a Multistep infusion therapy. Specifically, the process starts at step 1708 and at step 1710 the user desires to enter a new weight, height, or BSA (body surface area). At this time the process goes to the first step of the therapy at step 1712. The processor 12 then calculates the adjusted valid range for rate (dose rate therapies) or VTBI (dose amount therapies) using processes 1014 (dose rate therapies, FIG. 24) or 1032 (dose amount therapies, FIG. 25) at step 1713. At this point, the process calculates the adjusted valid range for weight, height, or BSA for the current step using processes 1048 (weight, FIG. 21), 1078 (height, FIG. 22), or 1088 (BSA, FIG. 23) at step 1716. Then, at step 1718 the most stringent weight, height, or BSA adjusted valid range values from the current and all the previous steps is stored. The minimum and maximum values may or may not be from the same step. The processor 12 at step 1720 must determine if the current step is the last step of the therapy. If not, the process 1706 goes to the next step of the therapy at step 1714 after which step 1713 will be executed again. If the current step is the last step of the therapy at step 1720, the processor 12 then determines if there is a valid range available at step 1018. If there is a valid range, the valid range is presented at step 1020 whereas if there is not a valid range this information is then presented to a user at step 1022. At this point in time the process has ended at step 1024.

Thus, disclosed is a system having a processor 12 that calculates and generates through an output device 18 a valid range of values for pump programming parameters based upon the constraints or other information entered by a user. This system allows for accurate data entry and additionally allows a user to know when and what exact information is being incorrectly entered when an error occurs. Additionally, the system has an array of calculations that can be made to constantly update and alter the valid range of values for the pump programming parameters based upon information provided. Thus, at the very least all of the stated objectives have been met.

It will be appreciated by those skilled in the art that other various modifications could be made to the device without departing from the scope of this invention. It will be appreciated by those skilled in the art that special infusion methods and their associated predetermined equations or considerations (not specifically identified herein) could be statically or dynamically back calculated according to this invention. Those special considerations include but are not limited to therapy limitations (e.g. a Multistep therapy may only deliver 1000 mL total instead of 1000 mL per step, or patient daily, weekly, or lifetime limitations on medication, etc), or new ways of entering pump programming parameters (e.g. total time, ramp up time, plateau time, and ramp down time considerations for Taper therapies). All such modifications and changes fall within the scope of the claims and are intended to be covered thereby.

What is claimed is:

1. A medical pump system that provides advance guidance to a user regarding existence and non-existence of a valid input range for a pump programming parameter, comprising:
    an input device for entering a value of a pump programming parameter;
    a memory for storing constraints related to the pump programming parameter;
    a processor in communication with the memory and the input device, the processor being operable to utilize the constraints to determine and generate a signal, determined from among an affirmative signal and a negative signal, indicating whether a valid input range exists for a to-be-entered value of the pump programming parameter; and
    an output device in communication with the processor to receive the signal indicating whether a valid input range exists for a to-be-entered value of the pump programming parameter and, for both a determination that the signal is the affirmative signal and a determination that the signal is the negative signal, explicitly generate a notification to a user of the medical pump system based on the signal immediately prior to attempted input of the to-be-entered value of the pump programming parameter.

2. The medical pump system of claim 1, wherein the notification indicates to the user that a valid input range for the to-be-entered value is absent.

3. The medical pump system of claim 1, wherein the notification indicates to the user that a valid input range for the to-be-entered value is present.

4. The medical pump system of claim 3, wherein the notification comprises a message identifying an upper limit and a lower limit of the valid input range based upon the signal.

5. The medical pump system of claim 4, wherein the output device is a display screen and the message is generated on the display screen.

6. The medical pump system of claim 1, wherein one of the constraints is derived from a medical device capability predetermined by a manufacturer of the medical pump system.

7. The medical pump system of claim 1, wherein at least one of the constraints is derived from a drug library.

8. The medical pump system of claim 1, wherein the constraints comprise multiple sets of constraints and a smallest maximum constraint among the constraints and a largest minimum constraint among the constraints are used to determine whether a valid range exists and to define the valid range.

9. The medical pump system of claim 1, wherein one of the constraints comprises a predetermined equation that relates the to-be-entered pump programming parameter to a plurality of other pump programming parameters.

10. The medical pump system of claim 9, wherein the predetermined equation is back calculated or solved for the maximum and minimum values of the to-be-entered pump programming parameter based upon a maximum and a minimum of one of the other pump programming parameters.

11. The medical pump system of claim 9, wherein at least one of the plurality of other pump programming parameters has already been entered.

12. The medical pump system of claim 11, wherein the to-be-entered pump programming parameter is rate and among the plurality of previously entered pump programming parameters is one of time and volume to be infused.

13. The system of claim 12 wherein the maximum and minimum values of the to-be-entered pump programming parameter are rounded during calculation.

14. The system of claim 12 wherein the maximum value of the to-be-entered pump programming parameter is truncated during calculation.

15. The system of claim 12 wherein the minimum value of the to-be-entered pump programming parameter is ceiled during calculation.

16. The system of claim 12 wherein when calculated at least one of the maximum and minimum values of the to-be-entered pump programming parameter is compared to a medical device capability constraint.

17. The system of claim 16 wherein the valid range is adjusted after comparison to the medical device capability constraint to create an adjusted valid range.

18. The medical pump system of claim 10, wherein the back calculation of the valid range is dynamically back calculated anytime a related pump programming parameter is altered.

19. The medical pump system of claim 10, wherein the to-be-entered pump programming parameter is recalculated using a second predetermined equation.

20. The medical pump system of claim 5, wherein the message is displayed on the display screen concurrently with an input field for receiving input of the to-be-entered value of the pump programming parameter.

21. A medical pump system that provides advance guidance to a user regarding unavailability of a valid input range for a pump programming parameter, comprising:
    an input device for entering a value of a pump programming parameter;
    a memory for storing constraints related to the pump programming parameter;
    a processor in communication with the memory and the input device, the processor being operable to utilize the constraints to determine and generate a signal indicating unavailability of a valid input range for a to-be-entered value of the pump programming parameter; and
    an output device in communication with the processor to receive the signal indicating the unavailability of a valid input range for a to-be-entered value of the pump programming parameter and generate a notification of the unavailability of a valid input range to a user of the medical pump system based on the signal prior to attempted input of the to-be-entered value of the pump programming parameter.

* * * * *